US007932486B2

(12) United States Patent
Sano et al.

(10) Patent No.: US 7,932,486 B2
(45) Date of Patent: *Apr. 26, 2011

(54) MASS SPECTROMETER SYSTEM

(75) Inventors: Akihiro Sano, Hitachi (JP); Atsumu Hirabayashi, Kodaira (JP); Yasushi Terui, Tsuchiura (JP); Kinya Kobayashi, Hitachi (JP); Kiyomi Yoshinari, Hitachi (JP); Kenko Uchida, Tokyo (JP); Toshiyuki Yokosuka, Hitachi (JP)

(73) Assignee: Hitachi High-Technologies Corporation, Tokyo (JP)

( * ) Notice: Subject to any disclaimer, the term of this patent is extended or adjusted under 35 U.S.C. 154(b) by 206 days.

This patent is subject to a terminal disclaimer.

(21) Appl. No.: 12/330,374

(22) Filed: Dec. 8, 2008

(65) Prior Publication Data

US 2009/0189063 A1 Jul. 30, 2009

Related U.S. Application Data

(63) Continuation of application No. 10/849,517, filed on May 20, 2004, now Pat. No. 7,473,892.

(30) Foreign Application Priority Data

Aug. 13, 2003 (JP) ................................. 2003-207425

(51) Int. Cl.
H01J 49/26 (2006.01)
(52) U.S. Cl. ......... 250/281; 250/282; 250/288; 250/290
(58) Field of Classification Search .................. 250/281, 250/282, 288, 290
See application file for complete search history.

(56) References Cited

U.S. PATENT DOCUMENTS 6,894,276 B1 5/2005 Takada et al.
(Continued)

FOREIGN PATENT DOCUMENTS

JP 10-142196 5/1998
(Continued)

OTHER PUBLICATIONS

Dirk A. Wolters et al., "An automated multidimensional protein identification technology for shotgun proteomics," Analytical Chemistry, vol. 73, No. 23, pp. 5683-5690, Dec. 1, 2001.

(Continued)

Primary Examiner — Robert Kim
Assistant Examiner — Michael Maskell
(74) Attorney, Agent, or Firm — Dickstein Shapiro LLP

(57) ABSTRACT

During the structural analysis of a protein or peptide by tandem mass spectroscopy, a peptide ion derived from a protein that has already been measured and that is expressed in great quantities is avoided as a tandem mass spectroscopy target. A peptide derived from a minute amount of protein, which has heretofore been difficult to analyze, can be automatically determined as a tandem mass spectroscopy target within the real time of measurement. Data concerning a protein that has already been measured and a peptide derived from the protein is automatically stored in an internal database. The stored data is collated with measured data with high accuracy to determine an isotope peak. In this way, the process of selecting a peptide peak that has not been measured as the target for the next tandem analysis can be performed within the real time of measurement and a redundant measurement of peptides derived from the same protein can be avoided. The information contained in the $MS^n$ spectrum is effectively utilized in each step of the $MS^n$ involving a multi-stage dissociation and mass spectroscopy ($MS^n$), so that the flows for the determination of the next analysis content and the selection of the parent ion for the $MS^{n+1}$ analysis, for example, can be optimized within the real time of measurement and with high efficiency and accuracy. Thus, a target of concern to the user can be subjected to tandem mass spectroscopy without wasteful measurement.

6 Claims, 63 Drawing Sheets

U.S. PATENT DOCUMENTS

| | | |
|---|---|---|
| 7,057,169 B2 | 6/2006 | Takada et al. |
| 2002/0027195 A1* | 3/2002 | Kato .............................. 250/288 |
| 2003/0009661 A1* | 1/2003 | Tsutsumi et al. .............. 713/153 |
| 2004/0181347 A1* | 9/2004 | Yoshinari et al. ................ 702/27 |
| 2004/0222369 A1 | 11/2004 | Makarov et al. |
| 2005/0199801 A1* | 9/2005 | Takada et al. .................. 250/288 |
| 2006/0169889 A1* | 8/2006 | Yokosuka et al. ............. 250/288 |
| 2006/0192101 A1* | 8/2006 | Takada et al. .................. 250/282 |
| 2006/0289735 A1* | 12/2006 | Ohtake et al. .................. 250/282 |

FOREIGN PATENT DOCUMENTS

| | | |
|---|---|---|
| JP | 2000-243347 A | 9/2000 |
| JP | 2001-249114 | 9/2001 |
| JP | 2002-184348 A | 6/2002 |
| JP | 2003-014695 A | 1/2003 |
| WO | WO 02/25265 A1 | 3/2002 |

OTHER PUBLICATIONS

Thermo Finnigan Product Support Bulletin, "Dynamic exclusion," PSB 105, pp. 1-2.

Wolfgan Paul, "Electromagnetic traps for charged and neutral particles," Reviews of Moderrn Physics, vol. 62, No. 3, pp. 531-540, Jul. 1990.

* cited by examiner

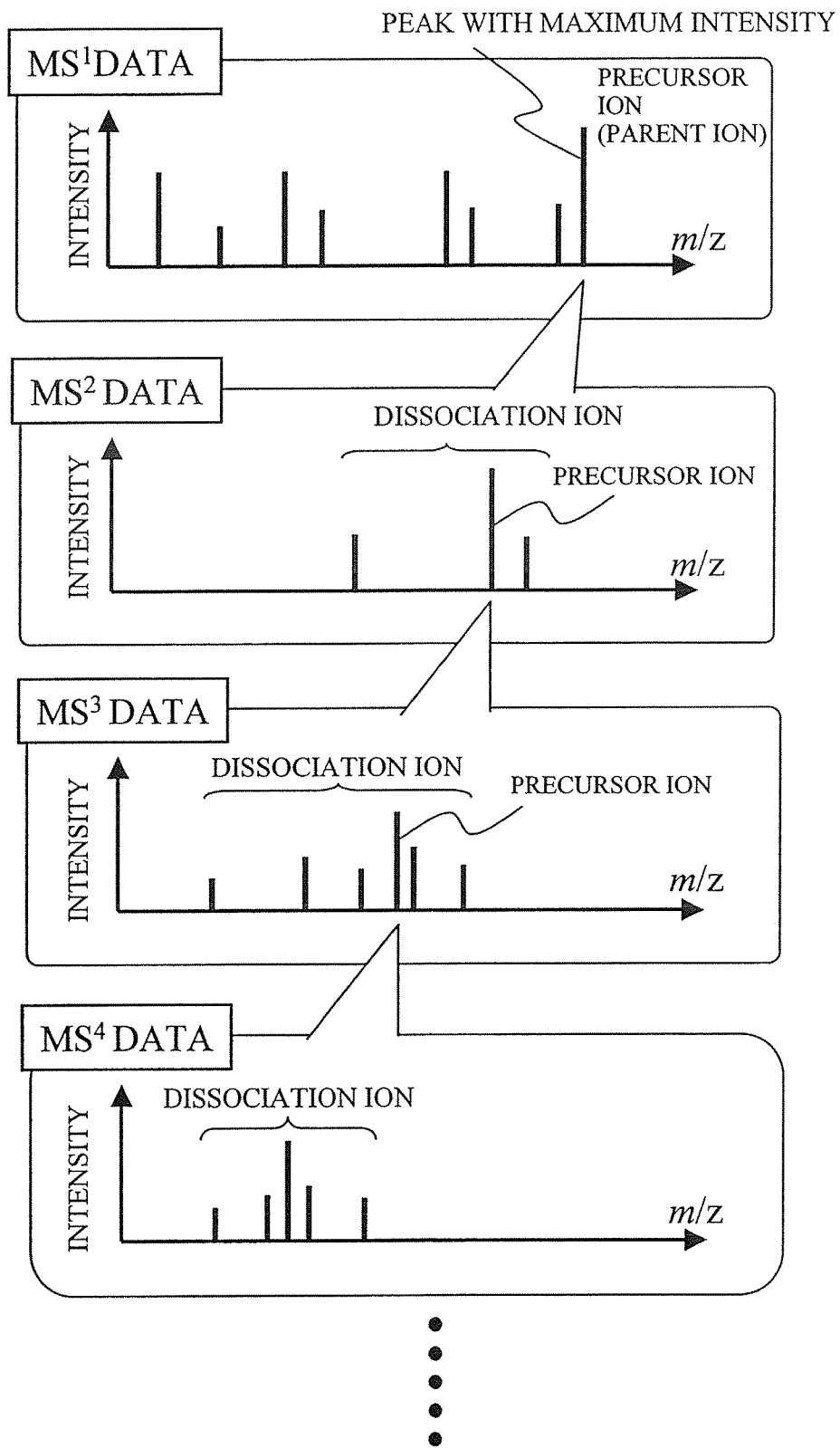

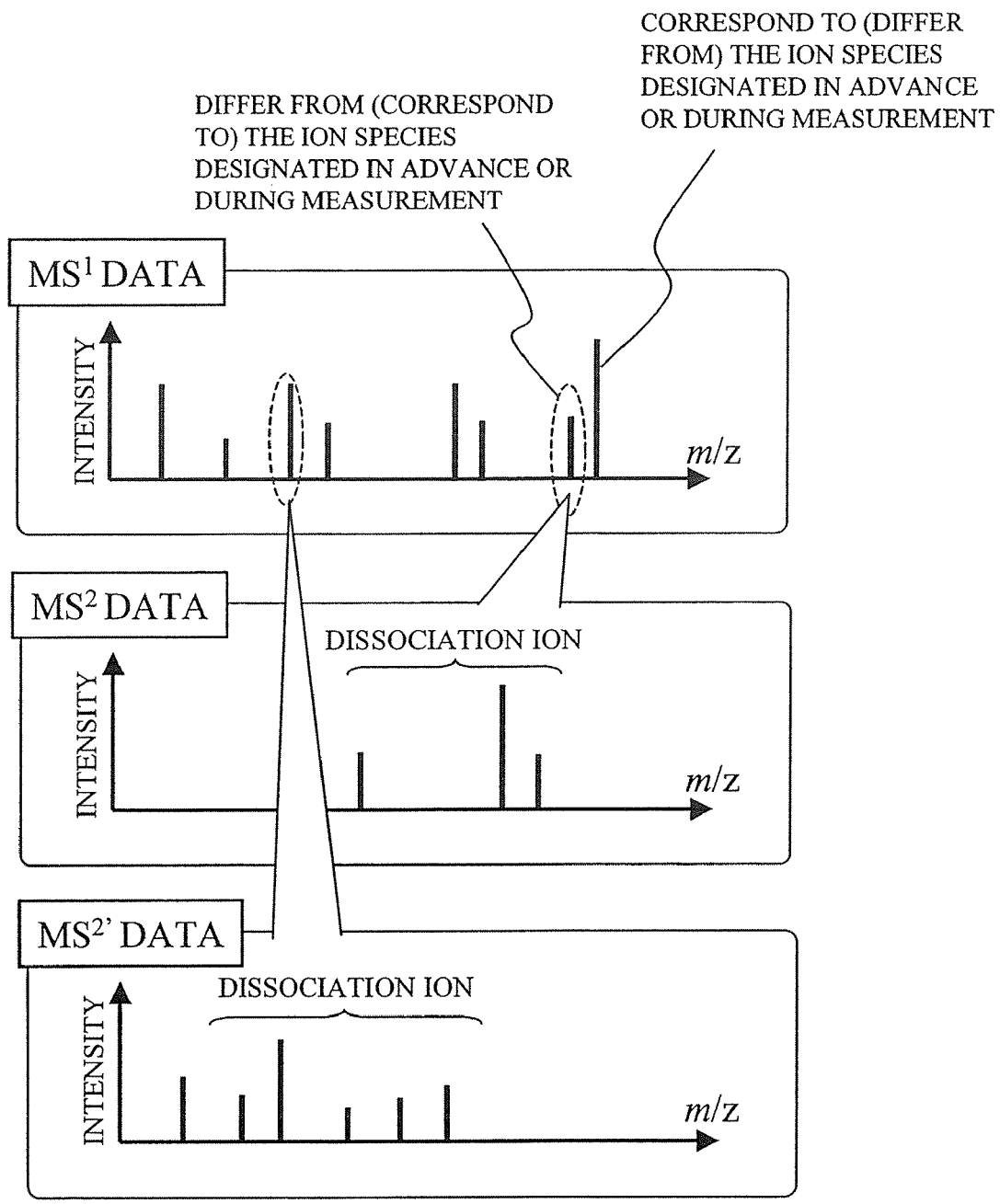

ISOTOPE PEAK INTENSITY DISTRIBUTION
PATTERNS DEPENDING ON ION MASS NUMBER

SELECT AN ION CONTAINING ISOTOPE PEAKS
AS THE NEXT ANALYSIS TARGET ION

| No. | M [Da] | VALENCE $z$ | $\tau$ [min] | Accumulation time[msec] | quality |
|---|---|---|---|---|---|
| 1 | 921.23 | 2 | 24.5 | 260 | 5 |
| 2 | 926.09 | 2 | 26.9 | 345 | 4 |
| 3 | 973.26 | 2 | 32.0 | 289 | 4 |
| 4 | 700.39 | 2 | 34.1 | 401 | 5 |
| 5 | 480.66 | 2 | 39.2 | 269 | 3 |
| 6 | 582.29 | 2 | 44.7 | 159 | 2 |
| 7 | 1638.66 | 2 | 47.8 | 362 | 4 |
| 8 | 1954.86 | 3 | 50.8 | 410 | 5 |
| 9 | 507.8 | 2 | 51.1 | 359 | 5 |
| 10 CLICK | 1510.54 | 2 | 57.6 | 190 | 3 |
| 11 | 740.25 | 2 | 59.8 | 278 | 5 |
| 12 | 1478.5 | 2 | 61.3 | 371 | 4 |

INTERNAL DATABASE

MASS SPECTRUM DATA DISPLAY (FLOWCHAR: SPECIFIC CONDITIONS → MS3/MS2')

(FLOWCHART: DETERMINATION BASED ON PEAK GROUP)

ION TRAP

MASS SPECTROMETER SYSTEM

This application is a continuation of application Ser. No. 10/849,517, filed May 20, 2004, now U.S. Pat. No. 7,473,892 the complete disclosure of which is incorporated herein by reference.

BACKGROUND OF THE INVENTION

1. Field of the Invention

The present invention relates to a mass spectroscopy spectrum analysis system using a mass spectrometer, and to a system for automatically determining an optimum flow of mass spectroscopy within a measurement time in order to identify the chemical structure of biopolymers, such as polypeptides or sugars, with high precision and efficiency.

2. Background Art

In a general mass spectroscopy, a sample as the object of measurement is ionized, and a variety of resultant ions are delivered to a mass spectrometer for measuring the ion intensity for each mass-to-charge ratio m/z, which is the ratio of the mass number m of ion to the valence z. As a result, a mass spectrum is obtained, which consists of a peak of the measured ion intensity (ion peak) for each mass-to-charge ratio m/z value. Such a mass spectroscopic analysis of the ionized sample in a first dissociation step is called $MS^1$. In tandem mass spectrometer, in which multiple-stage isolation is possible, an ion peak having a specific mass-to-charge ratio m/z is selected (the selected ion species is called a parent ion) from the ion peaks detected by $MS^1$, and the thus selected ion is dissociated and broken up by collision with gas molecules or the like. The resultant dissociated ion species is then subjected to mass spectroscopy, thereby obtaining a mass spectrum in a similar manner. The n-stage dissociation of the parent ion and the subjecting of the dissociated ion species to mass spectroscopy are referred to as $MS^{n+1}$. Thus, in the tandem mass spectrometer, the parent ion is dissociated in multiple stages (1, 2, . . . , n stages), and the mass number of the ion species generated in each stage is analyzed ($MS^2$, $MS^3$, . . . , $MS^{n+1}$).

(1) Most of the mass spectrometers capable of tandem analysis are equipped with a data-dependent function whereby, when selecting the parent ion for $MS^2$ analysis from the ion peaks in $MS^1$, the ion peaks are selected in decreasing intensities (such as the ion peaks in the top 10 strongest-intensities) as the parent ions, and then they are subjected to dissociation and mass spectroscopy ($MS^2$).

(2) The ion-trapping type mass spectrometer manufactured by Finningan is equipped with a Dynamic Exclusion function whereby, when selecting a parent ion for $MS^2$ analysis from the ion peaks in $MS^1$, the ion species having a mass-to-charge ratio m/z value that is designated by the user in advance is excluded from the selection as a parent ion.

(3) Known examples relating to the determination of correspondence between a measured ion species and an ion species that has been measured include the following:

Patent Document 1: JP Patent Publication (Kokai) No. 2001-249114 A

Patent Document 2: JP Patent Publication (Kokai) No. 10-142196 A 1998

In Patent Document 1, a characteristic peak in the first-stage spectrum data and the spectrum data in the second stage of the corresponding ion species are stored in a database. In the subsequent measurements, spectrum data obtained by mass spectroscopy in the second stage of a sample as the object of measurement is compared with the second-stage spectrum data in the database in order to determine the degree of correspondence. Data components with the highest degree of correspondence is outputted as the comparison result.

In Patent Document 2, a measurement is continuously carried out during a multiple-stage dissociation measurement without conducting a sample injection process during measurement so that an ion intensity fluctuation due to injection between the $MS^n$ and $MS^{n+1}$ data can be prevented. In this way, the need for the addition of a standard sample can be eliminated, thereby enabling an efficient quantitative analysis. The routine returns to $MS^{n+1}$ or proceeds to the next $MS^1$ measurement, depending on whether or not the data corresponds to the designated ion data that has been already collected in the $MS^n$ and $MS^{n+1}$ data analysis.

Reviews of Modern Physics, Vol. 62 (1990), pp. 531-540, provides a basic description of an ion trap. A cross section of a basic configuration of the ion trap is shown in FIG. 15. The ion trap, which is a quadrupole ion trap, is made up of two end-cap electrodes and a single ring electrode. An RF voltage is applied to these electrodes such that a quadrupole electric field is formed at the center of these electrodes, thus enabling the trapping of gaseous ions three dimensionally. By continuously varying the RF voltage, the mass of the ions that are discharged can be controlled. A quadrupole pole is made up of four parallel poles. By applying a RF voltage to the electrodes, gaseous ions can be two dimensionally trapped at the center of the electrodes. By controlling the RF voltage that is applied, it becomes possible to discharge ions with a specific mass or, conversely, trap only those ions with a specific mass.

A tandem mass spectroscopy (MS/MS) can be conducted using a quadrupole ion trap, as described in the U.S. Pat. No. Re. 34000. In this apparatus, those ions for which no analysis is required are discharged prior to MS/MS. Namely, the removal of the ions for which no analysis is required is not conducted prior to the primary mass spectroscopy. A RF voltage that resonates with the ions is then applied in order to increase the kinetic energy. As a result of these operations, dissociated ions (fragment ions) are created by the collision induced dissociation (CID) with remaining molecules. By subjecting these fragment ions to mass spectroscopy (tandem mass spectroscopy), the mass of the fragment ions can be determined. In this case, it is necessary to initially conduct a mass spectroscopy without involving a CID (primary mass spectroscopy) in order to determine the ions as the object of a tandem mass spectroscopy (MS/MS, or a secondary mass spectroscopy). It is also possible to repeat a similar operation to further conduct a tandem mass spectroscopy ($MS^n$) on a specific dissociated ion.

Recently, mass spectroscopic methods are often employed for an exhaustive analysis of proteins. Analytical Chemistry, Vol. 73 (2001), pp. 5683-5690, describes examples of analysis called a shotgun analysis. In this technique, a peptide mixture prepared by subjection a protein to enzymatic digestion is separated using a liquid chromatograph, and a separated sample is then subjected to a tandem mass spectroscopy using a quadrupole ion-trap mass spectrometer. With reference to the determined mass of the ion and that of the fragment ion, a database of proteins or genes is searched in order to identify a protein. In case the types of the peptide mixture are too numerous, each peptide might not be completely separated in the liquid chromatograph, and a plurality of kinds of peptides might be simultaneously introduced into the mass spectrometer. This gives rise to the need for automatic tandem analysis called data-dependent analysis. Specifically, the band width of a separated sample separated in a liquid chromatograph is in the order of one minute, and the number of kinds of ions that can be subjected to tandem mass spectrometer at one time is limited to five. In many cases, the ions with greater ion intensities are preferentially subjected to tandem mass spectroscopy, although this depends on the setting of the data-dependent analysis.

A technical material for the quadrupole ion-trap mass spectrometer manufactured by ThermoFinnigan (www.thermo-.com/eThermo/CMA/PDFs/Articles/articlesFile_10918.pdf) describes a dynamic exclusion function. Prior to the start of analysis, the masses of those ions to be excluded from tandem mass analysis are entered and then a list is prepared. By this operation, it becomes possible to exclude those ions put on the list as the objects of data-dependent analysis (tandem mass spectrometer). When this function is to be employed, a conventional mass spectroscopy is conducted first without involving the CID, and then the mass of the ions to be detected is determined. Next, priorities of the ions as the objects of tandem mass spectroscopy are determined in the detected ions, whereupon those ions put on the list are excluded from the objects of data-dependent analysis (tandem mass spectroscopy).

SUMMARY OF THE INVENTION (1) With the data-dependent function referred to in (1) of the Background of Art section, as proteins that are expressed in great quantities or peptides derived from proteins are preferentially subjected to tandem analysis, the possibility is very high that proteins or peptides that have already been identified are redundantly measured, which would lead to a waste of measurement time and the sample. Although the focus of analysis has so far been centered on those proteins that are expressed in great amounts, it is expected that the focus will shift toward the analysis of minute quantities of proteins such as pathologic proteins in the future. With the data-dependent function, it is difficult to perform tandem analysis of minute amounts of proteins in detail.

(2) According to the dynamic exclusion function referred to in (2) of the Background Art section, it is determined whether or not an ion species has the mass-to-charge ratio m/z value designated by the user in advance on the basis of the mass-to-charge ratio m/z value. Thus, there is the possibility that the ion species with different mass number m or valence z but with the same the mass-to-charge ratio m/z value are similarly excluded from the targets of the $MS^2$ analysis.

In order to avoid this problem, it is necessary to make the determination as to whether or not an ion species is that which has been designated in advance based on the valence z and mass number m of each ion peak, rather than on the mass-to-charge ratio m/z value, although the mass-to-charge ratio m/z value of each ion peak is apparent from the mass spectrum. In this determination, it is necessary to calculate the valence z and mass number m of each ion peak on a real-time basis during measurement.

In Patent Documents 1 and 2, for the $MS^n$ data analysis, the identification of a specific ion species is conducted by referring to a database, for example. In Patent Documents 1 and 2 too, the registered values in the database are mass-to-charge ratio m/z values, and the mass number m is not necessarily employed. Alternatively, monovalent ions (z=1) have been presumed. Information obtained from the MS analysis other than the measurement values of the mass-to-charge ratio m/z (such as the characteristic data for each of the valence z and mass number m) is not utilized either. Thus, it cannot be said that appropriate information has been utilized for an efficient selection of ions.

(3) When the number of amino acid residues constituting a peptide chain is K and the number of kinds of amino acids is 20, the number of possible amino acid sequences is as many as $20^K$. Add to this the chemical modifications to the amino acid side chains, and the number becomes much larger. Further, as the number of amino acid residues increases, so does the number of the isotopes of the peptide chains. In particular, while the intensity of the isotope peaks decreases with regard to small peptide chains, the intensity of the isotope peaks actually becomes stronger in the case of large peptide chains. If the isotope peaks are set as the parent ion species for the subsequent dissociation measurement, the accuracy of search and collation in a protein database that is eventually conducted drops significantly, so much so that, for large peptides, data processing might become difficult.

In order to solve the aforementioned problem, it is necessary to effectively utilize the information contained in the $MS^n$ spectrum in each stage of $MS^n$, and to perform the selection of the parent ion for the determination of the subsequent analysis content and for the $MS^{n+1}$ analysis within the real-time of measurement efficiently and accurately.

Moreover, of the mixture samples that are simultaneously introduced into the mass spectrometer, the number of those samples that can be subjected to tandem mass spectroscopy is limited. In particular, since there are much impurity components in the aforementioned shot gun analysis, for example, there are many cases in which ions exist that have such a low ion intensity that a tandem mass spectroscopy cannot be conducted thereon, which leads to the problem that the tandem mass spectroscopy cannot be conducted on a minute amount of a sample that needs analysis. This is due to the fact that even with the data-dependent analysis, ions with greater ion intensities are preferentially subjected to tandem mass spectroscopy such that only those ions that are not the objects of analysis can possibly be analyzed. The aforementioned dynamic exclusion method is effective only in cases where the substances that do not need analysis are known in advance. In cases where unknown impurity components are present in great quantities, it might be impossible to conduct a tandem mass spectroscopy on a minute amount of a sample that needs analysis.

In view of the foregoing, it is an object of the invention to provide a tandem mass spectroscopy employing a mechanism for selecting an analysis-target ion and, optionally, a non-analysis target ion, prior to the primary mass spectroscopy, so that a minute amount of a sample that needs analysis can be analyzed even in cases where unknown impurity components are present in great quantities.

In order to solve the aforementioned problems (1) to (3) in a mass spectrometer capable of tandem analysis, the invention provides a system in which mainly the below-indicated means (1) to (5) are adopted. In this system, a target ion is subjected to dissociation n−1 times and then to mass spectroscopy, and the resultant mass spectrum ($MS^n$) is subjected to fast analysis within the real-time of measurement in order to determine the subsequent analysis content.

(1) It is determined, at a high speed, whether or not each ion peak in the mass spectrum ($MS^n$) is an isotope peak.

(2) If the ion peak is determined to be an isotope peak, the valence z and mass number m of the ion peak are calculated from the interval 1/z of the isotope peaks, and it is then determined, based on the mass number m, whether or not the ion peak corresponds to the ion species that has been designated in advance.

(3) In cases where a liquid chromatography (LC) is installed in a stage prior to the mass spectrometer, the retention time of LC is also used as a factor in making the determination, in order to distinguish ion species with the same mass number m but with different structures.

(4) In order to prevent redundant measurement, data concerning the mass numbers or retention time of peptides that have already been measured once or of those peptides derived from proteins that have already been identified is stored in an internal database built inside the mass spectroscopy system. It is then determined at high speed whether or not the stored data corresponds to each ion peak in the mass spectrum ($MS^n$).

(5) During the selection of the next analysis target, isotope peaks are avoided.

The aforementioned object of the invention is achieved by the following features:

(1) Using a first database in which the data about an analysis object candidate substance is recorded and an RF power supply for applying an RF voltage for the elimination of an ion that is not an analysis object, an ion that is not listed in the first database and that is not an analysis object, or a non-analysis object ion that corresponds to the data in a second database in which data about non-analysis object candidate substance is recorded, is eliminated by the RF voltage prior to a primary mass spectroscopy. In this way, the adverse influence from non-analysis object ions can be avoided and an analysis object ion can be detected in mass spectroscopy.

(2) Alternatively, after the primary mass spectroscopy and before the dissociation process involving collision induced dissociation (CID) with remaining molecules and the mass spectroscopy (tandem mass spectroscopy) of a dissolved ion, an analysis object ion listed in the first database in which data about an analysis object candidate substance is recorded is selected and subjected to CID, and then tandem mass spectroscopy is performed. As a result, an analysis object ion that exists in only minute amounts can be reliably subjected to tandem mass spectroscopy.

(3) The features (1) and (2) may be combined.

DESCRIPTION OF THE PREFERRED EMBODIMENTS

Figure 1:
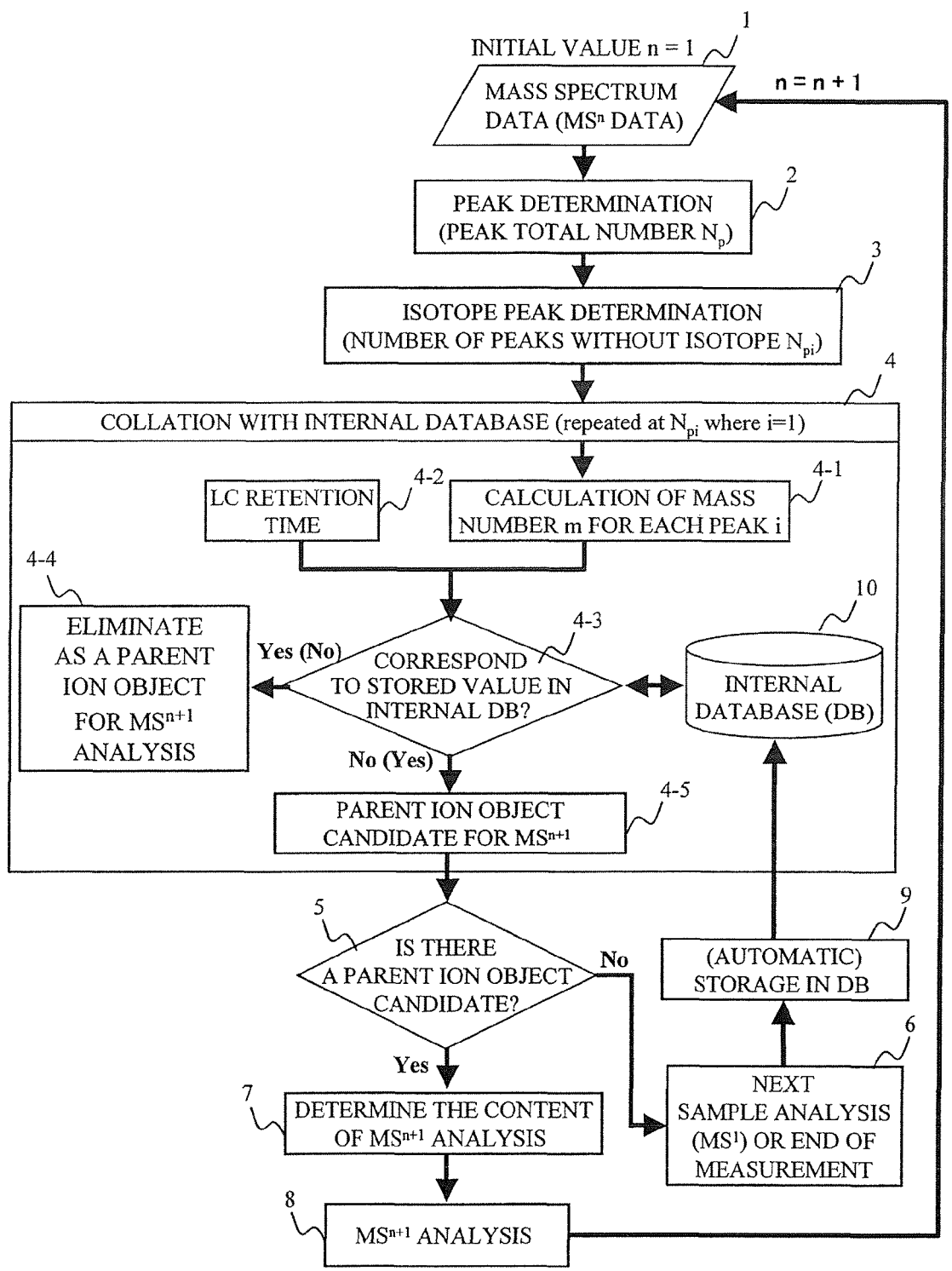
FIG. 1 schematically shows the flow of an automatic determination process in the mass spectroscopy flow according to a first embodiment of the invention.

Embodiments of the invention will be hereafter described by referring to the drawings.

A first embodiment will be described. FIG. 1 shows a flowchart of a process for automatically determining the analysis content in a mass spectroscopy system according to the first embodiment of the invention. Mass spectroscopy data 1 refers to the data measured in a mass spectroscopy system 19 shown in FIG. 2. In the mass spectroscopy system 19, a sample as the object of analysis is preprocessed in a preprocessing system 11, such as a liquid chromatography. For example, if the sample is a protein, the protein is broken up by a digestive enzyme into the size of polypeptides, and then separated and fractionated by gas chromatography (GC) or liquid chromatography (LC) in a preprocessing system 11. In the following description of an example, LC is adopted as the separating and fractionating system in the preprocessing system 11. After the separation and fractionation of the sample, the sample is ionized in an ionization unit 12 and is then separated in a mass spectroscopy unit 13 depending on the mass-to-charge ratio m/z of the ion, where m is the mass of the ion and z is the charge valence thereof. The separated ion is detected in an ion detection unit 14 and the data is then arranged and processed in a data processing unit 15. The result of analysis, namely the mass spectroscopy data 1, is displayed by a display unit 16. The entire series of mass spectroscopy process—the ionization of the sample, transport and incidence of the sample ion beam onto the mass spectroscopy unit 13, the step of mass separation, ion detection, and data processing—is controlled by a control unit 17.

Mass spectroscopy methods can be roughly divided into those whereby a sample is ionized and then analyzed as is (MS analysis methods), and the tandem mass spectroscopy methods whereby a specific sample ion (parent ion) is selected based on its mass, the parent ion is dissociated, and then the resultant dissociated ion is subjected to mass spectrometer. The tandem mass spectroscopy methods also have a function for performing the dissociation and mass spectroscopy in multiple stages ($MS^n$) such that ions (precursor ions) with a specific mass-to-charge ratio are selected from the dissociated ions, the precursor ions are further dissociated, and the resultant dissociated ions are subjected to mass spectroscopy. Specifically, after measuring the mass analysis distribution of substances in the original sample as mass spectrum data ($MS^1$), parent ions with a certain m/z value are selected and then dissociated. After measuring the mass spectroscopy data ($MS^2$) of the resultant dissociated ions, the selected precursor ions are further dissociated, and the mass spectroscopy data ($MS^3$) of the resultant dissociated ions is measured, thus performing the dissociation and mass spectroscopy process in multiple stages ($MS^n(n \geq 3)$). In each stage of dissociation, information about the molecular structure of the precursor ions in a state prior to dissociation is obtained, which is very useful in estimating the structure of the precursor ions. The more detailed the structural information of the precursors, the higher the accuracy of estimation becomes of the structure of the parent ion, which is the original structure.

Figure 2:
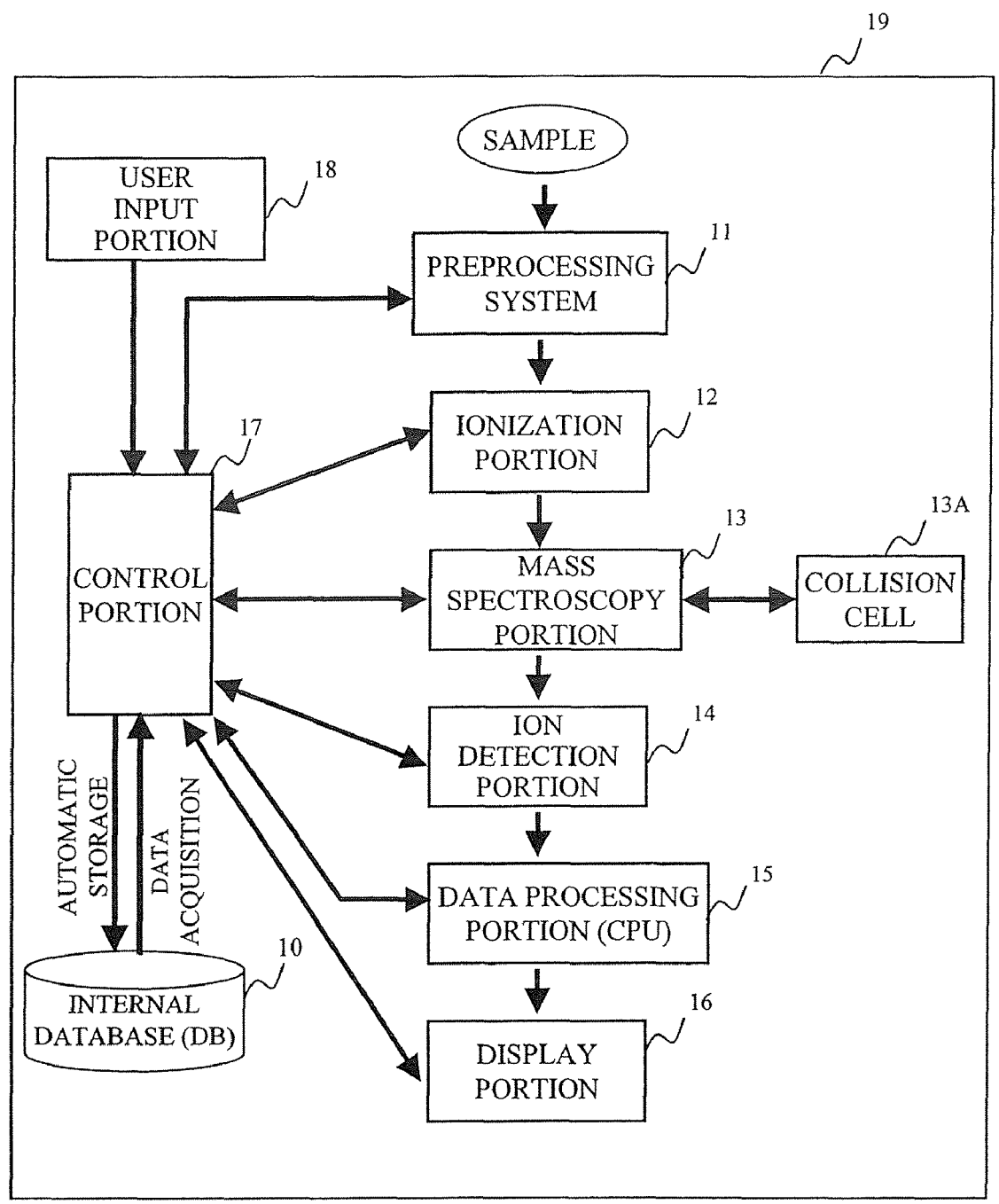
FIG. 2 schematically shows a mass spectroscopy system as a whole for measuring mass spectroscopy data in the first embodiment of the invention.

In the present embodiment, as a method of dissociating the precursor ions, the collision induced dissociation method is adopted, whereby the precursor ions are caused to collide with buffer gas, such as helium, in order to dissociate the ions. For the collision induced dissociation, a neutral gas, such as helium gas, is required. Thus, a collision cell 13A for collision induced dissociation may be provided separately from the mass spectroscopy unit 13, as shown in FIG. 2. Alternatively, however, a neutral gas may be filled in the mass spectroscopy unit 13 so that the collision induced dissociation can take place within the mass spectroscopy unit 13. In this case, the collision cell 13A may be dispensed with. Further alternatively, the electron capture dissociation technique may be employed as the dissociation means, whereby low-energy electrons are irradiated in order to allow the parent ions to capture large amounts of low-energy electrons so that the target ions can be dissociated.

Figure 3:
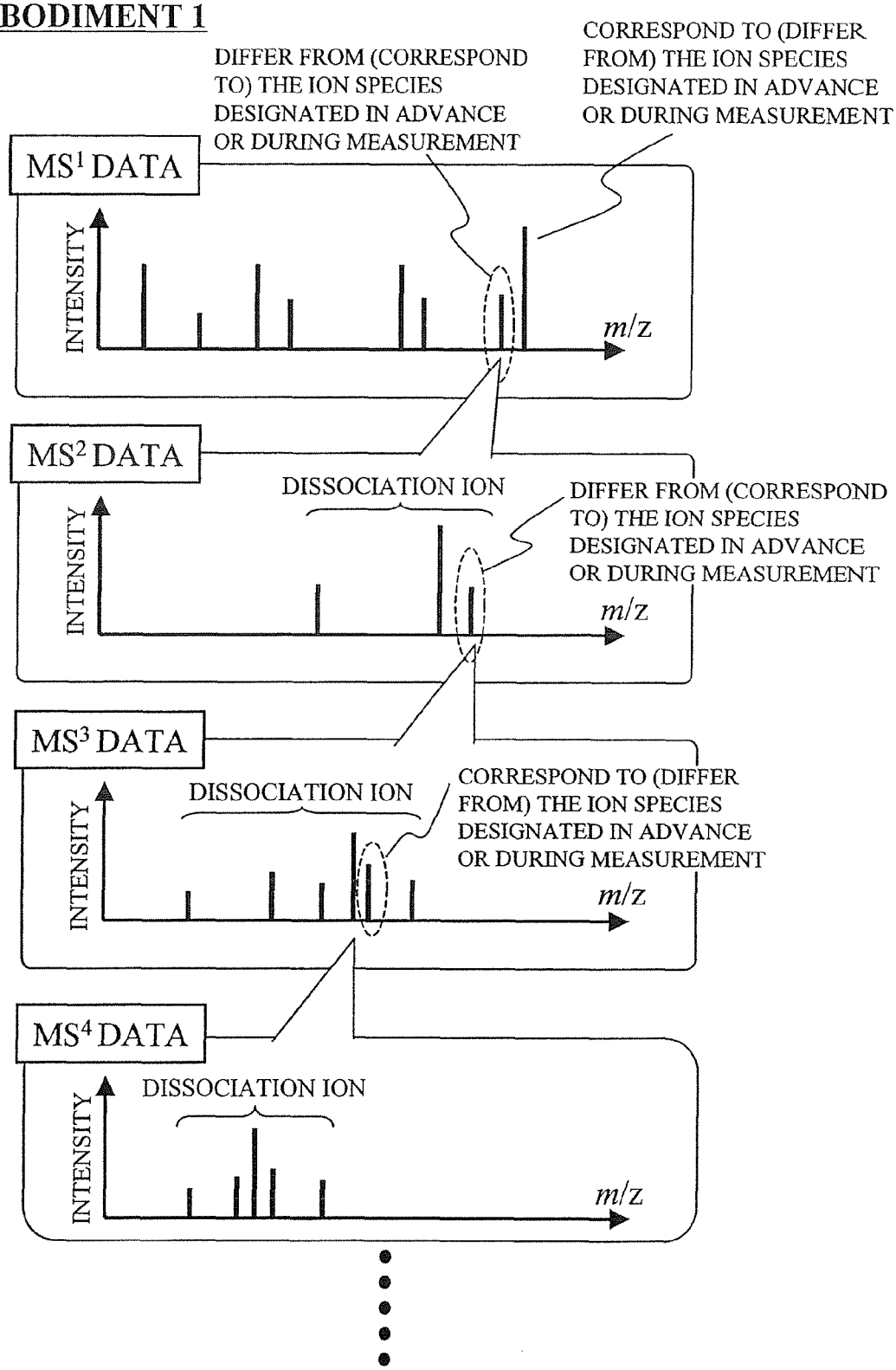
FIGS. 3A, 3B and 3C show examples of a multi-stage dissociation and mass spectroscopy flow.

FIG. 3A shows a conventional method of automatically determining the flow of tandem mass spectroscopy. When further selecting a target ion (parent ion) for dissociation and mass spectroscopy from the spectrum of $MS^1$, which is the mass spectroscopy distribution of the substances in the sample according to the conventional technique, ions are selected in the order of decreasing intensities. Even during the selection of precursor ions in $MS^2$ and thereafter, ion peaks with higher intensities are similarly selected. In this type of automatic method of determining the flow of tandem mass spectroscopy, when the sample is a protein, for example, peptide ions that have been enzymatically broken down from proteins that are expressed in great quantities tend to become the target of tandem mass spectroscopy. As a result, it becomes more likely that those proteins that are expressed in great quantities are exclusively analyzed in redundant manner.

Figure 4:
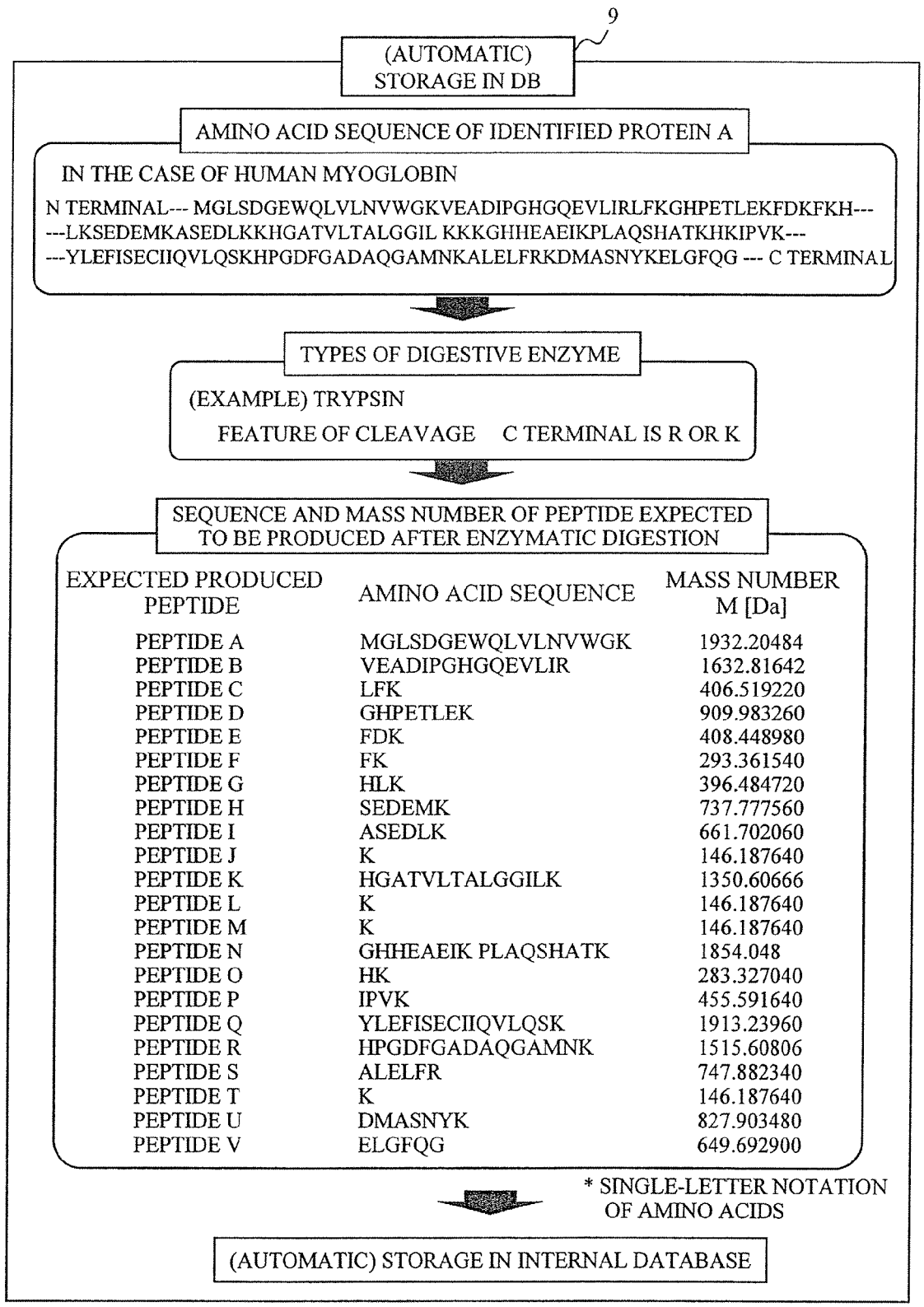
FIG. 4 schematically shows the content of an internal database automatic storage process.

Thus, in accordance with the invention, it is determined whether the mass number m of all of the peptides that are expected to be produced upon enzymatic hydrolysis of pre-designated proteins, or the retention time of LC corresponds to the value of each ion peak in the measured $MS^1$. Then, based on the result of determination, the parent ion that is to become the target for the next tandem mass spectroscopy is automatically determined on a real-time basis during measurement (such as within 100 msec, 10 msec, 5 msec, or 1 msec). For example, a case is considered where a protein A that is expressed in great quantities has already been measured and identified, and only those minute amounts of proteins that have not been measured are to be subjected to tandem mass spectroscopy. As shown in FIG. 4, peptides that are expected to be produced by the enzym-digestive cutting of the amino acid sequence of protein A, as an identified protein, that has been predesignated are listed. At the same time, the manner of cutting of the amino acids is modified based on the type of digestive enzyme that was entered in advance by the user via a user input unit 18 and that was used in the preprocessing system 11. For example, in the event that the user selected trypsin as the digestive enzyme in the preprocessing system 11, if there is arginine (R) or lysine (K) in the amino acid sequence as the characteristics of the cutting of the amino acid sequence of the protein, the binding between R or K and the amino acid bound to the C terminal thereof is cut off. In an exception, however, if proline (P) is bound to the C terminal of R or K, that binding is not cut off. Namely, as the characteristics of the peptide that is cut off, the amino acid at the C terminal is either R or K at all times. The amino acid at the N terminal does not become P except in cases where the amino acid at the N terminal is P in the amino acid sequence of the original protein. Such a cutting rule differs from one digestive enzyme to another. As an example of the digestive cutting process, a case will be considered where protein A is human myoglobin. In the event that human myoglobin with the amino acid sequence shown in FIG. 4 is enzymatically digested with trypsin, the production of 22 kinds of peptides shown in FIG. 4 can be expected based on the aforementioned cutting rule concerning trypsin enzymatic digestion. Thus, cleaved peptides in accordance with the cutting rule of digestive enzyme are derived, and the amino acid sequence and mass number are determined for each of the derived peptides and then stored in an internal database 10. In the case where the peptide ion derived from a protein designated by the user is the "Ion species designated in advance or during measurement" shown in FIG. 3B, the characteristics data concerning the peptide ion (such as the mass number and the retention time data, if any, for LC) derived from the user-designated protein, as described above, are already stored in the internal database 10. Accordingly, the $MS^1$ data that has just been measured is read at a high rate, and then the internal database 10 is searched within a preparation time (such as 100 msec, 10 msec, 5 msec, or 1 msec) before the next measurement to see if the $MS^1$ data corresponds, with a certain tolerance, to the stored data in the database 10. From the peaks of the ion species that do not correspond, within a certain tolerance, to the stored data in the internal database 10, ions are selected in decreasing order of intensity as the parent ions for $MS^2$, which is the next tandem analysis. The parent ions are dissociated to obtain dissociated ions, which are then subjected to mass spectroscopy in the $MS^2$ analysis. If, for example, all of the peaks that appeared in the $MS^1$ data correspond, within a certain tolerance, to the stored data in the internal database 10, it is determined that there is no appropriate peak for the parent ion for the $MS^2$ analysis, and the routine automatically proceeds to the measurement for the $MS^1$ analysis instead of the $MS^2$ analysis. Thus, in accordance with the present embodiment, in the case where proteins that are expressed in great quantities or proteins that have already been measured or identified are designated in advance, and the characteristics data (such as the mass number and the retention time for LC) for the peptides derived from those proteins is stored in the internal database 10, the peptides derived from the proteins that are expressed in large quantities can be excluded from the targets for the next tandem analysis. Thus, the possibility is increased that ion peaks with relatively low intensities become the target of tandem mass spectroscopy. In other words, as compared with the conventional cases where the tandem analysis is focused on ions with high intensities, the number of proteins that are identified can be expected to increase in accordance with the present embodiment.

Figure 5:
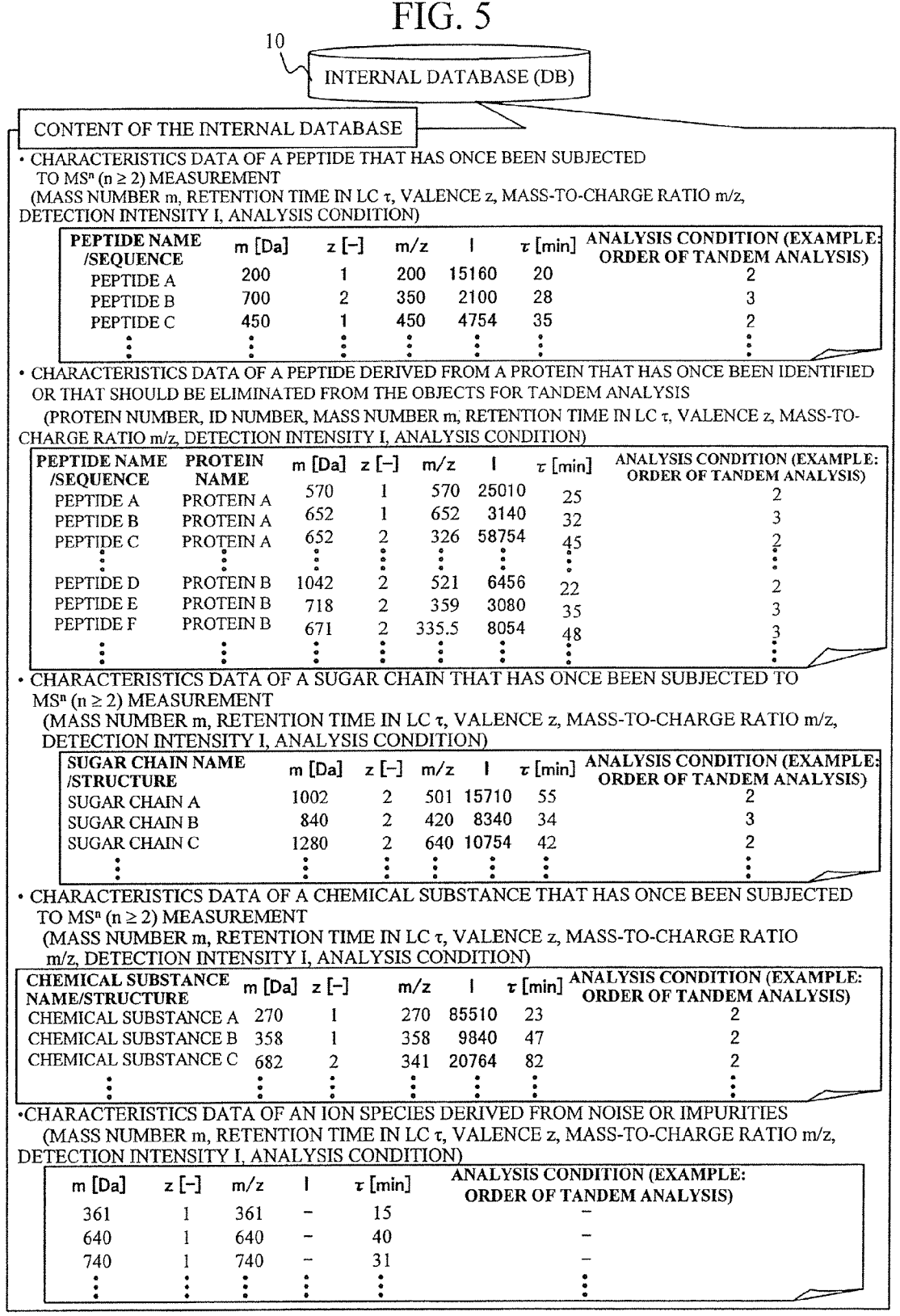
FIG. 5 schematically shows the internal database storage content according to the invention.

In the above-described example, the target substance about which the characteristics data is stored in the internal database 10 has been proteins that are expressed in large quantities or peptides derived from proteins that have already been measured and identified. However, as shown in FIG. 5, it is also possible to store the characteristics data about the ion species (such as a peptide, a sugar chain, a peptide with a modification structure, or a chemical substance) that has been once subjected to the $MS^n$ ($n \geq 2$) analysis in the internal database 10 during measurement as needed so as to avoid an overlap of tandem analysis on the same ion species. Moreover, in accordance with the present embodiment, it is also possible to store the characteristics data about the ion species derived from noise or impurities in the internal database 10 so as to avoid conducting the tandem mass spectroscopy ($MS^n$) on noise or impurities. The ion species derived from noise or impurities may be designated by the user in advance. Alternatively, the ion species that has been determined to be noise may be automatically stored in the internal database 10 during measurement.

Via the user input unit 18, the user can enter information indicating whether or not an isotope peak detection is necessary, whether or not a collation and search with reference to the internal database is necessary, the tolerance for the determination of data correspondence in the collation and search with reference to the internal database, and the resolution during the selection of the parent ion, for example, in addition to the types of digestive enzyme.

The present embodiment is also characterized in that as the characteristics data about the ion species that is designated either in advance or during measurement, the mass number, rather than the mass-to-charge ratio m/z, is used. When the mass-to-charge ratio m/z is utilized as the characteristics data to be checked against the stored data in the internal database 10, those ion species with corresponding m/z values but with different mass number m or valence z are prevented from being selected as the target of tandem mass spectroscopy. On the other hand, by employing the mass number m as the data to be checked, as in the present embodiment, those ion species with corresponding m/z values but with different mass number m or valence z can be recognized, so that the targets for tandem mass spectroscopy can be more accurately selected. Moreover, those corresponding ion species (with the same mass number m) with different valence z or m/z values can be recognized as the same ion species, so that they can be prevented from being selected as targets for tandem mass spectroscopy over and over again. Alternatively, ion species with the same mass number m and different valence z may be recognized as separate ion species and selected as targets for tandem mass spectroscopy.

Since there exist different ions species with the same mass number m, the data concerning the retention time of LC in the preprocessing system 11 may be stored in the internal database 10 and then utilized. When the sample passes through the LC column, the equilibrium constant of adsorption and desorption onto the LC column differs due to the chemical characteristics of the substance, resulting in different lengths of time (retention time or holding time) it takes for the sample to exit the column. Thus, it is possible to distinguish different species with the same mass number m by taking advantage of the aforementioned fact, i.e., based on the difference in the LC retention time arising from different chemical structures or characteristics. In accordance with the present embodiment, the determination as to whether or not a particular ion species is an ion species designated in advance or during measurement is made on the basis of data capable of more accurately specifying the ion species, such as the mass number and the retention time of LC. Thus, only those targets that are to be subjected to tandem mass spectroscopy can be accurately analyzed, thereby enabling the user to obtain desired analysis data without wasteful measurement.

Hereafter, the content of the characteristics data will be described. As shown in FIG. 5, with regard to the ion species (such as a peptide, sugar chain, a peptide with a modification structure, chemical substance, and impurity-derived substance) on which analysis has been conducted up to the $MS^n$ ($n \geq 2$) analysis, the mass number m, valence z, mass-to-charge ratio m/z, the retaining time $\tau$ of LC, ion intensity, and analysis conditions are stored as the characteristics data. In the case where the peak of the ion species that has been referred to when deriving the mass number m is accompanied by an isotope peak, the mass number m is that of the peak that does not include an isotope. The analysis conditions include the operation conditions concerning the mass spectrometer (such as the value of the voltage applied to the electrodes, the analysis sequence, and so on), the value of n in the tandem analysis $MS^n$ ($n \geq 2$) conducted on the particular ion species, the date of measurement, and the column numbers of LC or GC used. Other information that may be stored in the internal database 10 include: the ratio of solvent or mobile phase of LC or GC; the flow volume or gradient of LC or GC; the number of the sample divided in the ion exchanger in a one-dimensional LC in cases where a two-dimensional LC is employed; the spot position, number or coordinates in the sample plate in cases where a MADLI ion source is employed; and the content of measures taken with regard to the ion species that corresponded to the stored characteristics data (namely, whether the ion species that corresponded to the stored characteristics data should be avoided as a target for the $MS^n$ ($n \geq 2$) analysis, whether or not the ion species should be selected in a preferential manner as a target for the $MS^n$ ($n \geq 2$) analysis, or whether or not the ion species should be removed when the ion is injected into the mass spectroscopy system, or prior to the injection). The content of measures taken with regard to the ion species that corresponded to the stored characteristics data may alternatively be designated by the user for each ion species. In the case where, as the content of measures taken with regard to the ion species that corresponded to the stored characteristics data, the ion species is designated to be removed upon or prior to the injection of the sample into the mass spectroscopy system, if an ion reservoir portion or function is provided, such as an ion trap (FIG. 22b) or a linear trap (FIG. 24b), a measure may be taken to prevent the trapping of an ion in the ion reservoir portion by, for example, applying an auxiliary voltage in an superposed manner in order to resonate and discharge the ion that needs to be removed (FIG. 22b or 24b), upon injection of ions into the ion reservoir portion. In particular, those ions for which no analysis with very high intensity is required may be registered in the internal database with a comment "To be removed upon or prior to injection of the ion into the mass spectroscopy system". In this way, the accumulation of large quantities of impurity ions can be avoided, so that low-intensity ions can be accumulated very efficiently and can be expected to be subjected to highly accurate analysis.

Depending on the content of measures taken on the ion species that correspond to the stored characteristics data (namely, whether or not the ion species corresponding to the stored characteristics data should be avoided as a target for the $MS^n$ ($n \geq 2$) analysis, whether or not the ion species should be preferentially selected as a target for the $MS^n$ ($n \geq 2$) analysis, or whether or not the ion species should be removed upon or prior to the injection of the ion into the mass spectroscopy system), the internal database may be divided or layered in structure in advance.

Figure 43:
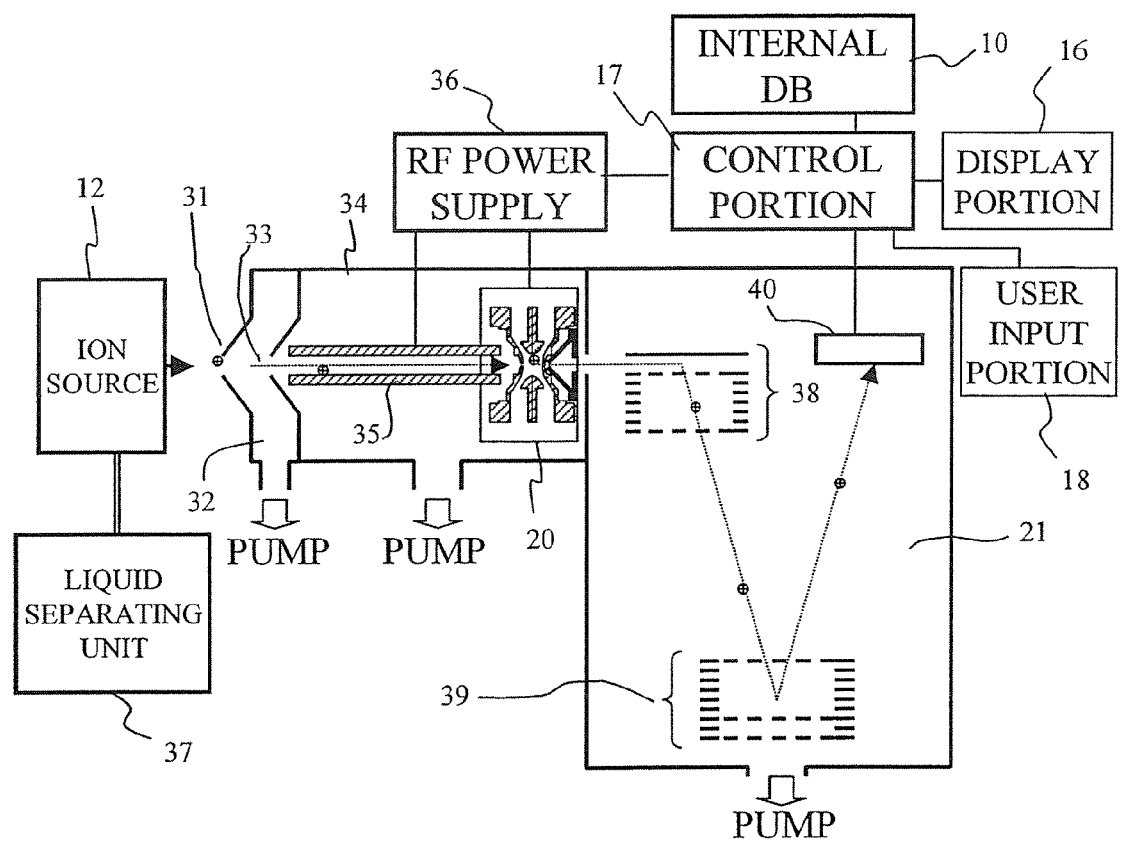
FIG. 43 shows an example of apparatus configuration in the first embodiment of the invention.

FIG. 43 shows a diagram of the structure of the mass spectroscopy system according to an embodiment of the invention. The mass spectrometer is a quadrupole ion trap time-of-flight mass spectrometer. A sample solution separated in a liquid separating unit 37, such as a liquid chromatograph, is introduced into an ion source (ionization unit) 12 where it is converted into a gaseous ion by a spray ionization method, such as the electrospray ionization method and the sonic spray ionization method. The resultant gaseous ion is introduced into a differential pumping unit 32 via a pore 31. The gaseous ion is further introduced into a high vacuum unit 34 via a pore 33 in which the gaseous ion is passed through an ion transportation unit 35 consisting of a multipole pole, for example, and then introduced into an ion trap 20. A radio-frequency voltage is supplied to the ion trap 20 from a radio-frequency power supply 36 so that the gaseous ion is trapped at the center of the ion trap 20 by a quadrupole electric field. With regard to those ions that are not desired to be trapped in the ion trap 20 (non-analysis target ions), a radio-frequency voltage can be applied to the multipole pole in the ion transportation unit in order to remove the ions in the ion transportation unit 35. Further, in cases where the multipole pole is not employed in the ion transportation unit 35, a radio-frequency voltage is applied to the ion trap 20 such that the non-analysis target ions in the ion trap can be removed by resonance discharge, for example, and the other ions can be trapped. The gaseous ion that has been trapped for a certain period of time is transported toward right by an electric force, and then introduced into an ion acceleration unit 38 in a time-of-flight mass spectrometer 21. In the ion acceleration unit 38, a pulsed high voltage is applied to the introduced gaseous ion at a certain timing in order to accelerate the gaseous ion until it has a certain kinetic energy. The accelerated gaseous ion has its trajectory altered by a reflector 39 and has its energy focused, before it is detected by a detector 40. The length of the ion trajectory between the ion acceleration unit 38 and the detector 40 is predetermined, and the ion velocity is smaller with increasing m/z (mass/charge number) of the ion. Consequently, the ions are detected by the detector 40 in the order of increasing m/z. The output of the detector 40 is fed to an information processing unit where the m/z of the ions is determined based on the ion detection time, thereby obtaining a primary mass spectroscopy ($MS^1$) result. Based on the thus obtained primary mass spectroscopy ($MS^1$) result, the order of priority of the ions as the target of the secondary mass spectroscopy ($MS^2$) is determined in the information processing unit (data processing unit 15). Thereafter, in order to apply to the ion trap 20 a radio-frequency voltage for isolating only those ions that are to become the target of the secondary mass spectroscopy ($MS^2$) from the ions introduced into the ion trap 20, an instruction is given from the information processing unit (data processing unit 15) to the radio-frequency power supply 36. Further, an instruction for dissociating the isolated ions by CID or the like is given from the information processing unit (data processing unit 15) to the radio-frequency power supply 36, whereby dissociated fragment ions are produced in the ion trap 20. The fragment ions are transported toward right by an electric force and then introduced into the ion acceleration unit 38 in the flight-of-time mass spectrometer 21. In the ion acceleration unit 38, a pulsed high voltage is applied to the thus introduced gaseous ion at a certain timing in order to accelerate the gaseous ion until it has a certain kinetic energy. The thus accelerated gaseous ion has its trajectory altered by the reflector 39 before being detected by the detector 40. The output of the detector 40 is fed to the information processing unit (data processing unit 15) where the m/z of the ion is determined based on the ion detection time. In this way, the secondary mass spectroscopy is realized. A certain number of the prioritized secondary mass spectroscopy target ions are subjected to the secondary mass spectroscopy in accordance with the priority order.

Figure 44:
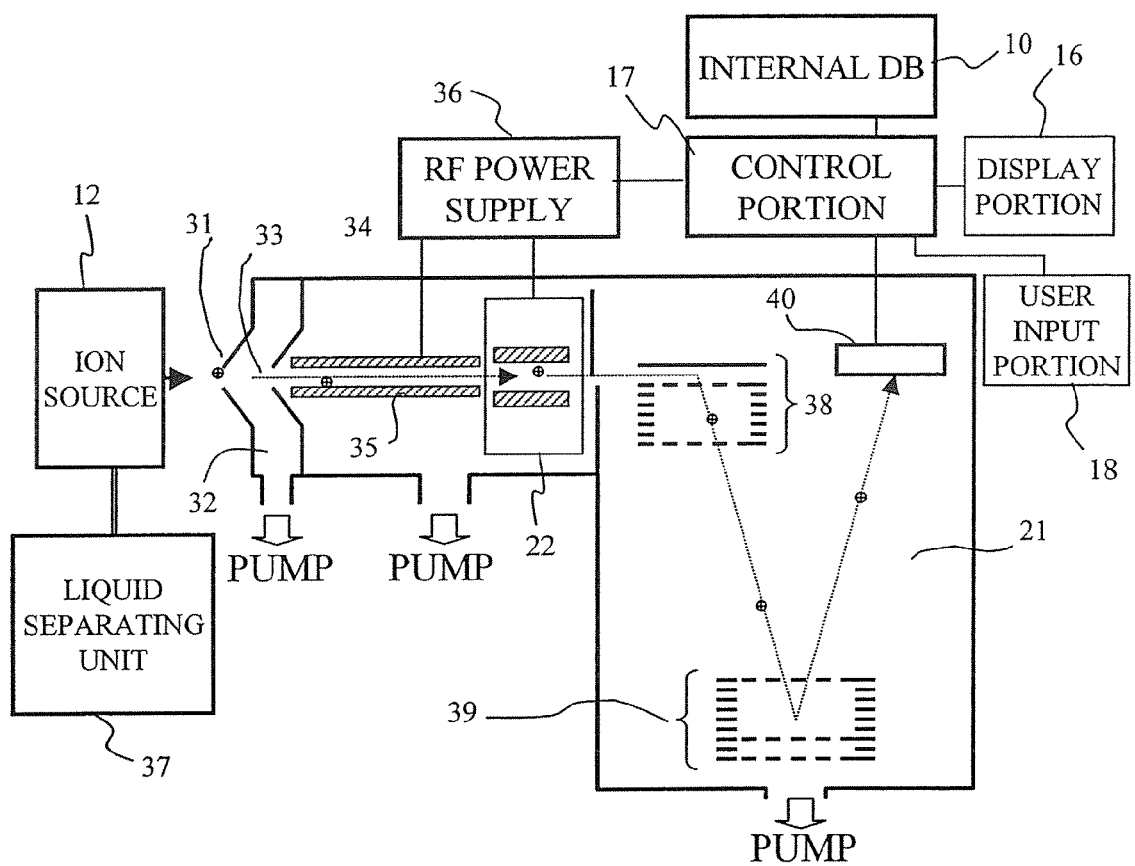
FIG. 44 shows an example of apparatus configuration in the first embodiment of the invention.

Alternatively, the ion trap 20 may employ a linear trap 22 consisting of a quadrupole, as shown in FIG. 44, instead of the quadrupole ion trap. As compared with the quadrupole ion trap, the linear trap has equivalent functionality and is capable of trapping a greater amount of ions at once. To the linear trap, a radio-frequency voltage is applied such that non-analysis target ions can be removed and analysis target ions can be trapped.

Figure 45:
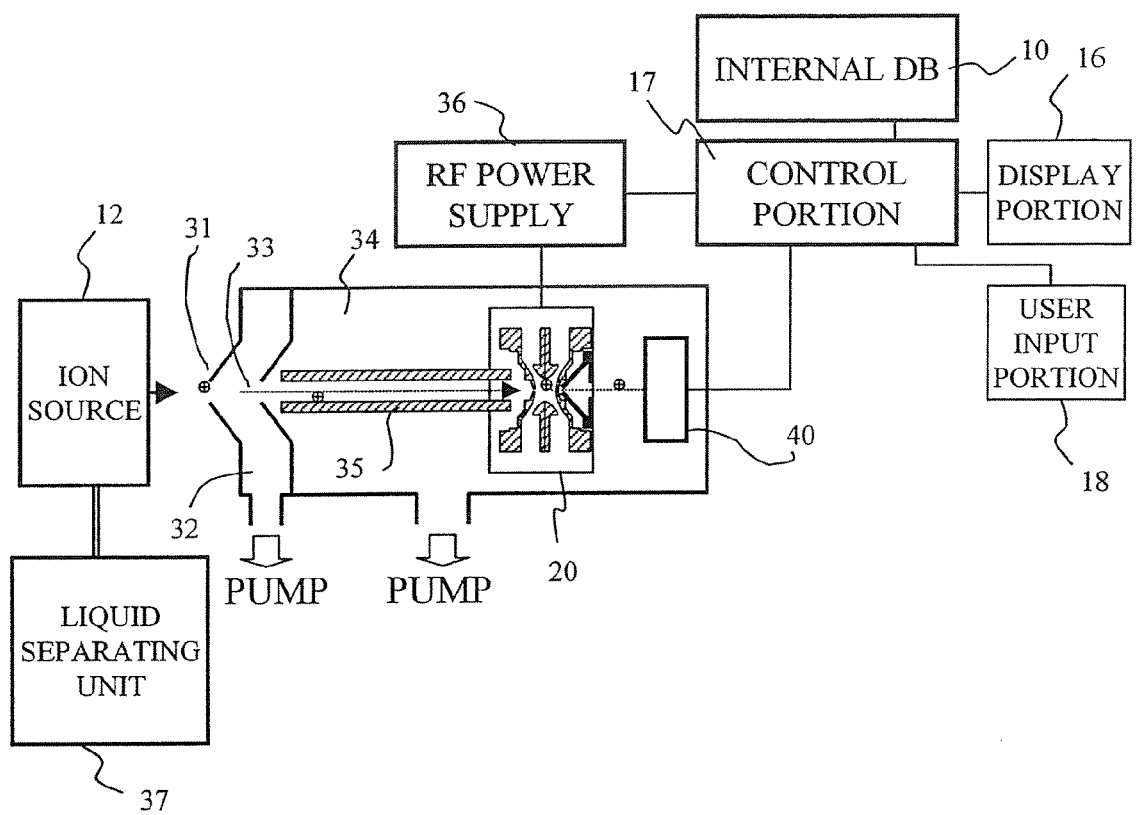
FIG. 45 shows an example of apparatus configuration in the first embodiment of the invention.

Further alternatively, it is also possible to construct the mass spectrometer with only a quadrupole ion trap mass spectrometer, as shown in FIG. 45. A sample solution separated in the liquid separating unit 37 employing a liquid chromatograph, for example, is introduced into the ion source 12 where it is converted into a gaseous ion. The thus produced gaseous ion is introduced into the differential pump unit 32 via the pore 31. The gaseous ion is further passed through, via the pore 33, the ion transportation unit 35 installed in the high-vacuum unit 34, and is then introduced into the ion trap 20. A radio-frequency voltage is supplied from the radio-frequency power supply to the ion trap 20 so that the gaseous ion can be trapped at the center of the ion trap 20. To the ion trap 20, a radio-frequency voltage is applied such that the non-analysis target ions can be removed while trapping the target ions. The gaseous ion that has been trapped for a certain period of time is then discharged from the ion trap 20 depending on the m/z of the ions, as the radio-frequency voltage applied to the ion trap 20 is continuously varied. The discharged ions are detected by the detector 40. The output of which is then fed to the information processing unit where the m/z of the ions can be determined based on the ion detection time (primary mass spectroscopy). The secondary mass spectroscopy may also be performed. As compared with the flight-of-time mass spectrometer, although the quadrupole ion trap is inferior in terms of the range of mass spectroscopy, the mass resolving power, and mass accuracy, it can reduce the size of the apparatus and allows for analysis with higher sensitivity.

In the embodiments shown in FIGS. 43, 44, and 45, a radio-frequency voltage is applied from the radio-frequency power supply in response to an instruction from the information processing unit, whereby the non-analysis target ions are removed prior to the primary mass spectroscopy and the minor components of interest can be reliably subjected to mass spectroscopy. When the linear trap shown in FIG. 44 is used, in particular, since the volume that can be trapped by the linear trap is greater than that by the quadrupole ion trap, for example, by approximately a factor of 8 to two orders of magnitude, the linear trap can more reliably subject the minor components to mass spectroscopy.

The retention time $\tau$ of LC might fluctuate from one measurement to another. Therefore, one or more kinds of reference substance that is already stored in the internal database may be put in the sample, and then the retention time of that reference substance may be compared with an actually measured retention time of the reference substance in order to obtain a difference $\Delta\tau$. Then, the retention time of other ion species may be automatically corrected or calibrated for each measurement using the difference $\Delta\tau$. In this way, even when the retention time $\tau$ of LC fluctuates from one measurement to another, the target ion species for the next tandem analysis $MS^n$ ($n \geq 2$) can be stably selected by utilizing the retention time stored in the internal database.

There are cases where, in the mass-to-charge ratio m/z value, the mass axis (the value of mass-to-charge ratio; m/z) fluctuates as time elapses from the start of measurement. In order to avoid this, one or more kinds of reference substance of which the m/z value is known may be put in the sample and, when there is more than one reference substance, reference substances with different retention times of LC and GC may be selected. Then, the actually measured value of m/z of the reference substances and the known m/z value can be compared so that the m/z value that fluctuates as time elapses after the start of measurement can be automatically corrected or calibrated. In this case, as the m/z value is automatically corrected, it becomes possible to stop the listing of pseudo-positive reaction sequences when, for example, identifying peptides or proteins from the result of measurement of MS data. This function, however, may be performed in a post-processing step after all the measurements have been made.

When the ion species that has only been subjected to the tandem mass spectroscopy with n=1, namely $MS^1$, is to be turned into a target for the $MS^2$ analysis in the subsequent measurements, the ion species is not registered in the internal database 10. Namely, the ion species that are to be stored in the internal database 10 are those ion species that have been subjected to the tandem analysis $MS^n$ ($n \geq 2$). In this case, if the substance names or structures are known, these information are also stored in the internal database 10. Upon determination that, with regard to a peptide, a modification structure is attached, information concerning the type of the structure and the location where it is added (the amino acid to which the modification structure was attached in an amino acid sequence) may also be stored in the internal database 10. With regard to a peptide derived from a protein that has once been measured and identified, characteristics data, such as the amino acid sequence of the peptide, the name of the original protein, mass number m, valence z, the mass-to-charge ratio m/z, retention time τ of LC, ion intensity, analysis conditions, and so on, are stored in the internal database 10. These data are automatically stored in the internal database either during or after measurement. Desirably, the storing of these data in the internal database 10 should be performed as needed within the real time of measurement. However, the storing process does not have to be performed within the real time of measurement when the amount to be processed is large, such as when the derivation of peptides originating from proteins is involved.

In the above-described embodiments, the characteristics data of the ion species that should not be subjected to tandem mass spectroscopy is stored in the internal database 10 while removing those ion species that corresponded to the stored data in the internal database 10 from the targets of tandem mass spectroscopy. Alternatively, however, the characteristics data of the ion species that are desired to be subjected to tandem mass spectroscopy may be stored in the internal database 10, and the ion species that corresponded to the stored data in the internal database 10 may be selected as the target of tandem mass spectroscopy.

Figure 6:
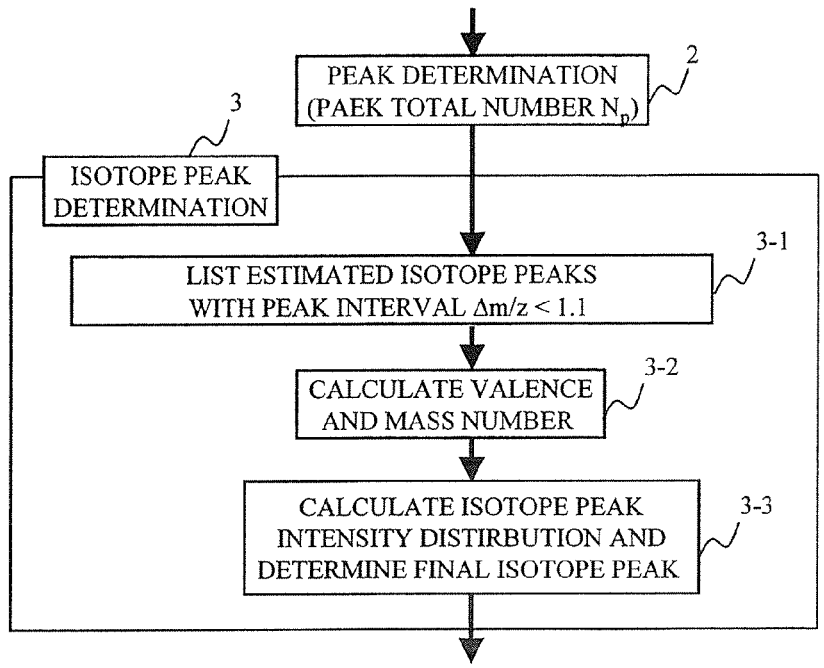
FIG. 6 schematically shows the content of an isotope peak determination process.
Figure 7:
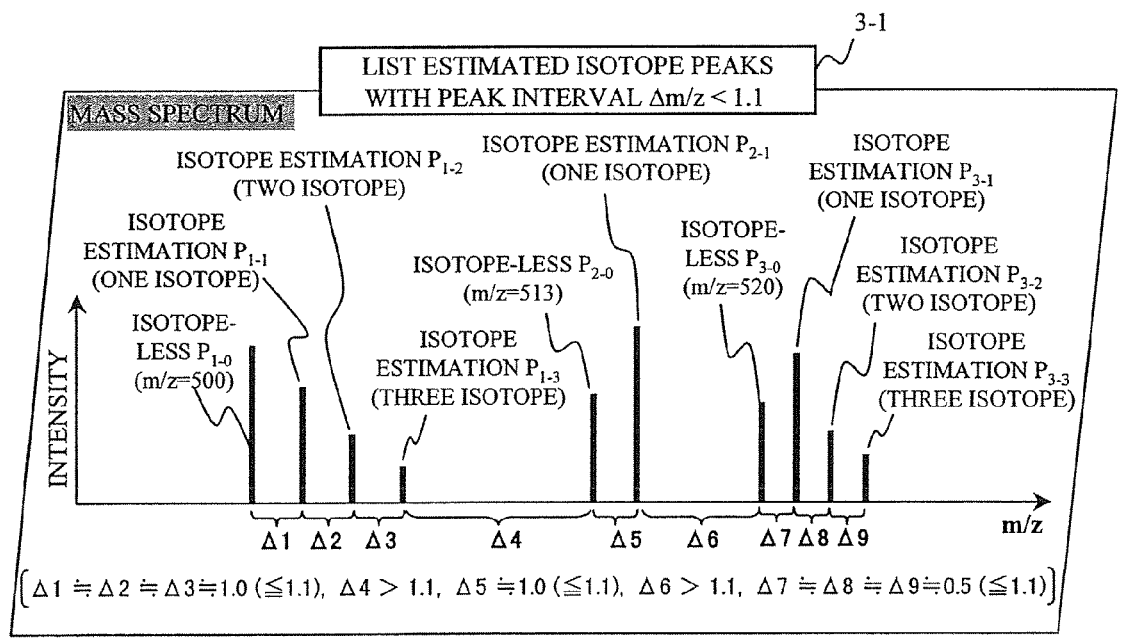
FIG. 7 schematically shows an estimated isotope listing process in the isotope peak determination process.

In order to refer to the mass number m of the ion species, instead of the mass-to-charge ratio m/z value thereof, as the characteristics data of the ion species designated prior to or during measurement, in a characterizing feature of the invention, it is necessary to analyze the measurement data obtained in the preparation time between the acquisition of the MS spectrum data and the next analysis, or during the transition time (such as within 100 msec, 10 msec, 5 msec, or 1 msec). As the mass spectroscopy data (MS$^n$)1 represents the ion intensity with respect to the value of the mass-to-charge ratio m/z, the obtained measurement data is the mass-to-charge ratio m/z. Referring to FIG. 1, in order to derive the mass number m of an ion species from the mass-to-charge ratio m/z in the present embodiment, a peak determination 2 is carried out on a mass spectrum. Then, on a number Np of peaks that have been identified as such, an isotope peak determination 3 is conducted. FIG. 6 shows the content of processing in the isotope peak determination 3. First, on the peak spectrum data (x=m/z, y=intensity), processes including an enumeration 3-1 of isotope estimation peaks, a calculation 3-2 of the valence and mass number of each ion peak, a calculation of isotope peak intensity distribution and determination 3-3 of final isotope peaks are carried out. The content of the enumeration 3-1 of the isotope estimation peaks is such that it is determined that, when the interval $\Delta(m/z)_i = x_{i+1} - x_i$ between a peak i $(x_i, y_i)$ and a peak i+1 $(x_{i+1}(>x_i), y_{i+1})$ is such that $\Delta(m/z)_i < 1.1$, it is estimated that the peak could possibly an isotope peak that contains one more isotopes than peak i, and if $\Delta(m/z)i \geq 1.1$, it is estimated that the peak i+1 is a peak that does not contain an isotope with respect to the peak i. An example of the enumeration 3-1 of isotope estimation peaks is shown in FIG. 7. With respect to the peak $P_{1-0}$, three peaks $P_{1-1}$, $P_{1-2}$, and $P_{1-3}$ which are spaced apart from one another by $\Delta m/z = 1.0$ are estimated to be isotope peaks. Similarly, it is estimated that $P_{2-1}$ is an isotope peak with respect to the peak $P_{2-0}$ and $P_{3-1}$, $P_{3-2}$, and $P_{3-3}$ are isotope peaks with respect to the peak $P_{3-0}$. Next, the calculation 3-2 of the valence and mass number of each ion peak will be described with reference to FIG. 8. In cases where the sample is a peptide or protein, the constituent elements are limited to C, O, N, H, and S. When the natural abundance of these elements and the number of these elements included within a peptide are considered, the number of isotopes of carbon C is large. The difference in mass number between $C^{12}$ and its isotope $C^{13}$ is 1.003354, or approximately 1.0 Da. Thus, in the case where peak i+1 is estimated to be an isotope peak of peak i, the valence z of the ion species can be determined from the measured interval $(\Delta(m/z)_i \approx 1.0$ Da/z) between peak i$(x_i, y_i)$ and peak i+1$(x_{i+1}(>x_i), y_{i+1})$ (Equation (1)). In this case, since $1/\Delta(m/z)$ is not necessarily an integer, a rounding process is carried out to ensure it is an integer. When the mass number of the ion in a neutral state is $m_p$, the mass number is the mass number $m_p$ in a neutral state to which the mass number of a proton ion (valence×mass number mH) is added (Equation (2)).

$$z = 1/\Delta(m/z) \quad (1)$$

$$m/z = (m_p + z \times mH)/z \quad (2)$$

Figure 8:
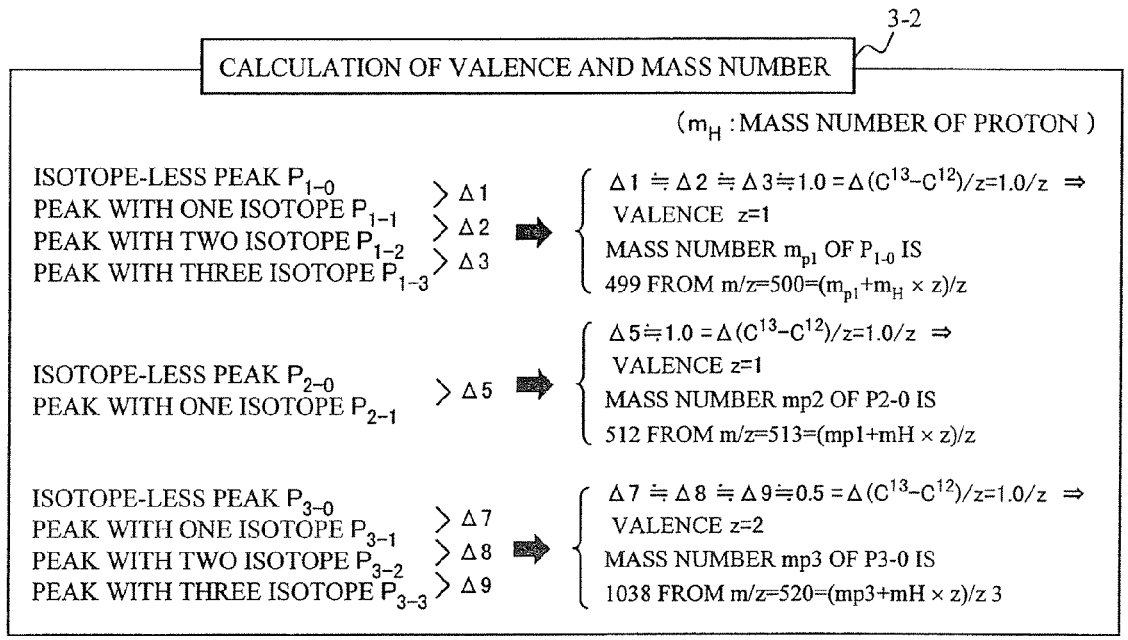
FIG. 8 schematically shows the process of calculation of valence and mass number in the isotope peak determination process.

Thus, from Equations (1) and (2), the valence and mass number $m_p$ in a neutral state of each ion peak can be determined. In the example shown in FIG. 7, the valence z of ion peak $P_{1-0}$ is 1 and mass number m=499 where m/z=500 Da, as shown in FIG. 8, the valence z of ion peak $P_{2-0}$ is 1 mass number m=512 Da where and m/z=513, and the valence z of ion peak $P_{3-0}$ is 2 and mass number m=1038 Da where m/z=520. The mass number and valence of each ion peak may be determined by the above-described isotope peak determination method. Provided that the intensity of the ion peak is sufficiently high (such as when the intensity$\geq 1000$), more detailed determination may be performed based on the intensity distribution of the peaks without isotopes and the isotope peaks, as will be described below.

Figure 9A:
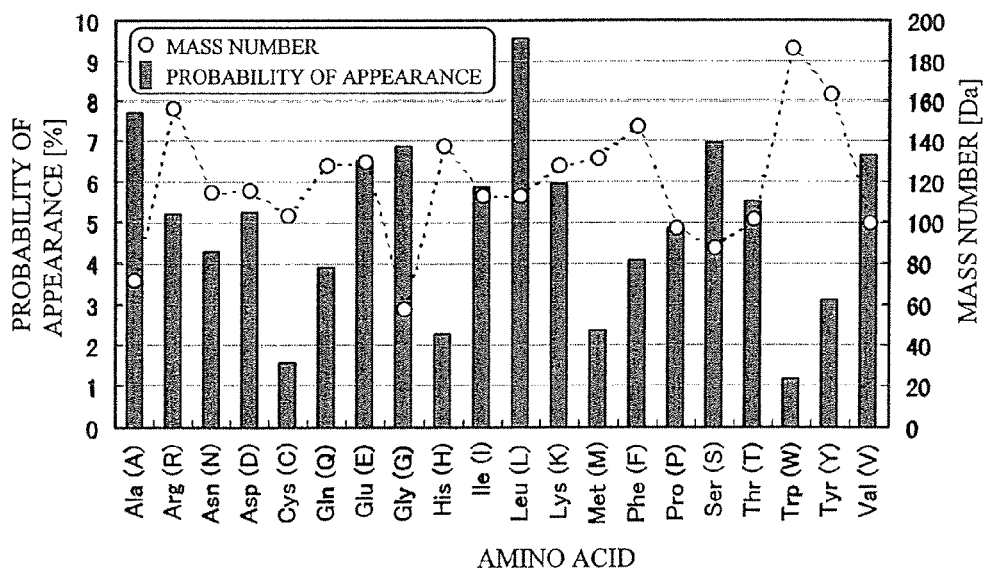
FIG. 9A shows the probability of appearance of 20 types of amino acids in a living body, and the mass number of peptide chains.
Figure 9:
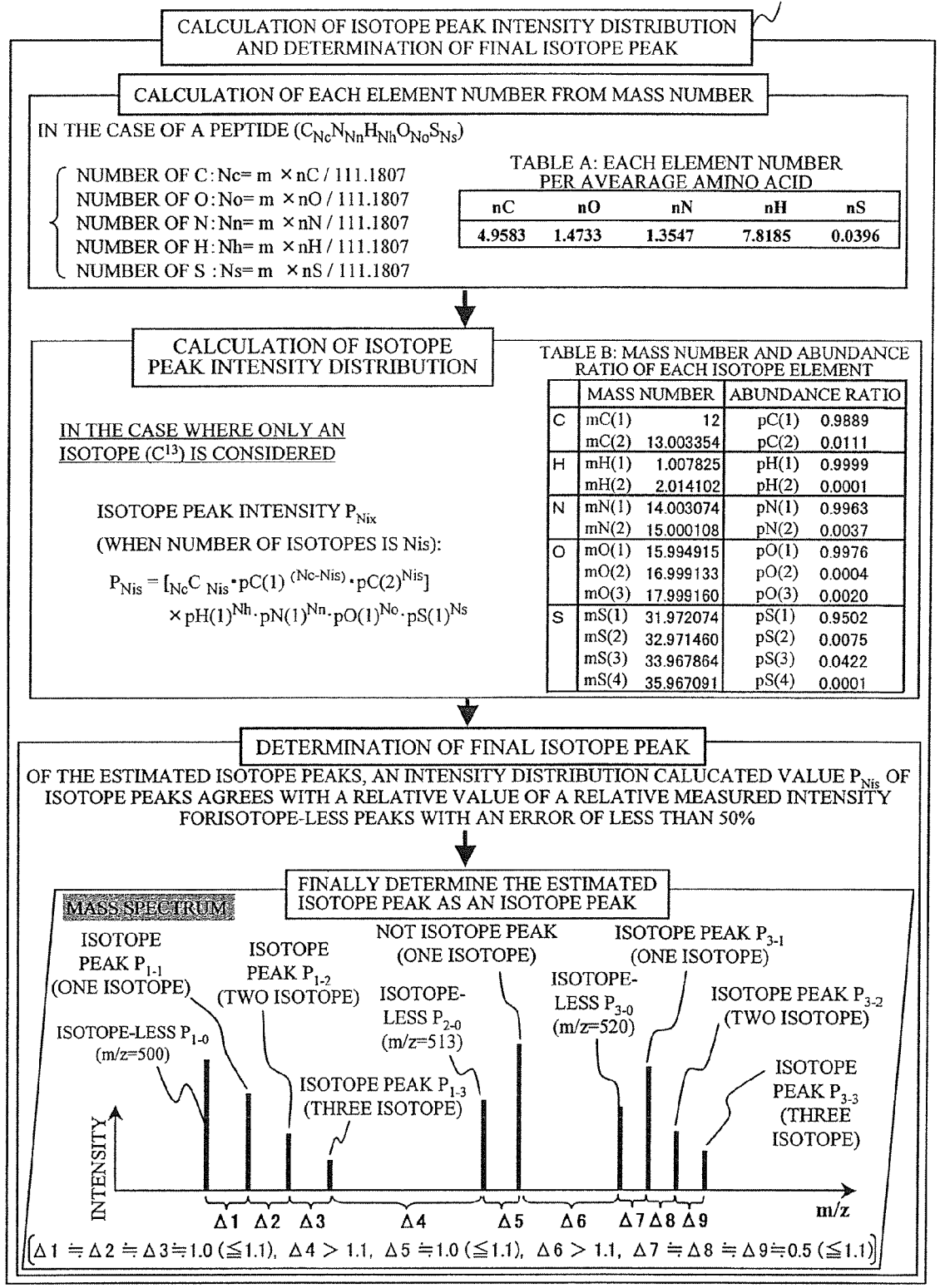
FIG. 9B shows the calculation of an isotope peak intensity distribution and the process of determining a final isotope peak in the isotope peak determination process of the invention.
Figure 10:
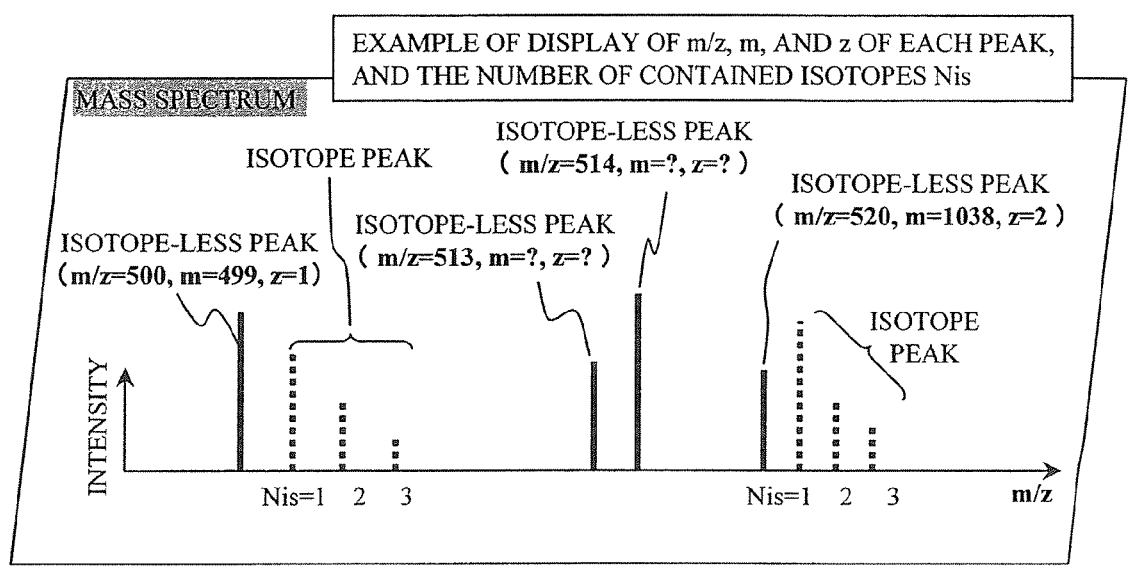
FIG. 10 shows an example of display of the m/z, m, and z of each peak and the number of contained isotopes in the result of the isotope peak determination process of the invention.
Figure 15:
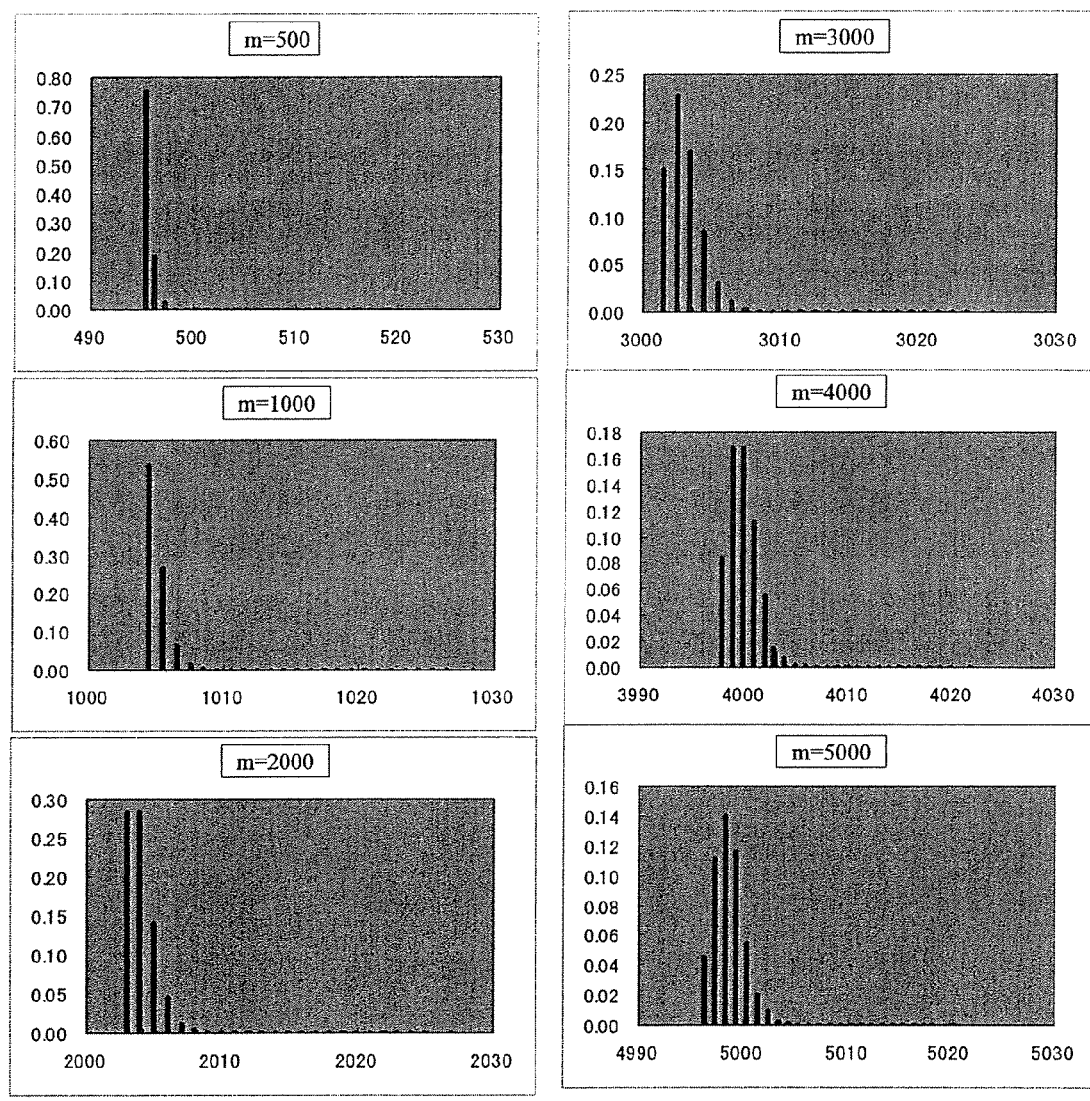
FIG. 15 shows an intensity distribution pattern of isotope peaks depending on the mass number.

The content of processing in the calculation of isotope peak intensity distribution and determination of the final isotope peak 3-3 will be described with reference to FIGS. 9A and 9B. For example, when the sample is an amino acid sequence such as a protein or a peptide, the constituent elements of an amino acid is limited to C, O, N, H, and S. FIG. 9A shows the probability of appearance of each of the 20 amino acids derived from a protein database (Swiss Prot), and the mass number of each amino acid. The mass number of amino acid, however, refers to the mass number of the amino acid (—NH—CR$^0$—CO—) in a peptide sequence, where R$^0$ is a remaining sequence which differs depending on the type of amino acid. From these items of data, the average mass number (111.1807 Da) of the amino acid and the average values nC, nO, nN, nH, and nS of each of the constituent element numbers of the amino acid are determined, as shown in Table A in FIG. 9B. Specifically, assuming that the protein or peptide is made up of an average amino acid with the mass number 111.1807 Da as shown in Table A, approximate numbers Nc, No, Nn, Nh, and Ns of the constituent element numbers of C, O, N, H, and S are determined from the mass number m of the protein or peptide. Then, the intensity distribution of the isotope peaks is derived. Table B shows the abundance ratio of each isotope element. Of these isotope elements, the element with the largest abundance ratio is $C^{13}$. Thus, when only the isotope $C^{13}$ is to be considered, the isotope peak intensity for the case where the number of included isotopes Nis can be calculated from the following equation:

$$P_{Nis} = [_{Nc}C_{Nis} \cdot pC(1)^{(Nc-Nis)} \cdot pC(2)_{Nis}] \times pH(1)^{Nh} \cdot pN(1)_{Nn} \cdot pO(1)^{No} \cdot pS(1)^{Ns} \quad (3)$$

where pC(1), pC(2), pH(1), pN(1), pO(1), and pS(1) indicate the abundance ratios in Table B. FIG. 15 shows an example of the calculation of the intensity distribution of the isotope peaks in accordance with the mass number using Equation (3). The intensity distribution of the isotope peaks determined from the mass number m calculated in step 3-2 is then compared with the intensity distribution of the isotope peaks estimated in step 3-1. If the intensity ratio of the estimated isotope peaks to the isotope-less peaks corresponds with a less than 50% error, the estimated isotope peaks are finally determined to be isotope peaks. If, on the other hand, the intensity ratio of the estimated isotope peaks to the isotope-less peaks differs by 50% or more, the estimated isotope peaks are not determined to be the isotope peaks. In the example shown in FIG. 7, the intensity distribution of the isotope peaks is considered. Of the estimated isotope peaks, $P_{2\text{-}0}$ where m/z=513 and the estimated isotope peak $P_{2\text{-}1}$, which is displaced by $\Delta(m/z)=1.0$ and with a higher intensity than that of $P_{2\text{-}0}$, are finally determined to be not isotope peaks, as shown in FIG. 9B. The data obtained in this isotope peak determination process 3, namely the valence z of each ion peak, the mass number m in a neutral state, whether the peak is an isotope peak or not, and the number of included isotopes Nis, can be outputted in the form of a file or displayed on the display unit 16 along with the display of the spectrum, as shown in FIG. 10. The aforementioned information is very useful to the user when determining the target for the tandem mass spectroscopy or analyzing the spectrum data at the end of measurement.

In the present embodiment, $MS^{n+1}$ is adopted as the next tandem mass spectroscopy wherein a parent ion is selected from the $MS^n$ ion peaks and is then subjected to dissociation and mass spectroscopy. A determination 5 is made as to the presence or absence of any parent ion target candidate. If there is a parent ion target candidate, the parent ion for the next $MS^{n+1}$ is determined in a $MS^{n+1}$ analysis content determination 7. In order to allow the parent ion to be selected and dissociated with high efficiency, operating conditions or the like may be altered and optimized. If there is no parent ion target candidate, a next sample analysis ($MS^1$) is performed or the measurement comes to an end. At this point in time, the next analysis content (a target ion or the like, in the case of the tandem mass spectroscopy $MS^n$ where $n \geq 2$) that has been automatically determined by the invention is displayed by the display unit 16. If necessary, an interface may be provided that allows the user to acknowledge the next analysis content being displayed, such that the analysis of the next analysis content that has actually been automatically determined can be conducted after receiving the user's acknowledgement.

Figure 11:
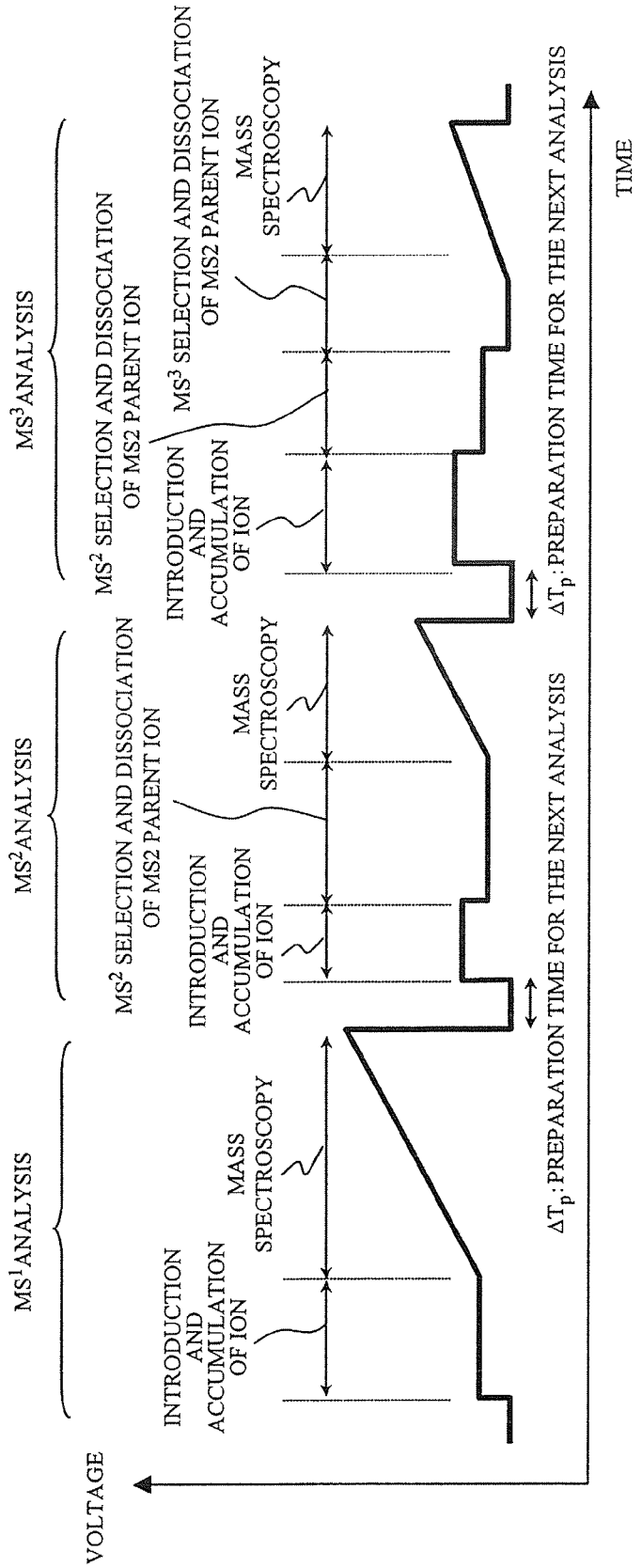
FIG. 11 shows an example of the timings of carrying out the processes shown in FIGS. 1, 12, 13, 14, and 20 according to the invention within the real time of mass spectroscopy measurement.

Furthermore, the invention is characterized in that the above-described processes are carried out at high speed within the real time of measurement. An example of the real time of measurement will be described with reference to FIG. 11, which shows the operation sequence of the apparatus adapted for tandem mass spectroscopy ($MS^1$, $MS^2$, $MS^3$). According to the invention, analysis conditions such as the voltage applied to the mass spectroscopy system, the time of introduction of ion, the duration of time of storage of ion, and so on, are automatically changed or adjusted, depending on the target ion species for $MS^2$ or $MS^3$ that has been automatically determined. When transitioning from $MS^1$ to $MS^2$, and from $MS^2$ to $MS^3$, a series of processes shown in FIG. 1 are carried out within the preparation time or transition time $\Delta Tp$ (such as 100 msec, 10 msec, 5 msec, or 1 msec) between the acquisition of the MS spectrum data and the next analysis. For such high-speed processes, a cache memory or hard disc may be allocated for the storage of necessary data. Moreover, the information processing unit may comprise a plurality of information processing units, such as parallel computers or cluster computers, if necessary. In this case, the single internal database 10 may be divided so that the search process can be performed in each portion of the internal database in a parallel manner. Alternatively, in the case where a plurality of databases are provided as the search databases separately from the internal database 10, the search process may be performed in parallel in each database. The stored data in the internal database 10 is basically stored in a hard disc, and when the internal database 10 is used, the content of the internal database on the hard disc is written into a memory. In this case, the content of the internal database on the hard disc may be written into the memory regularly at certain time intervals. Prior to measurement, the content of the internal database is written from the hard disc to the memory, and any content of the internal database that has been added or modified during measurement is added or modified and then stored in the memory. The content of the internal database may be stored in the hard disc after the end of measurement. While accessing the hard disc may take some time, by transferring the content of the internal database to the memory and then accessing the memory, the search of the internal database can be performed during measurement.

When subjecting the sample to mass spectroscopy using LC-MS on the system of the invention, a mass spectroscopy measurement process in which the sample as the target of analysis is divided into a number n portions ($n \geq 2$), and mass spectroscopy is conducted during the time of LC between the start of elution and the complete elution of the divided sample portions, may be repeated n times, n being the number of portions into which the sample was divided. In this case, when n=1, high-intensity ion species are sequentially subjected to the $MS^n$ analysis ($n \geq 2$), and their characteristics data are stored in the internal database. Thus, the high-intensity ion species are already stored in the internal database when n=2 and thereafter, the other ion species, such as low-intensity ion species, that have not been subjected to the tandem analysis ($MS^n$ analysis (($n \geq 2$)) can become the target of the $MS^n$ analysis ($n \geq 2$). Accordingly, an increase can be expected in the number of proteins identified from the final result of the measurement process that is repeated n times.

Thus, in accordance with the present embodiment, the spectrum of $MS^n$ is analyzed at high speed within the real time of measurement, and it is then determined whether or not the ion species is the target of the next tandem mass spectroscopy $MS^{n+1}$ in real time and with high accuracy, so that even minute amounts of ion peaks, as shown in FIG. 3B, can be subjected to tandem mass spectroscopy.

Figure 12:
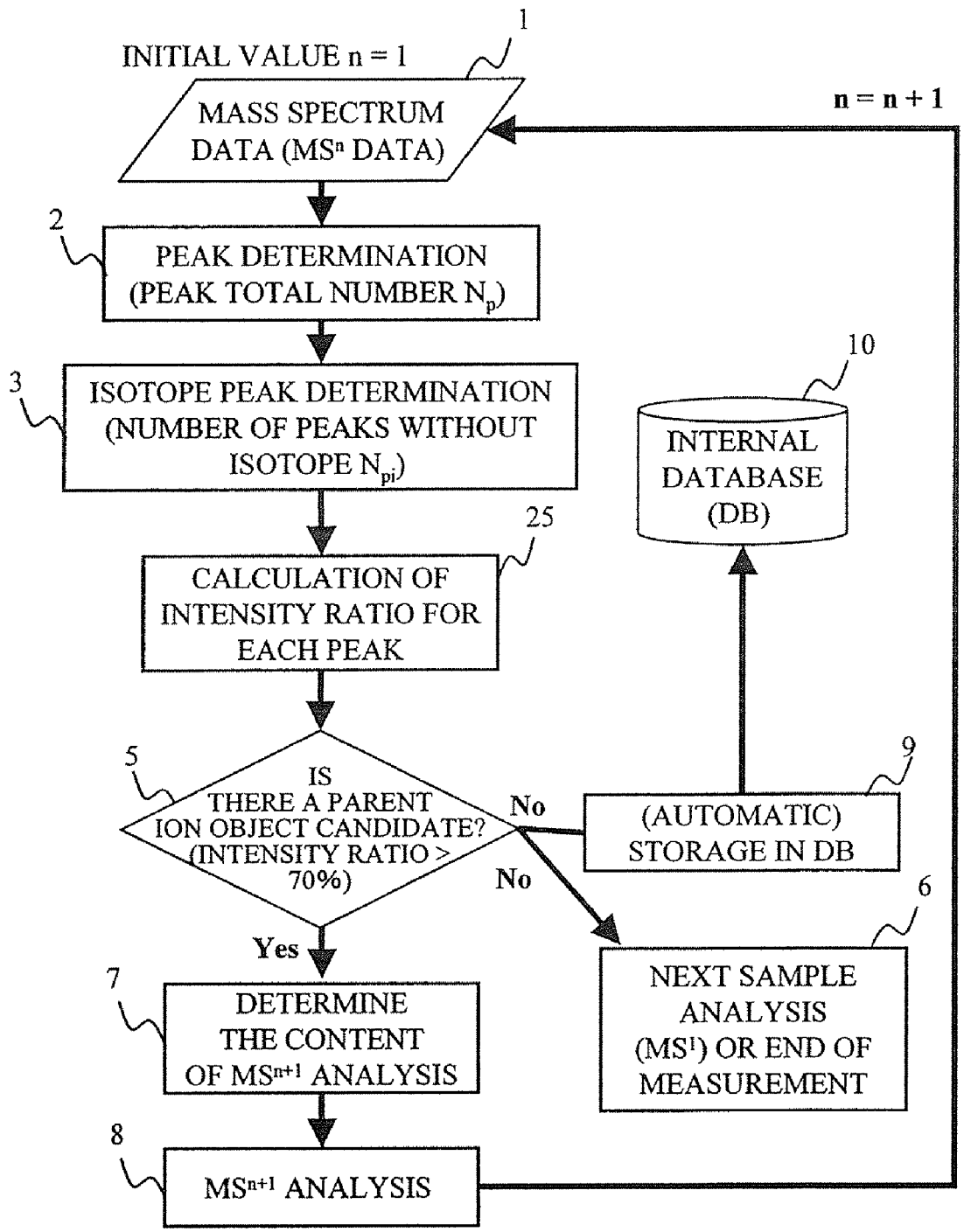
FIG. 12 schematically shows an automatic determination process in the mass spectroscopy flow according to a second embodiment of the invention.

Now with reference to FIG. 12, a second embodiment of the invention is described. In this embodiment, the analysis is limited to minute amounts of peptide and, instead of the collation process 4 with the internal database that is performed in the first embodiment, the intensity ratio of each of the ion peaks in the $MS^n$ spectrum to the peak with the maximum intensity is calculated. The peaks with the intensity ratios of less than 70%, for example, are listed, and the targets for the next tandem mass spectroscopy $MS^{n+1}$ are determined in real time. It is desirable, however, to carry out the isotope peak determination in this embodiment too, in order to eliminate, among the relevant peaks, the isotope peaks from the targets for the next tandem mass spectroscopy $MS^{n+1}$. The intensity ratio with the peak with the maximum intensity may be entered by the user. In this case, there is no need to carry out the collation process 4 with the internal database, so that minute amounts of ion peaks can be determined within the real time of measurement without fail, thereby making it possible to subject minute amounts of ion peaks to tandem mass spectroscopy.

Figure 13:
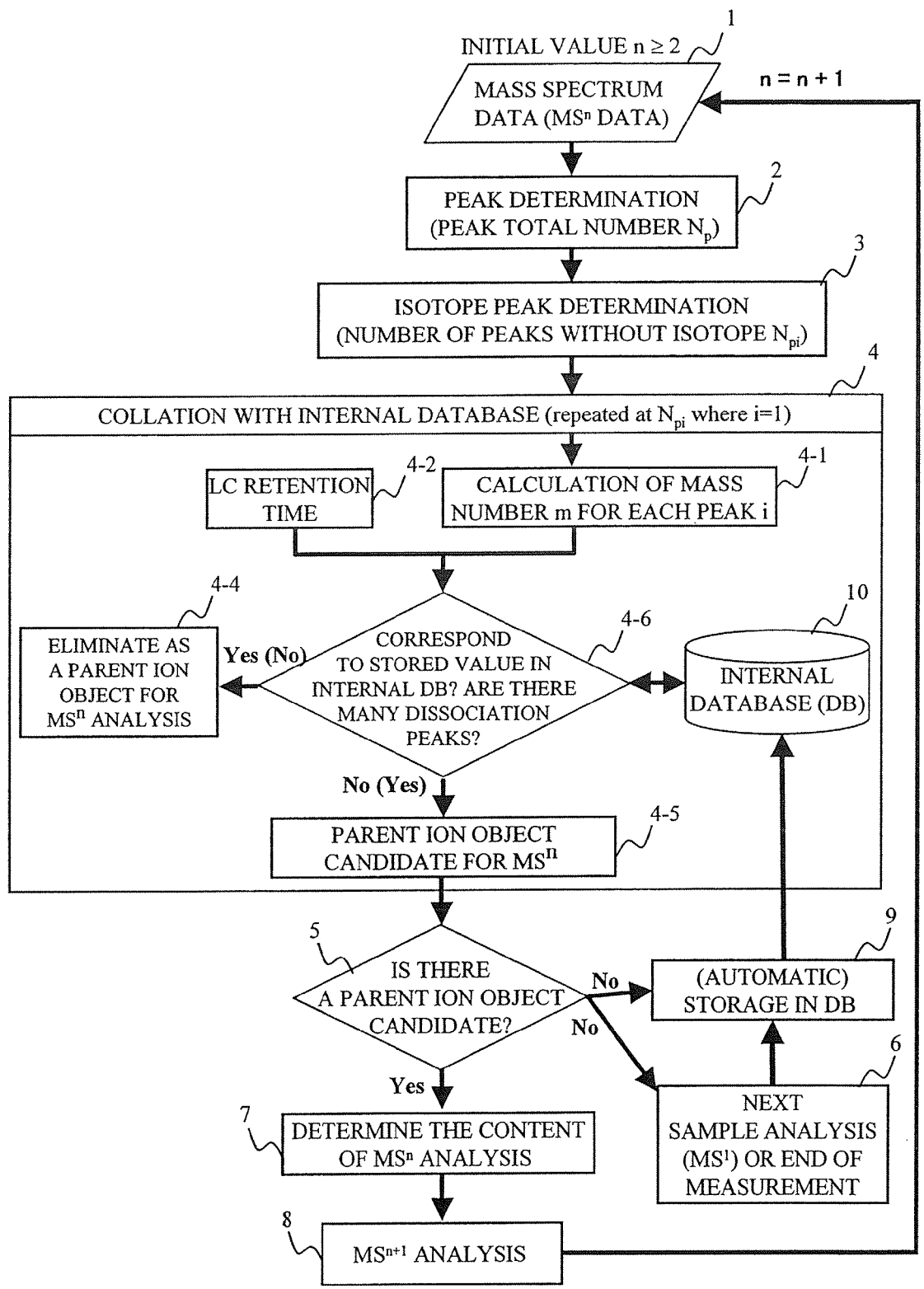
FIG. 13 schematically shows an automatic determination process in the mass spectroscopy flow according to a third embodiment of the invention.

With reference to FIGS. 3C and 13, a third embodiment of the invention is described. In this embodiment, $MS^n$ is performed again as the next tandem mass spectroscopy, instead of $MS^{n+1}$. Specifically, an ion peak with a different m/z value from that of the parent ion that has been the target during the measurement of the $MS^n$ spectrum is selected from the $MS^{n-1}$ ion peaks, and then $MS^n$ is repeated. This concept is shown in FIG. 3C. For example, in a case where an ion peak with m/z=1000 (m=1000, z=1) is selected as the parent ion in $MS^1$ and, when an $MS^2$ analysis is performed, there is not much dissociation spectrum of $MS^2$ and it is determined that the result is insufficient for the identification of an amino acid sequence, an ion peak with the same mass number of the target and a different valence (m/z=500, (m=1000, z=2)) is selected in $MS^1$ as the parent ion, and $MS^2$ is carried out again. In this case, since the m/z of the parent ion becomes one half, the operation conditions or the like may be changed so as to allow the selection and dissociation of the parent ion to be performed with high efficiency. By thus repeating $MS^2$ on an ion peak with the same mass number of the target and a different valence, more often than not a sufficient number of dissociation peaks for the identification of an amino acid sequence can be obtained. Further, the present embodiment, as a tandem mass spectroscopy function, can be adapted to apparatuses that are equipped only with the $MS^2$ function.

Figure 14:
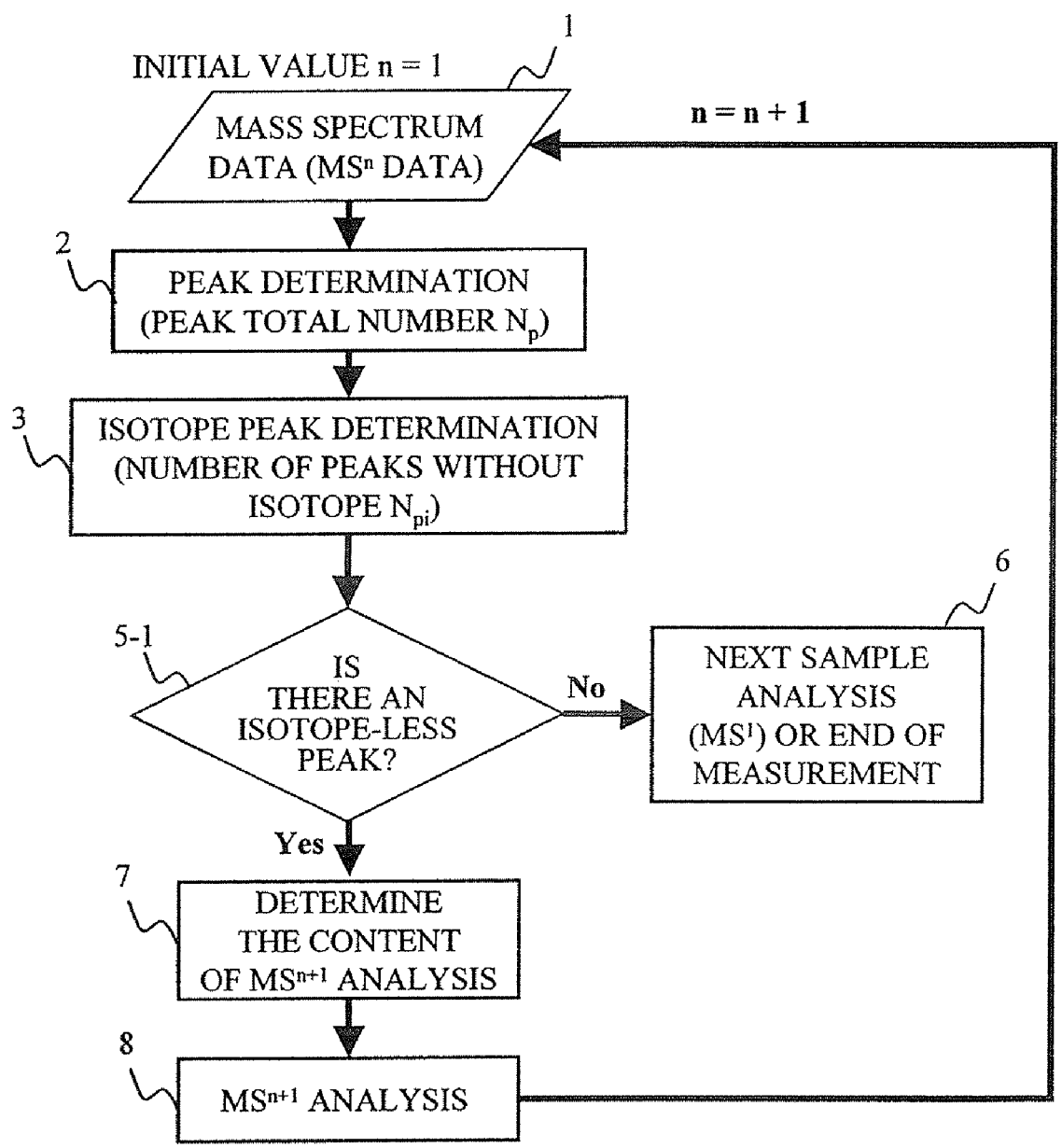
FIG. 14 schematically shows an automatic determination process in the mass spectroscopy flow according to a fourth embodiment of the invention.

Hereafter, a fourth embodiment of the invention will be described with reference to FIG. 14. In this embodiment, the collation process 4 referring to the internal database is not performed, and mainly the determination of the isotope peaks is performed. With regard to the peaks that are determined to be not isotope peaks, the targets for the next tandem mass spectroscopy may be determined in the order of decreasing intensity, as is conventionally done. As shown in FIG. 15, the intensity of isotope peaks becomes greater with increasing mass number. If the peaks are subjected to tandem mass spectroscopy simply in the order of decreasing intensity of the peaks, as is conventionally done, an isotope peak might be erroneously selected as a parent peak. If that happens, the m/z of the mass spectrum is displaced due to the isotope, thereby increasing the likelihood that the result of data analysis exhibits a pseudo-positive reaction. In accordance with the present embodiment, only those peaks without isotopes are selected as the targets of the next tandem mass spectroscopy in the order of decreasing intensity. Thus, the aforementioned problem is avoided.

Figure 16:
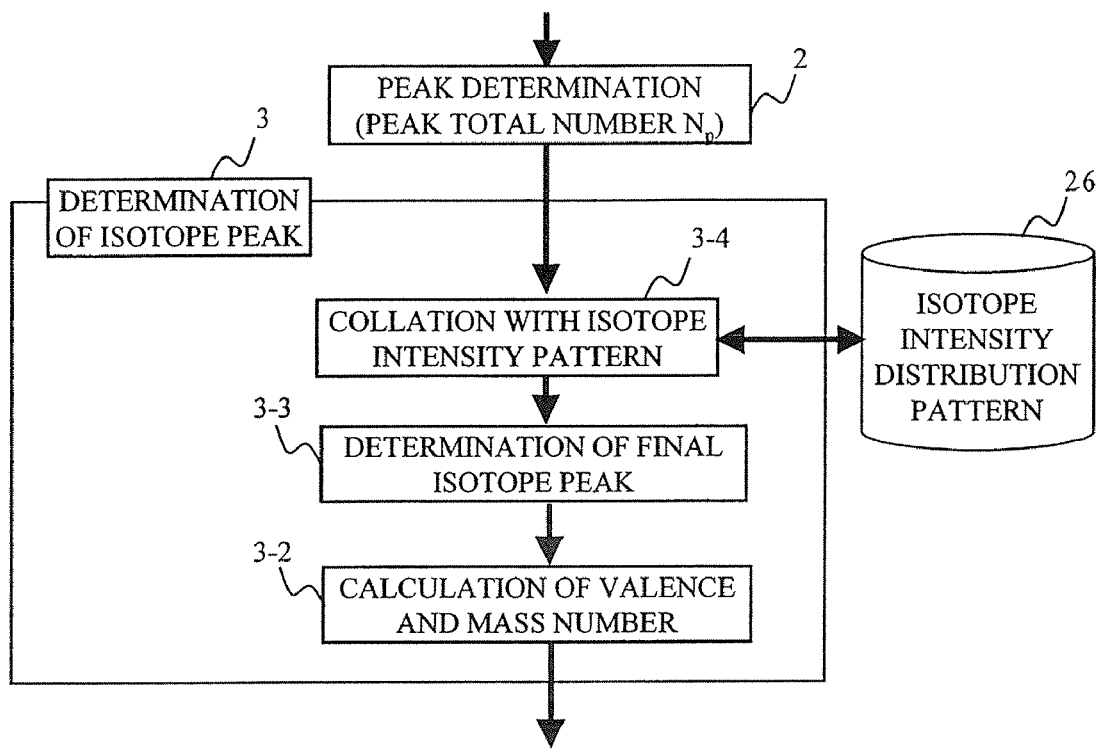
FIG. 16 schematically shows the content of an isotope determination process according to a fifth embodiment of the invention.

Hereafter, a fifth embodiment of the invention will be described with reference to FIGS. 15 and 16. In this embodiment, instead of performing the isotope determination process 3 as shown in FIG. 6, isotope intensity distribution patterns corresponding to mass numbers, as shown in FIG. 15, are stored in advance, and the determination as to whether or not a particular peak is an isotope is made by matching those patterns with actual measurement data. The flow of this process is shown in FIG. 16. In accordance with the present embodiment, only the matching process is carried out without performing the isotope peak intensity distribution calculation in real time, so that it is possible to perform the isotope determination process more reliably in real time.

Figure 17:
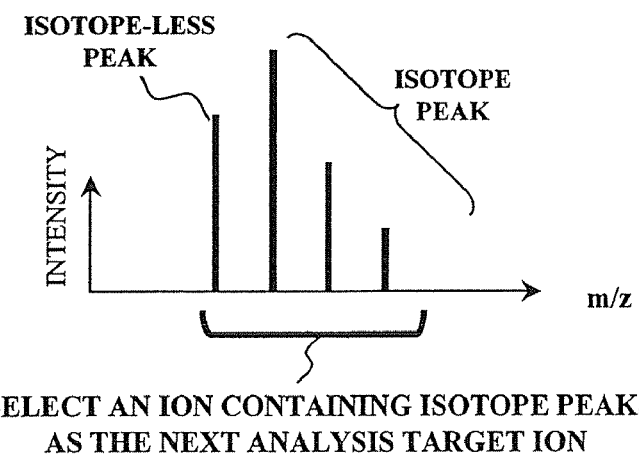
FIG. 17 schematically shows the selection of a parent ion for tandem mass spectroscopy according to a sixth embodiment of the invention.

With reference to FIG. 17, a sixth embodiment of the invention is described. In the embodiments described up to now, when a target ion is selected for the next tandem mass spectroscopy, isotope peaks have been avoided. However, the selection may be made by including isotope peaks. In this case, the analysis conditions are set such that the resolution at which a parent ion is selected decreases in accordance with the range of appearance of isotope peaks. In the present embodiment, dissociation and mass spectroscopy can be performed on isotope peaks as well, in cases where the amount of the parent ion is minute in the first place and the intensity of isotope peaks is stronger, for example, so that the intensity of the dissociation peak can be increased.

Figure 18:
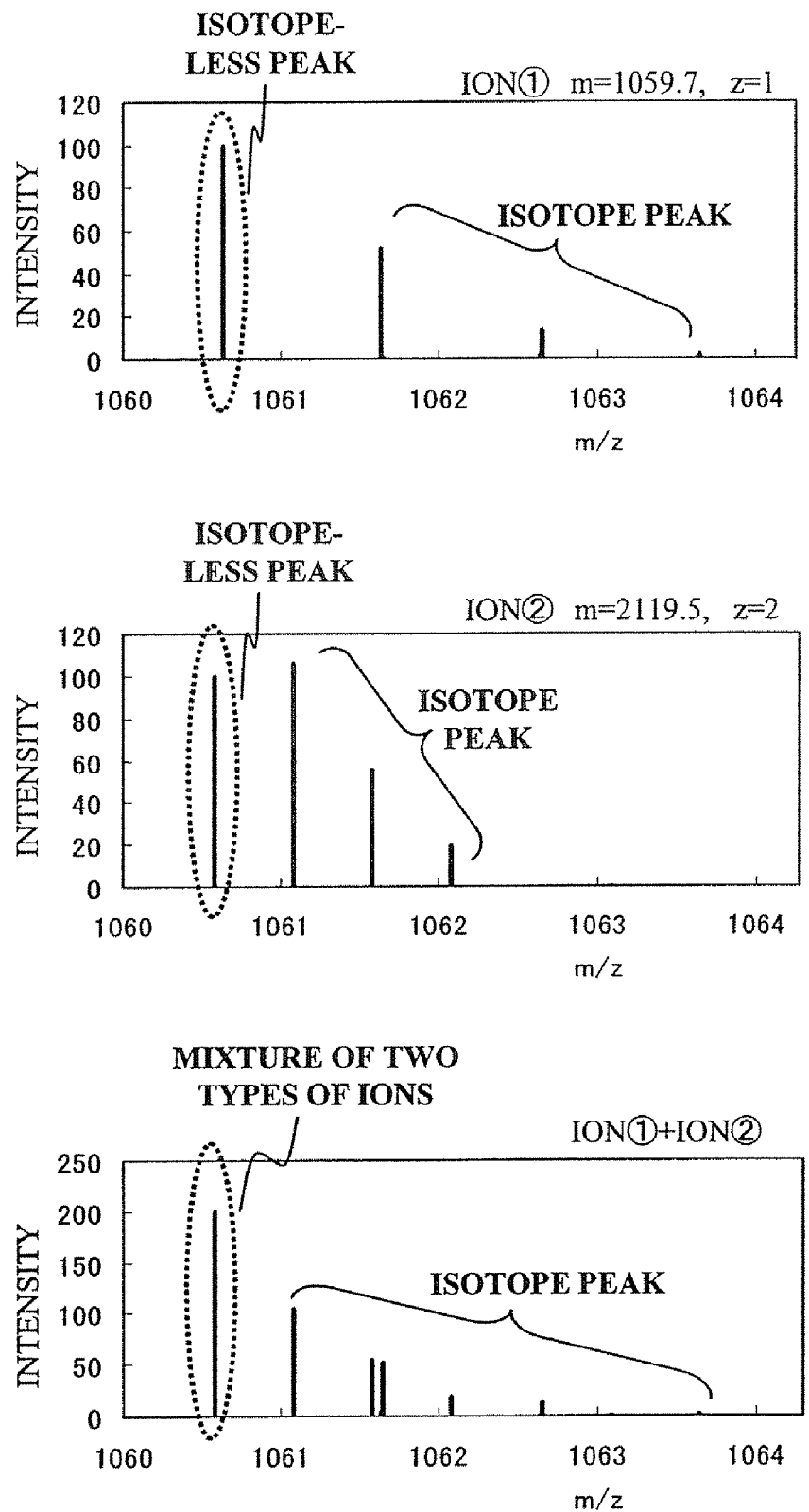
FIG. 18 shows examples of isotope patterns of a plurality of ion species with identical m/z value in a seventh embodiment of the invention.

With reference now to FIG. 18, a seventh embodiment of the invention is described. In this embodiment, in cases where the peaks of ion species with the same or very close m/z values and with different mass number m and valence z are superposed, the superposition of the multiple ion species is determined based on the intensity distribution of isotope peaks, as shown in FIG. 18. Ion (1) is an ion species with m=1059.7 and z=1. Ion (2) is an ion species with m=2119.5 and z=2. The figure shows an isotope-less peak and isotope peaks for each ion species. When these ion peaks exist simultaneously, they are superposed at the isotope-less peak position at m/z=1060.7. If these ion species were subjected to tandem mass spectroscopy, the dissociation peaks of the two kinds of ions would appear, thereby making it difficult to perform data analysis, or resulting the result of data analysis estimating an erroneous amino acid sequence. In accordance with the present embodiment, therefore, on the assumption that there are cases where the m/z of a plurality of ion species is identical, the intensity distributions of their isotope peaks are calculated, and then a distribution is calculated based on the superposition of the distributions, as shown in the third chart of FIG. 18. The superposed distribution is stored, as shown in the fifth embodiment, and by pattern-matching the stored distribution with measured data, it is determined whether or not there is a mixture of a plurality of ion species. When there is a mixture of ion species, their ion peaks are avoided as the targets for the next tandem mass spectroscopy in order to prevent the mixture of the dissociation peaks of two kinds of ions which makes it difficult to perform data analysis. In the case where there is a mixture of a plurality of ion species, when selecting the ion peaks of the multiple ion species as the targets for the next tandem mass spectroscopy, the possibility is displayed and let known to the user. Information (m and z) obtained upon determination of the mixture of a plurality of ion species may be outputted to a file or the like so that it can be used for data analysis after the measurement is over.

Figure 19:
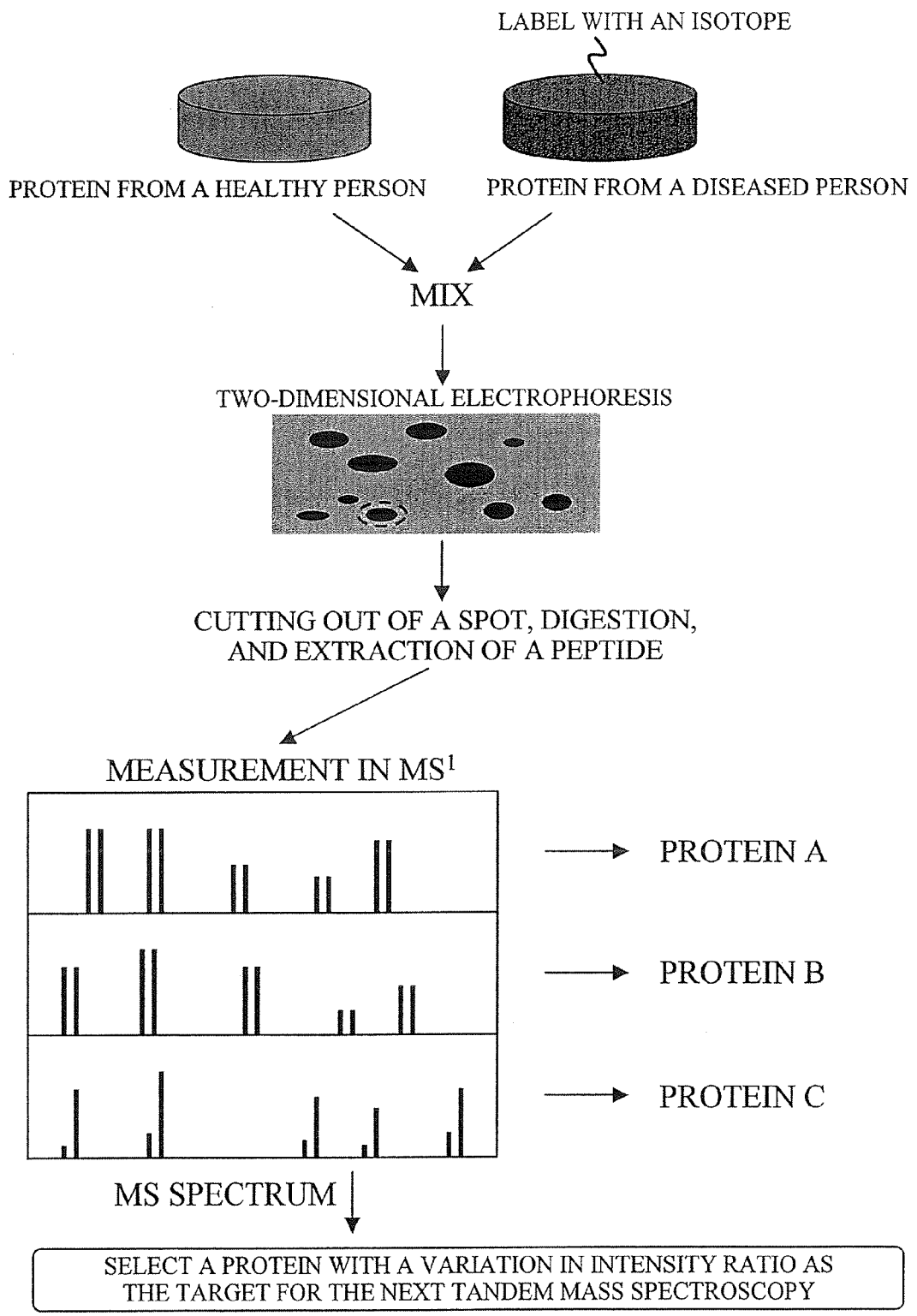
FIG. 19 shows the concept of the selection of the next tandem mass spectroscopy target using isotope labeling in an eighth embodiment of the invention.

With reference to FIG. 19, an eight embodiment of the invention will be described. In this embodiment, when, for example, an expression protein sample from either a healthy subject or a diseased subject is labeled with an isotope in order to compare the difference in expression levels by subjecting the peptides from these proteins to an $MS^1$ analysis, if there is an intensity ratio between them, either the isotope-labeled sample or the sample that has not been labeled is selected as the target for the next tandem mass spectroscopy. In accordance with the present embodiment, a peptide derived from a protein with a pathologic potential can be automatically determined and subjected to a detailed structural analysis.

Now with reference to FIG. 20, a ninth embodiment of the invention will be described. In this embodiment, instead of performing the determination concerning the valence or isotope peaks based on the individual peak intervals in the measured $MS^1$ data, as described in the first embodiment, and without performing the conversion of the m/z value of each peak in the measured $MS^1$ data into mass number m, the mass number m (such as, for example, m=2000) in the internal database is converted into a m/z value by simply dividing it by the valence z (such as, for example, z=1, 2, 3, 4, or 5) within an assumed range. Based on the thus calculated m/z values (such as, for example, m/z=2000, 1000, 666.7, 500, or 400), collation with the internal database is performed. In this case, the processing content becomes much lighter, so that the processes can be reliably performed within the real time of measurement.

Figure 21:
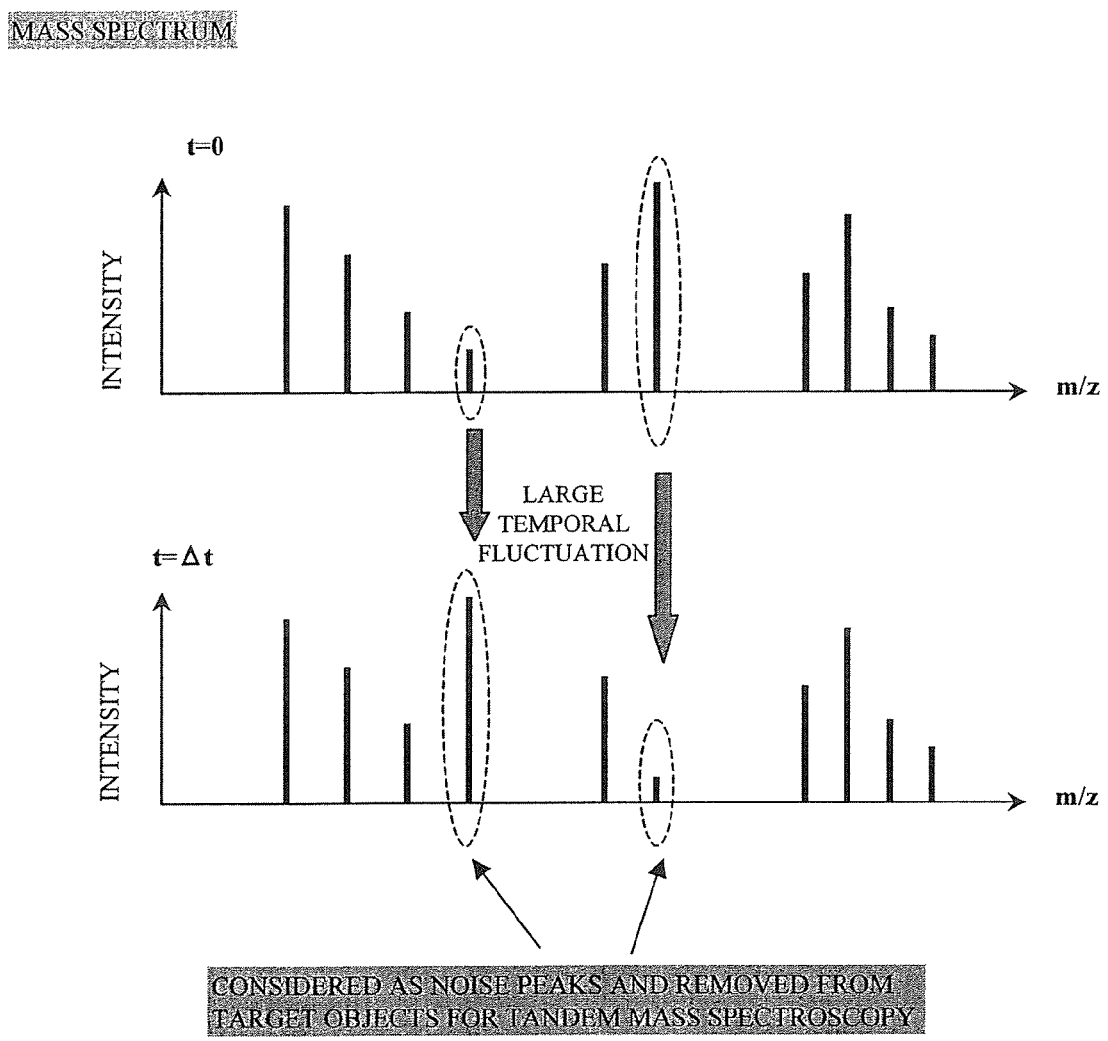
FIG. 21 shows the concept of the selection of the next tandem mass spectroscopy target in a $10^{th}$ embodiment of the invention.

With reference to FIG. 21, a tenth embodiment of the invention is described. In this embodiment, whether or not each peak in the $MS^1$ data measured within the real time of measurement is noise is automatically determined, and those peaks that are determined to be noise are removed from a list of valid peaks. For example, in the case where, when the same sample is subjected to mass spectroscopy a plurality of times at intervals, there is not much difference among most of the peaks in terms of intensity distribution tendencies in each measurement spectrum but there is a peak that is exhibiting more than 50% intensity fluctuations, as shown in FIG. 21, the greatly fluctuating peak is determined to be a noise peak and automatically removed from the targets for the next tandem mass spectroscopy. In accordance with the present embodiment, the possibility of subjecting a noise peak to tandem analysis in cases where, for example, the noise peak has accidentally become large can be avoided. Alternatively, in another method for noise determination, if an ion species with a certain m/z value is repeatedly detected with intensities exceeding a certain threshold $S_0$ for more than a certain period of time $T_0$ since the initial detection of the ion species, that ion species may be automatically determined to be noise or a peak deriving from impurities. In this case, the certain period $T_0$ or the certain threshold $S_0$ may be designated by the user. Further alternatively, a system may be adopted such that, if an ion species with a certain m/z value is repeatedly detected after more than a certain period $T_0$ since the initial detection of the ion species (t=0) (t>$T_0$), the ion species is removed from the target for tandem analysis ($MS^n(n \geq 2)$), and if an ion species is repeatedly detected within the certain period T0 (t≤$T_0$), even if that ion species has become a target for tandem mass spectroscopy ($MS^n(n \geq 2)$) once during this period (t≤$T_0$) and been stored in the internal database, the ion species can become a target for tandem mass spectroscopy ($MS_n(n \geq 2)$) any number of times as long as t≤$T_0$. In this case, the results of tandem mass spectroscopy (($MS_n(n \geq 2)$)) obtained from the same ion species are subjected to a merge process in a post-processing.

Figure 22:
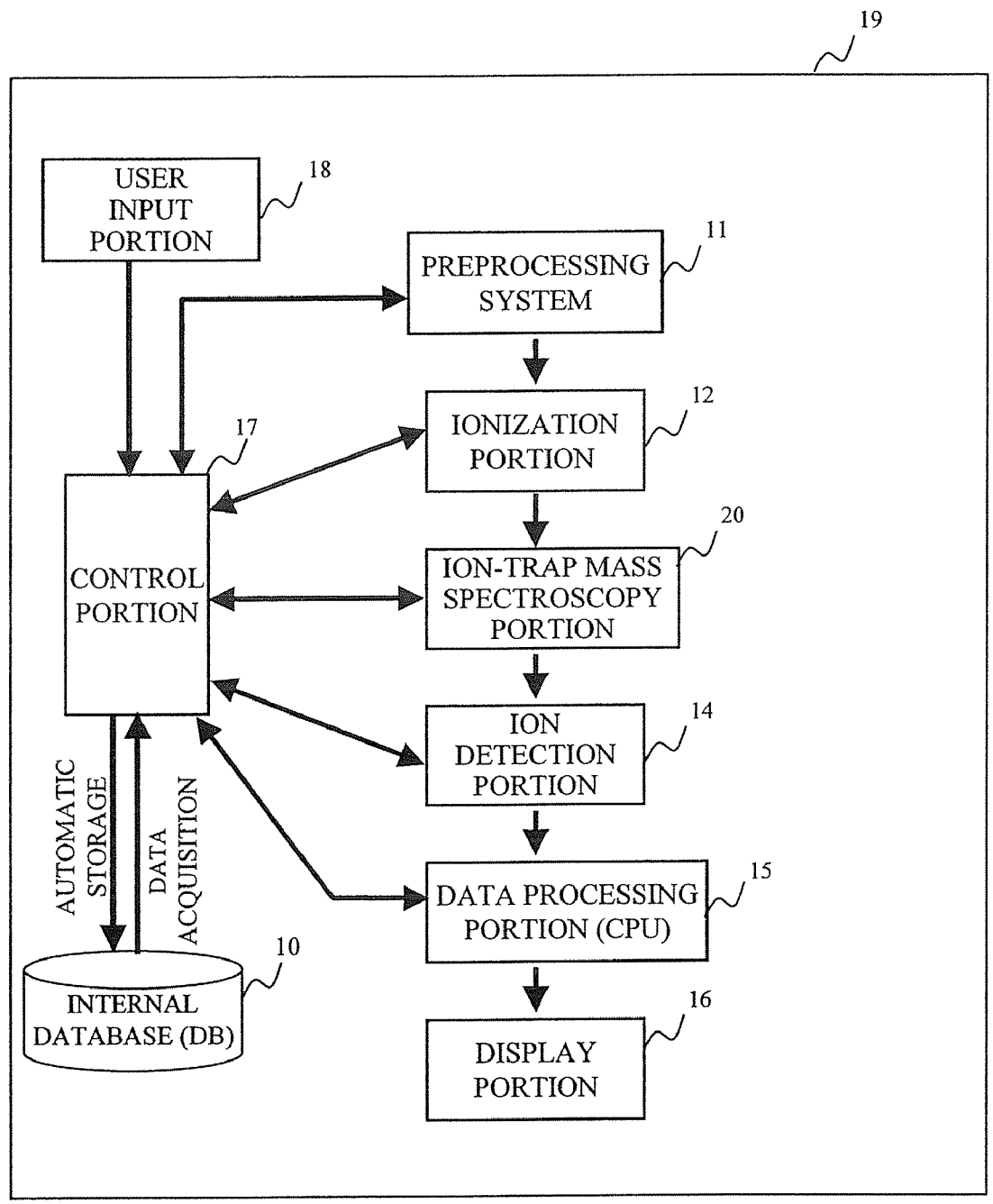
FIG. 22 schematically shows a mass spectroscopy system as a whole according to an $11^{th}$ embodiment of the invention.
Figure 22:
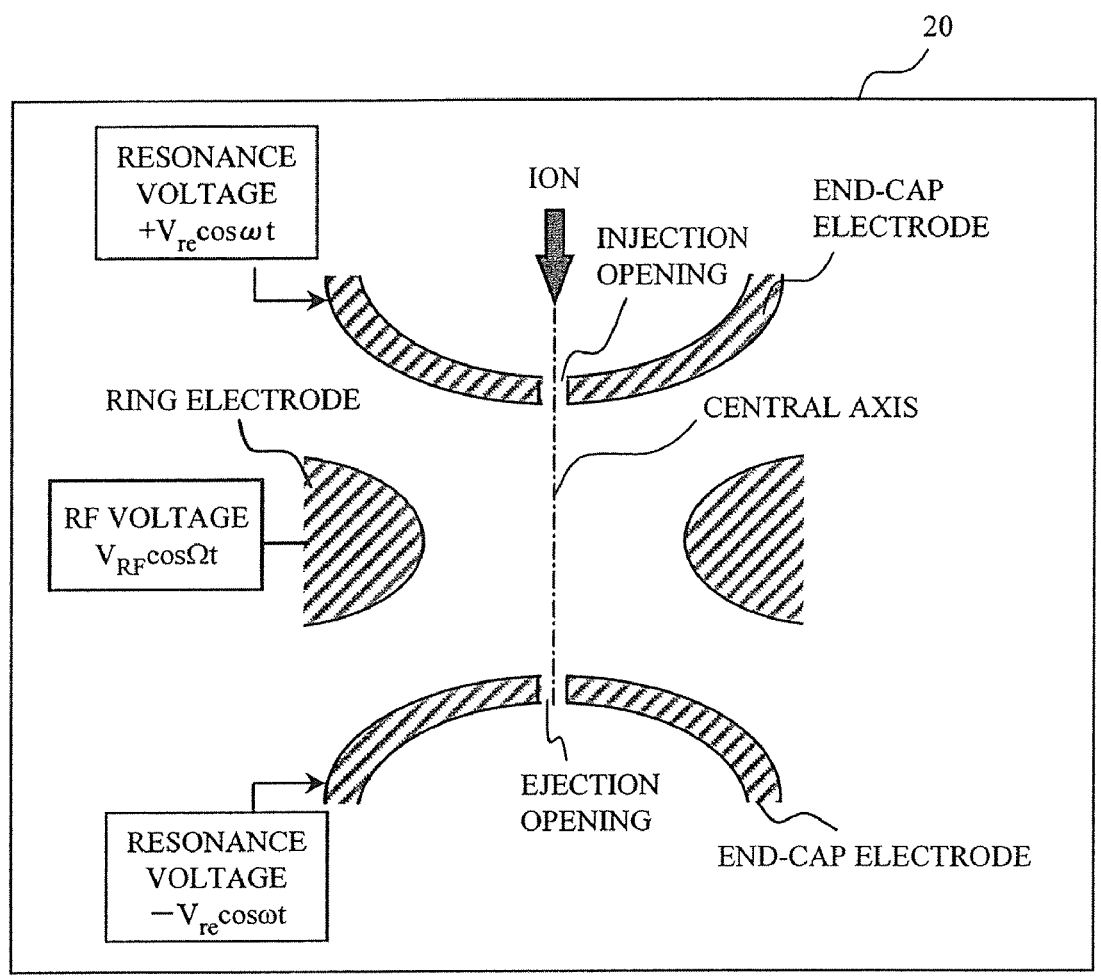

With reference to FIGS. 22a and 22b, an eleventh embodiment of the invention is described. As shown in FIG. 22a, in this embodiment, an ion trap mass spectroscopy unit is provided as the mass spectroscopy unit. The structure of the ion trap mass spectroscopy unit is shown in FIG. 22b. The ion trap is made up of a ring electrode and two end-cap electrodes disposed opposite each other with the ring electrode disposed therebetween. A radio-frequency (RF) voltage VRFcosΩt is applied across the ring electrode and the two end-cap electrodes. Thus, in the ion trap, there is mainly generated a high-frequency quadrupole electric field, and the ions vibrate at different frequencies depending on their m/z values and are trapped (accumulated). When collision induced dissociation (CID) is used as the dissociation method during tandem mass spectroscopy, the ion trap itself in which the neutral gas, such as He gas, is filled functions as a collision cell, there is no need to provide a separate collision cell. After the target for the tandem mass spectroscopy $MS''(n \geq 2)$ is automatically determined by the present invention, the ion species other than the specific ion species with the m/z value of the target are caused to be emitted by resonance. The specific ion species that are left in the ion trap are caused to vibrate by resonance to such an extent that they are not emitted from the ion trap, thereby causing the ion species to collide with the neutral gas and dissociating the target ion species for the tandem mass spectroscopy $MS''$ (n≥2). During this process, a resonance voltage is applied between the end-cap electrodes. The resonance voltage is a voltage $\pm V_{re}$ cos ωt with substantially the same frequency ω (≈$ω_0$) as the vibration frequency $ω_0$ of the vibration of the specific ion species in the ion trap and with an inversed phase. Voltages +$V_{re}$ cos ωt and −$V_{re}$ cos ωt are applied to the respective end-cap electrodes. Depending on the mass-to-charge ratio m/z value of the next target ion species that has been automatically determined by the system of the invention, the amplitude value of the high-frequency voltage, the frequency and amplitude of the resonance voltage, and so on, are automatically adjusted and optimized during the aforementioned tandem mass spectroscopy. Thus, since the ion trap is capable of carrying out the tandem mass spectroscopy $MS''$ (n≥2), it can very effectively applied to the system of the invention that automatically determines the next target.

Figure 23:
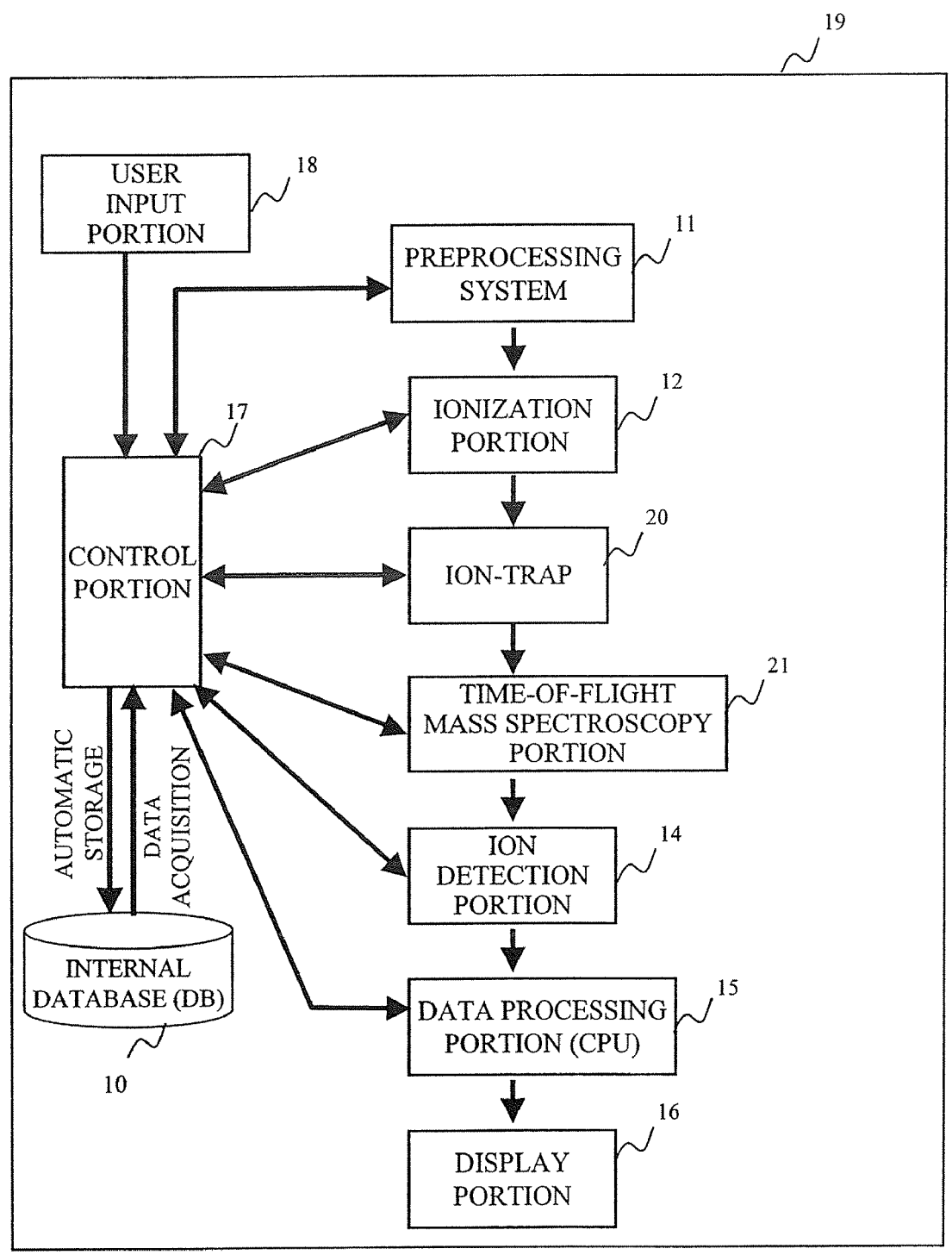
FIG. 23 schematically shows a mass spectroscopy system as a whole according to a $12^{th}$ embodiment of the invention.

With reference to FIG. 23, a twelfth embodiment of the invention is described. In this embodiment, an ion-trap, time-of-flight (TOF) mass spectroscopy unit is provided as the mass spectroscopy unit. In this case, the ion trap is used for the trapping of ions, selection of a parent ion, and as a collision cell, as in the eleventh embodiment. Depending on the mass-to-charge ratio m/z value of the next target ion species that has been automatically determined by the system of the invention, the amplitude value of the high-frequency voltage that is applied to the ion trap, the frequency and amplitude of the resonance voltage, and so on, are automatically adjusted and optimized during the above-described tandem mass spectroscopy, as in the eleventh embodiment. The actual mass spectroscopy is carried out in the TOF portion with high resolution. If it is determined that, based on a collation with the internal database of the invention, a tandem analysis is necessary, a parent ion is selected and dissociated by the ion trap and is then subjected to mass spectroscopy in the TOF. If it is determined that no tandem analysis is necessary, the parent ion is caused to pass through the ion trap and subjected to mass spectroscopy in the TOF. Thus, in accordance with the present embodiment, the need for tandem analysis can be automatically determined, so that analysis can be performed with a very high efficiency.

Figure 24:
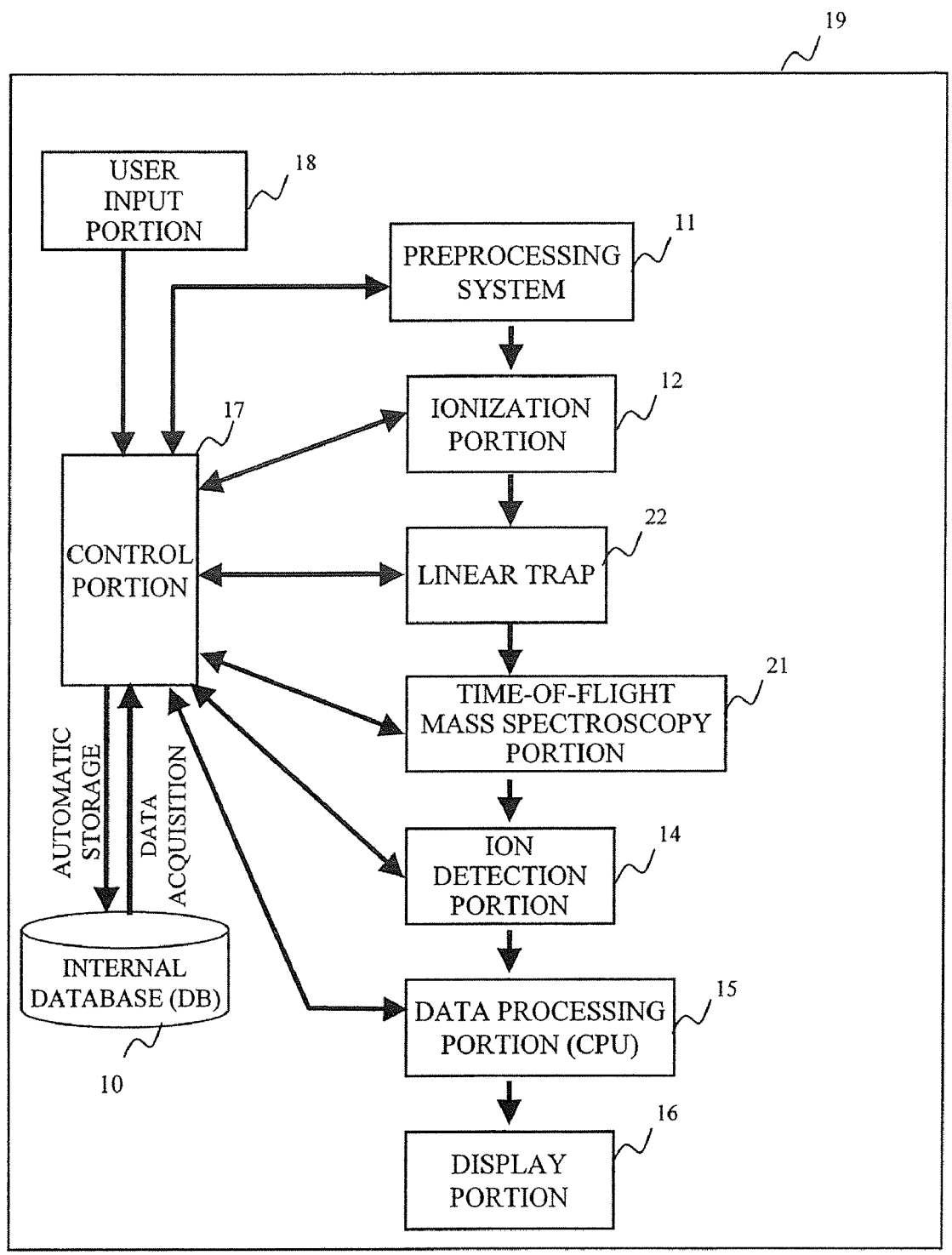
FIG. 24 schematically shows a mass spectroscopy system as a whole according to a $13^{th}$ embodiment of the invention.
Figure 24:
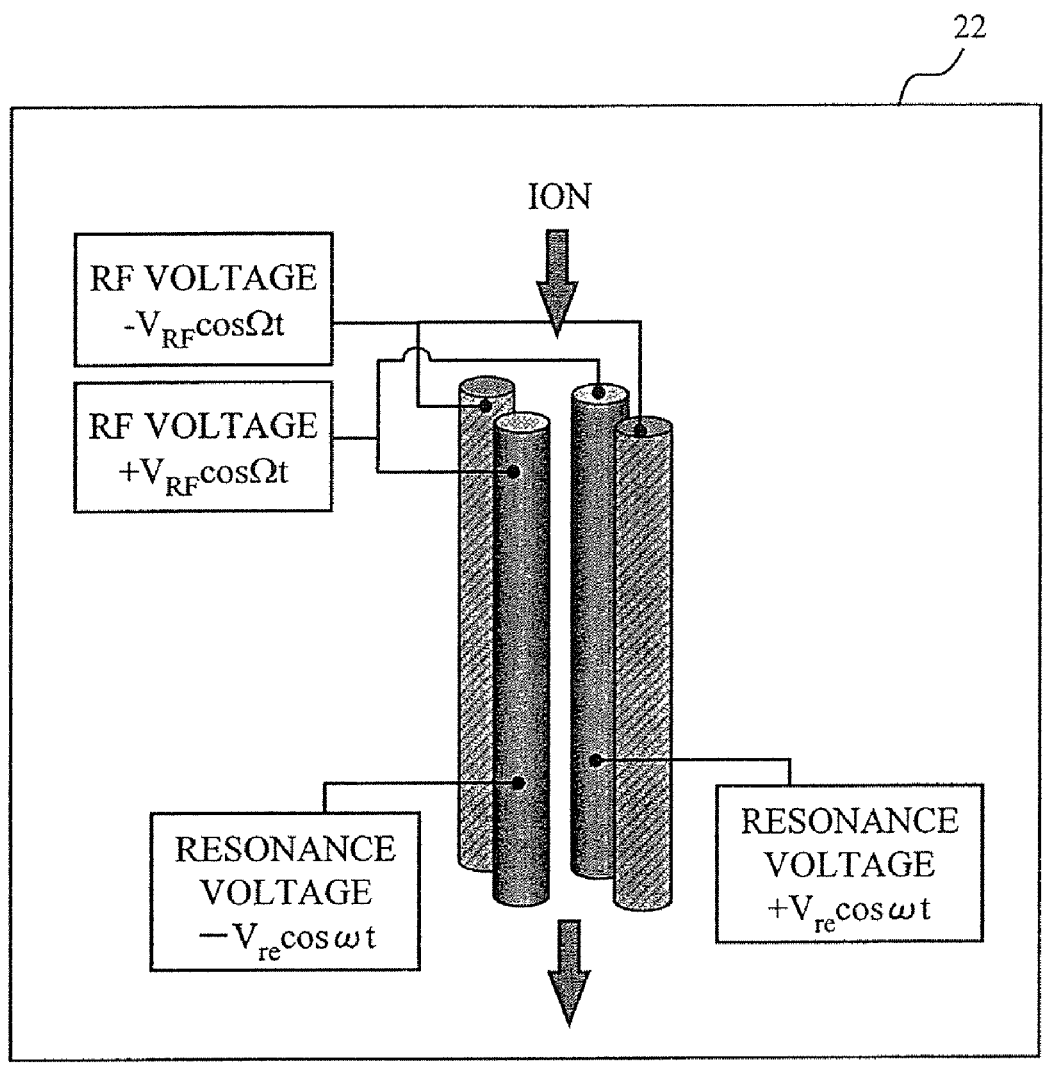

Now referring to FIGS. 24a and 24b, a thirteenth embodiment of the invention is described. As shown in FIG. 24a, this embodiment is characterized in that a linear trap time-of-flight (TOF) mass spectroscopy unit is provided as the mass spectroscopy unit. The structure of an ion trap mass spectroscopy unit is shown in FIG. 24b. The linear trap is made up of four pole-shaped electrodes (quadrupole electrode) between which a neutral gas is filled. The linear trap functions to store ions, select a parent ion, and as a collision cell. Opposed electrodes are considered as a pair of electrodes with the same potential, and a radio-frequency voltage ±$V_{RF}$ cos ωt of opposite phase is applied across each of the two pairs of electrodes. As a result, in the linear trap, there is generated mainly a radio-frequency quadrupole electric field, and the ions vibrate at different vibration frequencies depending on their m/z values and are trapped (accumulated). After the target for the tandem mass spectroscopy $MS''$ (n≥2) is automatically determined by the invention, all of the ion species other than the specific ion species with the m/z value of the target are resonance-ejected, and the specific ion species remaining in the linear trap are caused to resonate and vibrate to such an extent that they are not emitted from the linear trap, thereby causing the ion species to forcibly collide with the neutral gas and dissociating the target ion species for the tandem mass spectroscopy $MS''$ (n≥2). In this case, a resonance voltage is applied across a single opposed pair of electrodes. The resonance voltage is a voltage ±$V_{re}$ cos ωt with substantially the same frequency ω (≈ω₀) as the vibration frequency ω₀ of the vibration of the specific ion species in the ion trap and with an inversed phase. Voltages $+V_{re}\cos\omega t$ and $-V_{re}\cos\omega t$ are applied to the respective end-cap electrodes. Depending on the mass-to-charge ratio m/z value of the next target ion species that has been automatically determined by the system of the invention, the amplitude value of the high-frequency voltage, the frequency and amplitude of the resonance voltage, and so on, are automatically adjusted and optimized during the aforementioned tandem mass spectroscopy. As compared with the twelfth embodiment, the ion-trapping rate can be significantly improved (about 8 times). Thus, in accordance with the present embodiment, the content of the next analysis is determined based on high-sensitivity data, so that determination can be made with a very high accuracy.

Figure 25:
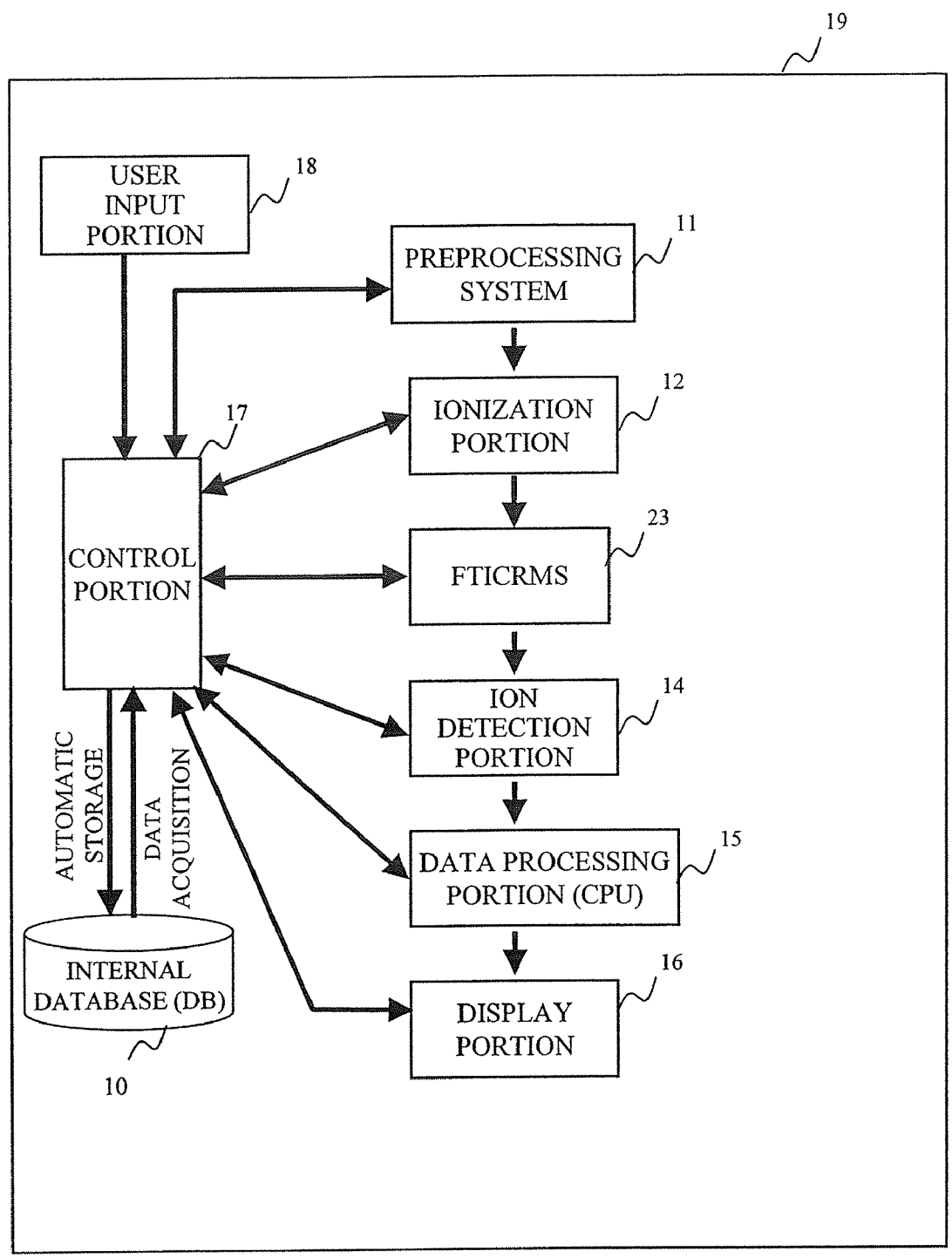
FIG. 25 schematically shows a mass spectroscopy system as a whole according to a $14^{th}$ embodiment of the invention.

With referent to FIG. 25, a fourteenth embodiment of the invention is described. In this embodiment, a Fourier-transform ion cyclotron resonance mass spectroscopy unit is provided as the mass spectroscopy unit. In the mass spectroscopy unit of the present embodiment, a top-down analysis of proteins can be performed, namely proteins that has not yet been subjected to a preprocessing such as enzymatic digestion can be directly subjected to tandem mass spectroscopy. Thus, the present embodiment is suitable for the analysis of minute amounts of proteins, for example.

Figure 26:
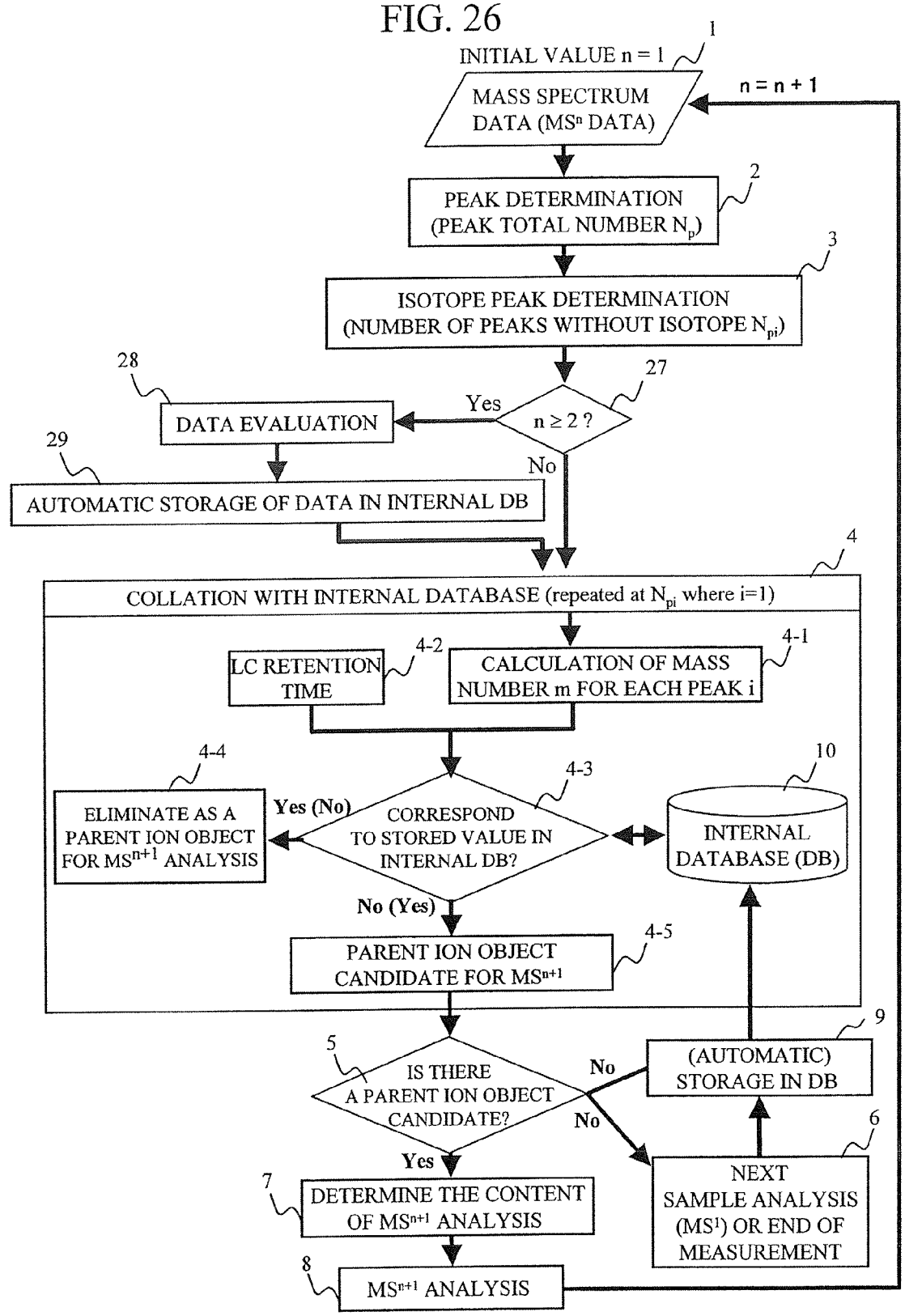
FIG. 26 schematically shows an automatic determination process in the mass spectroscopy flow according to a $15^{th}$ embodiment of the invention.
Figure 27:
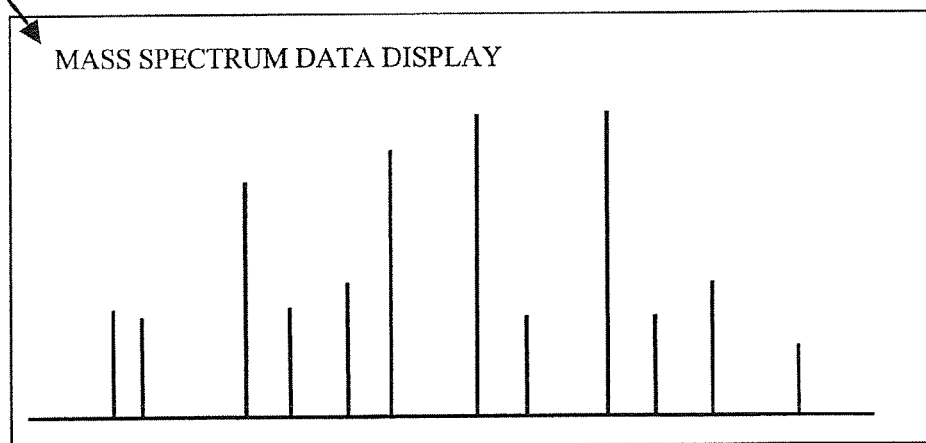
FIG. 27 schematically shows an internal database in the $15^{th}$ embodiment of the invention.
Figure 28:
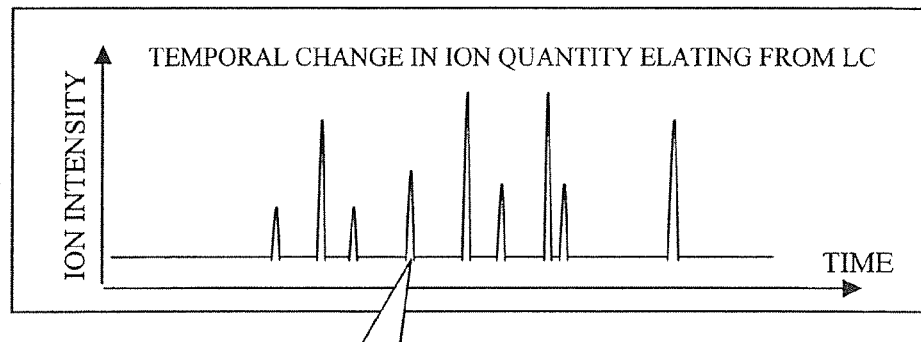
FIG. 28 shows the concept of a quality evaluation of mass spectroscopy data in the $15^{th}$ embodiment of the invention.
Figure 28:
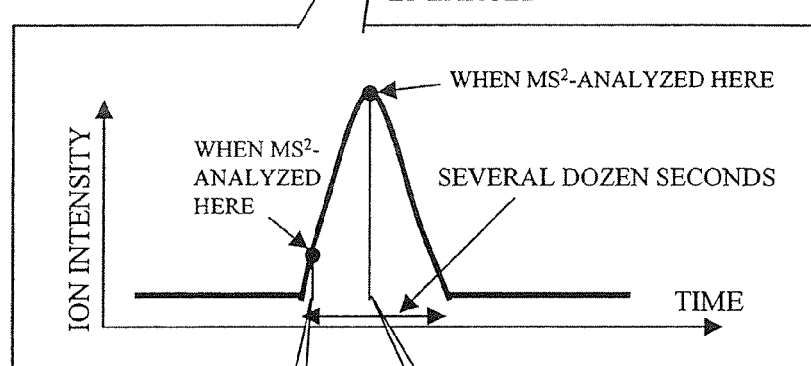
Figure 28:
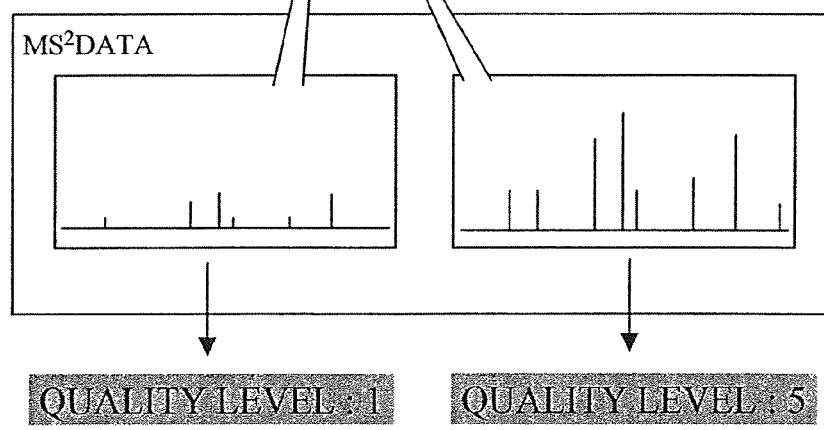

With reference now to FIGS. 26, 27, and 28, a fifteenth embodiment of the invention is described. In this embodiment, when the $MS^n$ analysis ($n \geq 2$) is performed, the information about the ions that have been analyzed and the measurement conditions are automatically stored in the internal database provided inside the mass spectroscopy system, with each item of data allocated a unique registration number. As shown in FIG. 26, when an n-stage determination 27 is performed where n is 2 or more, the evaluation 28 of the obtained mass spectrum data is performed and then the information about the ions and the measurement conditions are automatically stored 29 in the internal database provided inside the mass spectroscopy system, with each item of data allocated a unique registration number. As shown in FIG. 27, the registration number allocated upon storage in the internal database is linked with the mass spectrum data that has actually been measured. Thus, at the end of measurement, the user can call the mass spectrum data by clicking the registration number. In accordance with the present embodiment, the mass spectrum data of the ion species of interest can be efficiently referred to by the user, displayed, or outputted in the form of a file. The information about the ion species that is automatically stored include the registration number, the mass number m of ion, the valence z of ion, and the retention time τ in LC. The measurement conditions include the accumulation time of the ion species in cases where there is an ion accumulating portion, such as an ion trap (FIG. 27). As an index for the evaluation of the quality of the mass spectrum data that has been measured, the quality is evaluated in 5 steps in the present embodiment, with the higher quality mass spectrum data being allocated higher index values. Now referring to FIG. 28, an example of the evaluation of mass spectrum data is described. Ions that have been temporally separated by LC are detected at the retention times adapted for the individual ions, as shown in FIG. 28A. Although the ions are detected at each corresponding time, each ion peak at the detection time has a width of dozens to hundreds of seconds (FIG. 28B), the mass spectrum data that is obtained differs depending on time even if the ion as the measurement object has been detected. In the event the $MS^n$ analysis is conducted at the initial phase of detection of the ions, or after the ions have all been detected (i.e., near the foot of the peak in FIG. 28B), the absolute amount of ions is small, so that it is more likely that the mass spectrum data that is obtained is of lower quality with a low S/N ratio (FIG. 28C). On the other hand, if the $MS^n$ analysis is conducted at the peak where the amount of ions detected is maximum, it is more likely that the mass spectrum data that is obtained is of higher quality with a high S/N ratio (FIG. 28C). Thus, the quality of the mass spectrum data of even the same substance differs depending on the time of measurement. In accordance with the present embodiment, therefore, the quality of each mass spectrum data is evaluated and the result is displayed, whereby the user can easily determined the quality of each measurement data and perform a highly accurate analysis. In cases where the measured object is peptides, the object of evaluation may be the information about the amino acids that can be read from the mass spectrum data of $MS^n$ ($n \geq 2$), such as the amino acid sequence or a modified portion. When the information about amino acids is used as the object of evaluation, the grounds for determination or the data that has been used in determination should preferably be simultaneously outputted. The evaluation of data and the storage of the quality information may be performed after all the measurements have been made.

Figure 20:
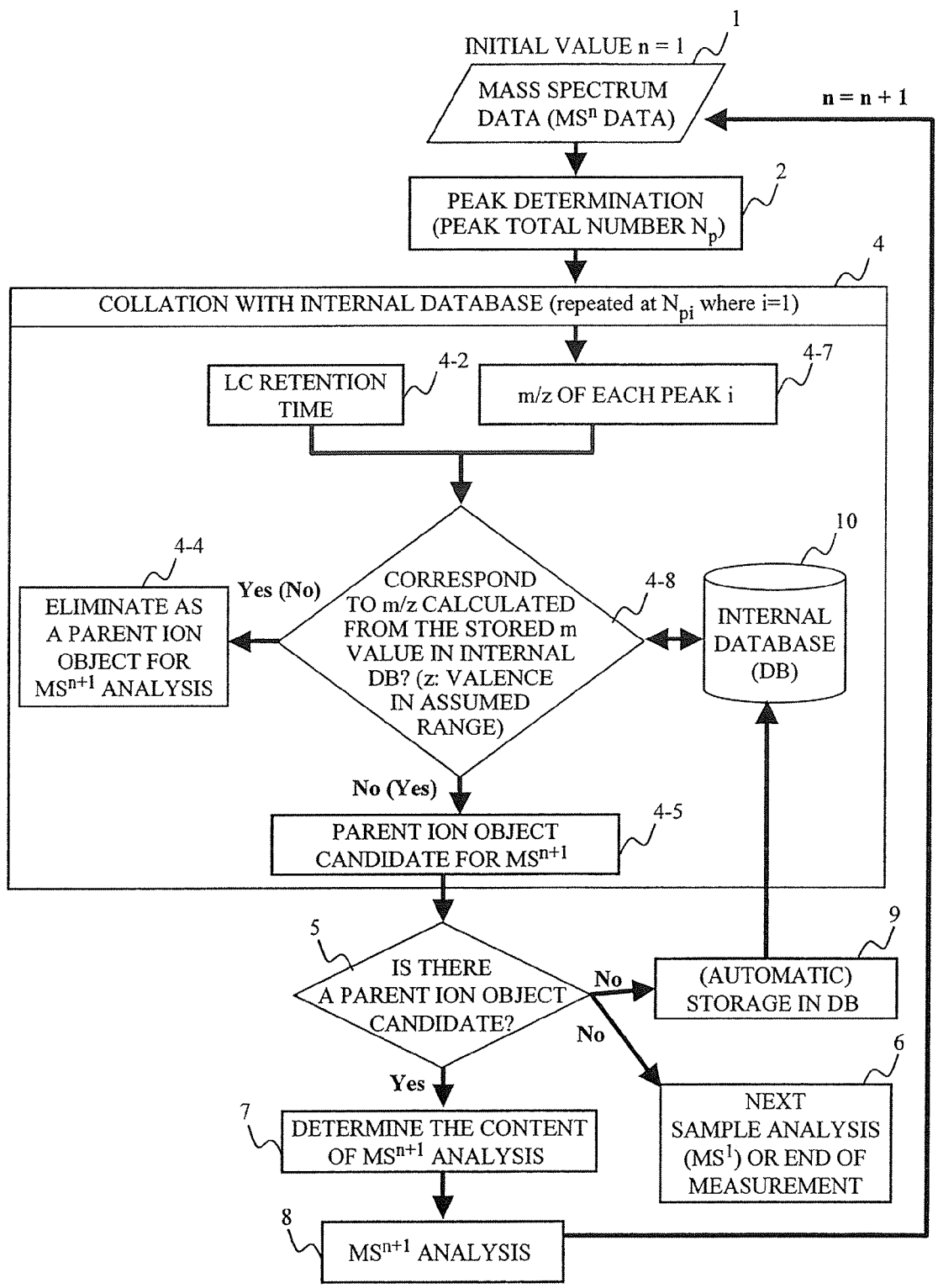
FIG. 20 schematically shows an automatic determination process in the mass spectroscopy flow according to a ninth embodiment of the invention.
Figure 29:
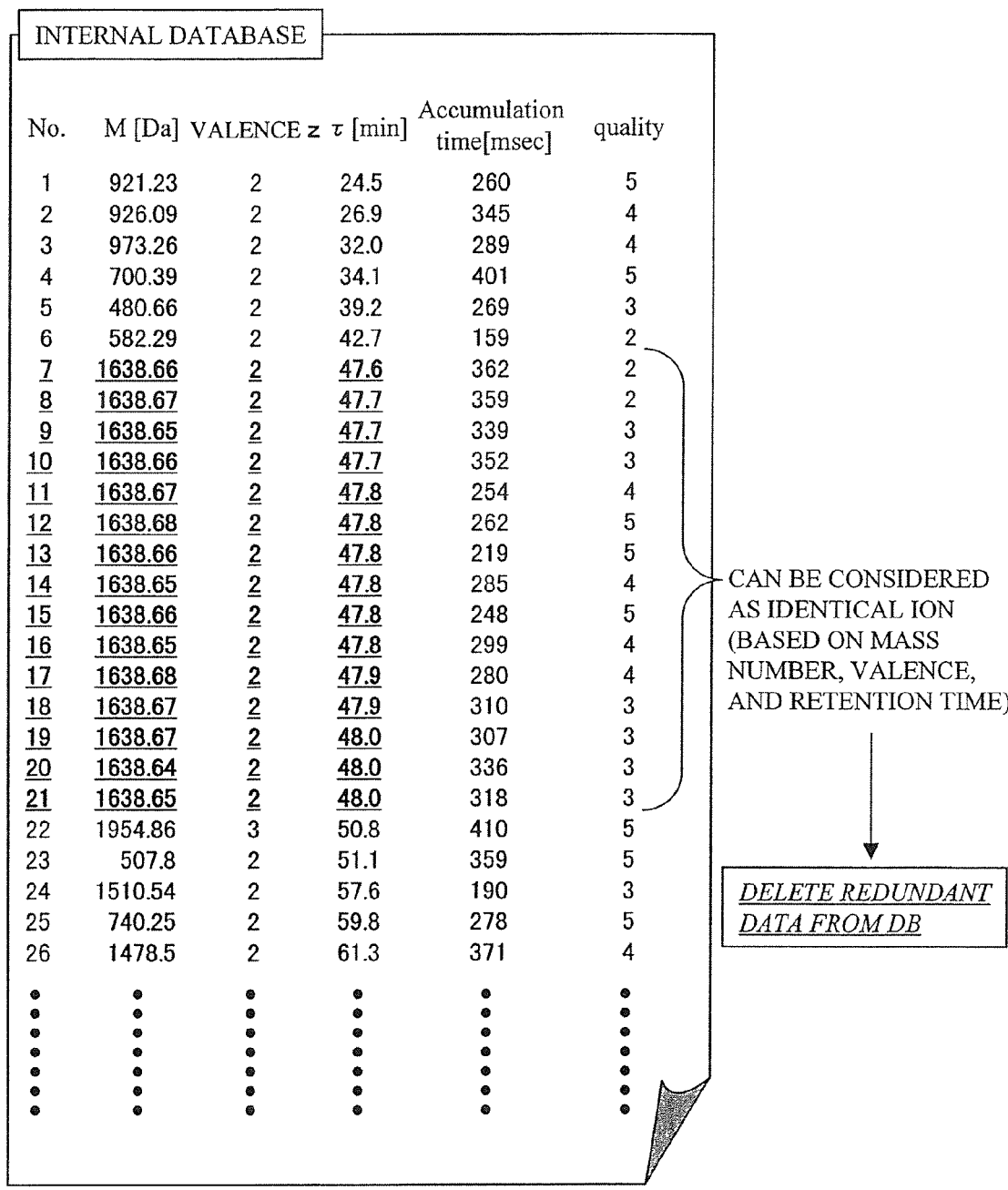
FIG. 29 shows the concept of data processing in the internal database in a $16^{th}$ embodiment of the invention.

With reference to FIGS. 29 and 20, a sixteenth embodiment of the invention is described. In this embodiment, with regard to the information about the ion species that has been stored in the internal database, the information about the ion species that can be considered to be identical is put in order. The ion species with registration numbers Nos. 7 to 21 in FIG. 29 can be considered to be the same ion species based on the mass number, valence, and the value of the retention time, on the assumption that the tolerance of mass number is ±0.05 Da, and the tolerance of retention time is ±1.0 min. In this case, the tolerances may be set by the user. This determination is performed in a internal database storage data processing 30 shown in FIG. 30, whereby redundant data other than specific data is automatically eliminated from the database. The specific data includes data with highest quality, data with higher intensities, or data obtained by adding up a plurality of redundant items of data, for example. In accordance with the present embodiment, such redundant data are automatically eliminated from the database, thereby reducing the redundancy level of the database. With regard to the actually measured mass spectrum data, too, the data about the ion species that can be considered to be identical is eliminated, or a plurality of items of the mass spectrum data about the ion species that can be considered identical are added into a single item of data in the internal DB stored data processing 30. With regard to the data processing in the present invention, it is also possible to perform the processing after all of the measurements have been made. The consolidation of the redundant data in the database may be performed across a plurality of databases by comparing the stored data in the individual databases.

Figure 30:
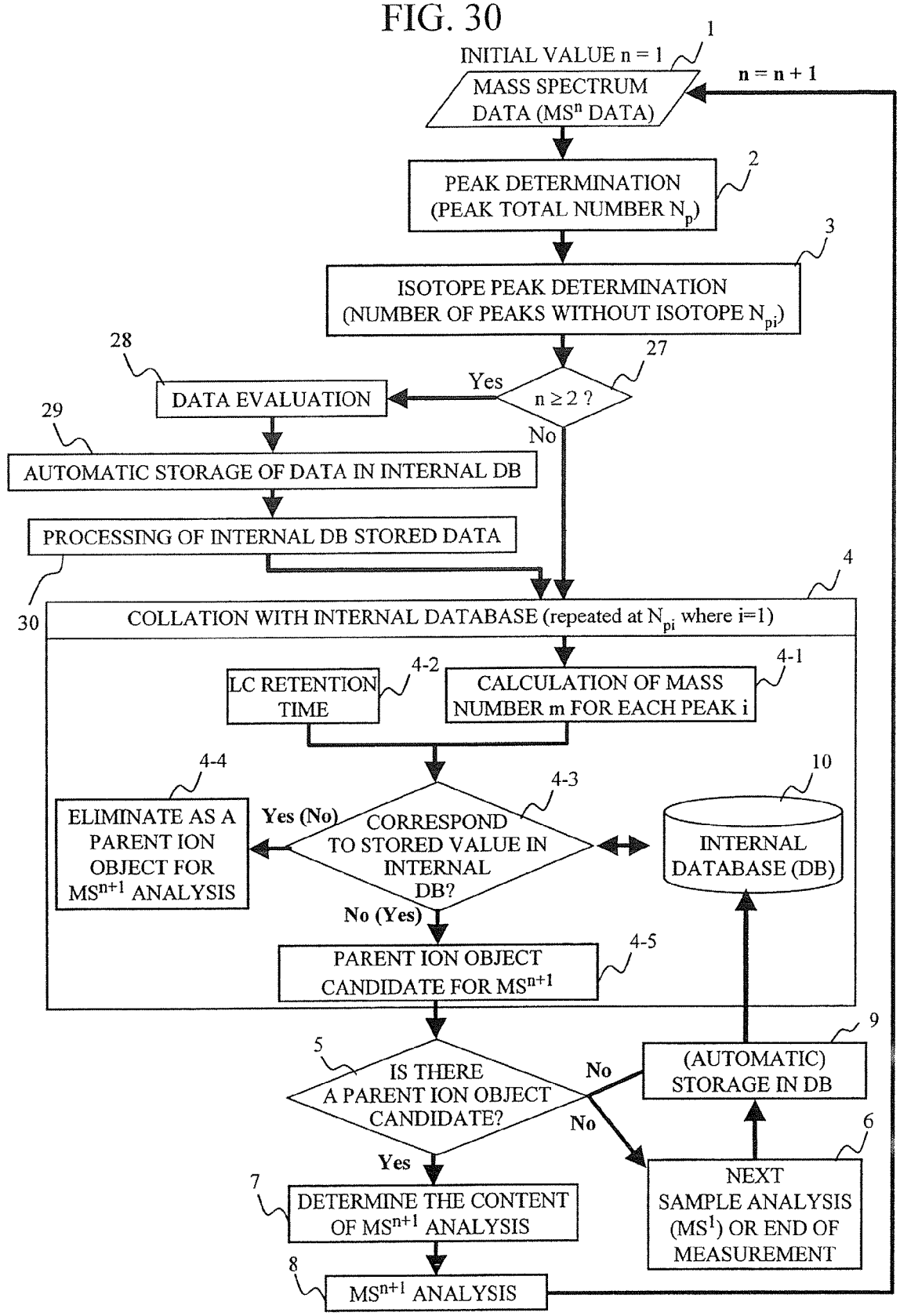
FIG. 30 shows the concept of an automatic determination process in a mass spectroscopy flow in the $16^{th}$ embodiment of the invention.
Figure 31:
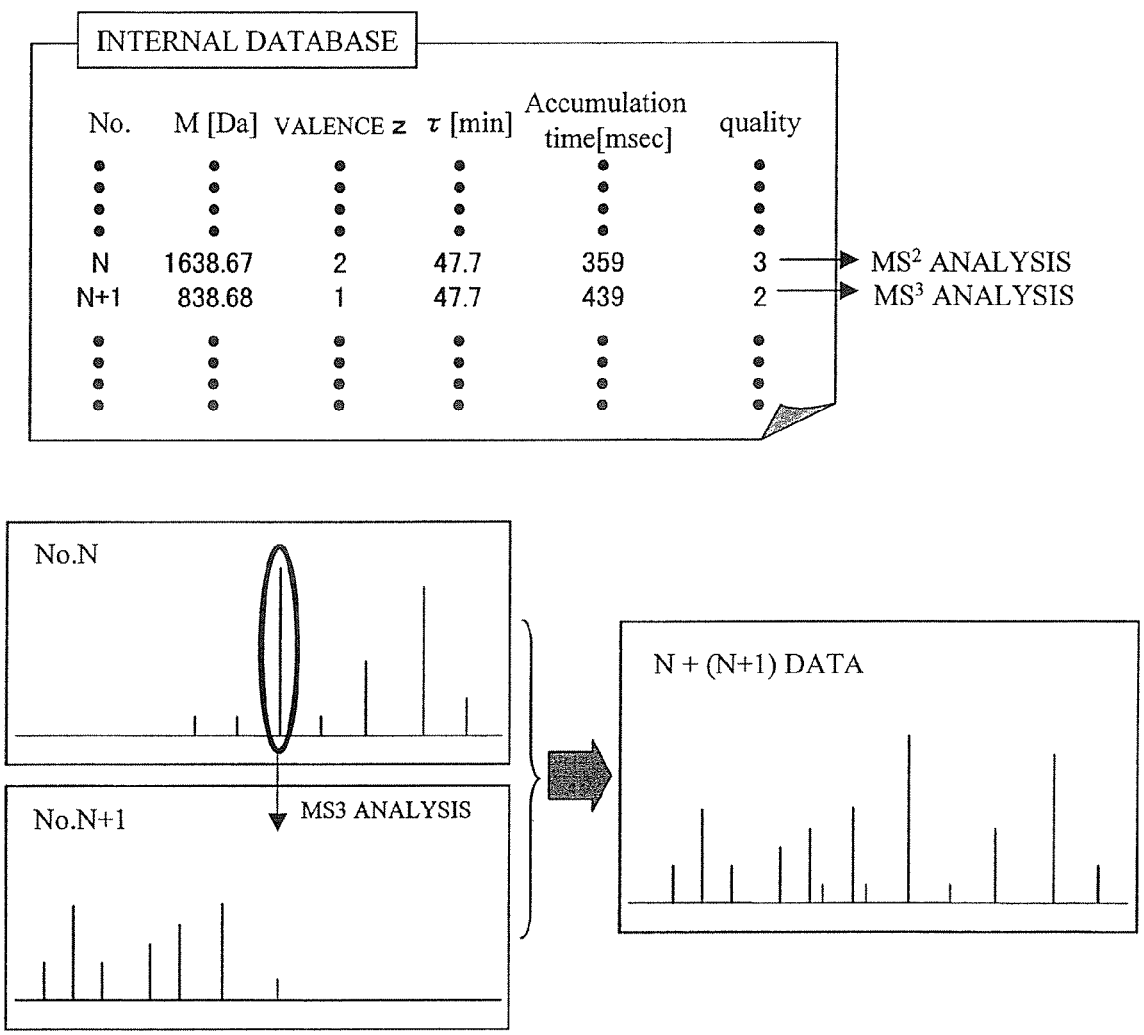
FIG. 31 shows the concept of addition of $MS^2$ data and $MS^n$ ($n \geq 3$) in a $17^{th}$ embodiment of the invention.

With reference to FIG. 31, a seventeenth embodiment of the invention is described. In this embodiment, when the $MS^n$ ($n \geq 3$) is performed, the mass spectrum data of $MS^2$ and the mass spectrum data of $MS^n$ ($n \geq 3$) are added. Alternatively, when, in the case where there was a peak with the same mass number m as the target ion species during the $MS^2$ but with a different valence (namely, a different m/z value), the $MS^2$ has been repeated by using that peak as the target (parent ion) instead of the $MS^2$ ($n \geq 3$) analysis, the mass spectrum data of the first $MS^2$ and the mass spectrum data of the second $MS^2$, which have been obtained by using as the targets the peaks with the same mass number and different valences, are added. When the object of measurement is a peptide, a database search is generally used for the analysis of the resultant mass spectrum data. However, the database used for the database search is constructed on the basis of the $MS^2$ analysis data, and it is difficult to use the $MS^n$ ($n \geq 3$) analysis data as is. Accordingly, in accordance with the invention, when the $MS^n$ analysis is performed, it is possible to combine the mass spectrum data of the $MS^2$ and the mass spectrum data of the $MS^n$ ($n \geq 3$) in the internal DB stored data processing 30 as shown in FIG. 30. In this case, a certain weight may be added to the $MS^n$ data that is combined. In accordance with the present embodiment, the user can analyze the $MS^n$ measured mass spectrum data easily using the database search. The data processing in accordance with the present invention may be performed after all the measurements have been made.

Figure 32:
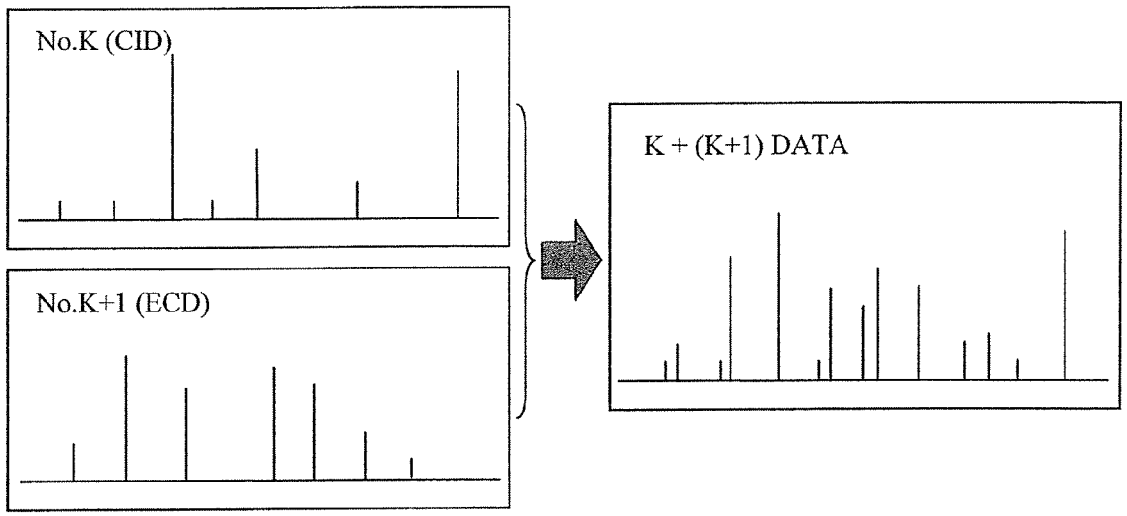
FIG. 32 shows the concept of addition of data using a different dissociation method in an $18^{th}$ embodiment of the invention.

With reference now to FIG. 32, an eighteenth embodiment of the invention is described. In this embodiment, the mass spectrum data obtained by using different dissociation methods are added. When the mass spectrum data is measured from the same ion using different dissociation methods, the dissociation efficiency or the obtained tendency of the ion differ depending on the dissociation methods. Thus, by combining data obtained by different dissociation methods and then analyzing the combined data, it can be expected that the measurement object can be identified with higher accuracy. A case will be described in the following where mass spectrum data is obtained using collision induced dissociation (CID) and electron capture dissociation (ECD). When the object of measurement is a peptide, use of CID as the dissociation method result in the detection of mainly b and y ions. On the other hand, it has been reported that use of ECD resulted in the detection of mainly c and z ions. Thus, in accordance with the invention, a plurality of data obtained by using different dissociation methods are added in the internal DB stored data processing 30 shown in FIG. 30. In accordance with the embodiment, the identification accuracy can be expected to improve, and it can also be expected that the probability of identification of ions, which has been difficult by the aforementioned methods individually, is improved. The data processing in the present embodiment may be performed after all of the measurements have been made.

Figure 33:
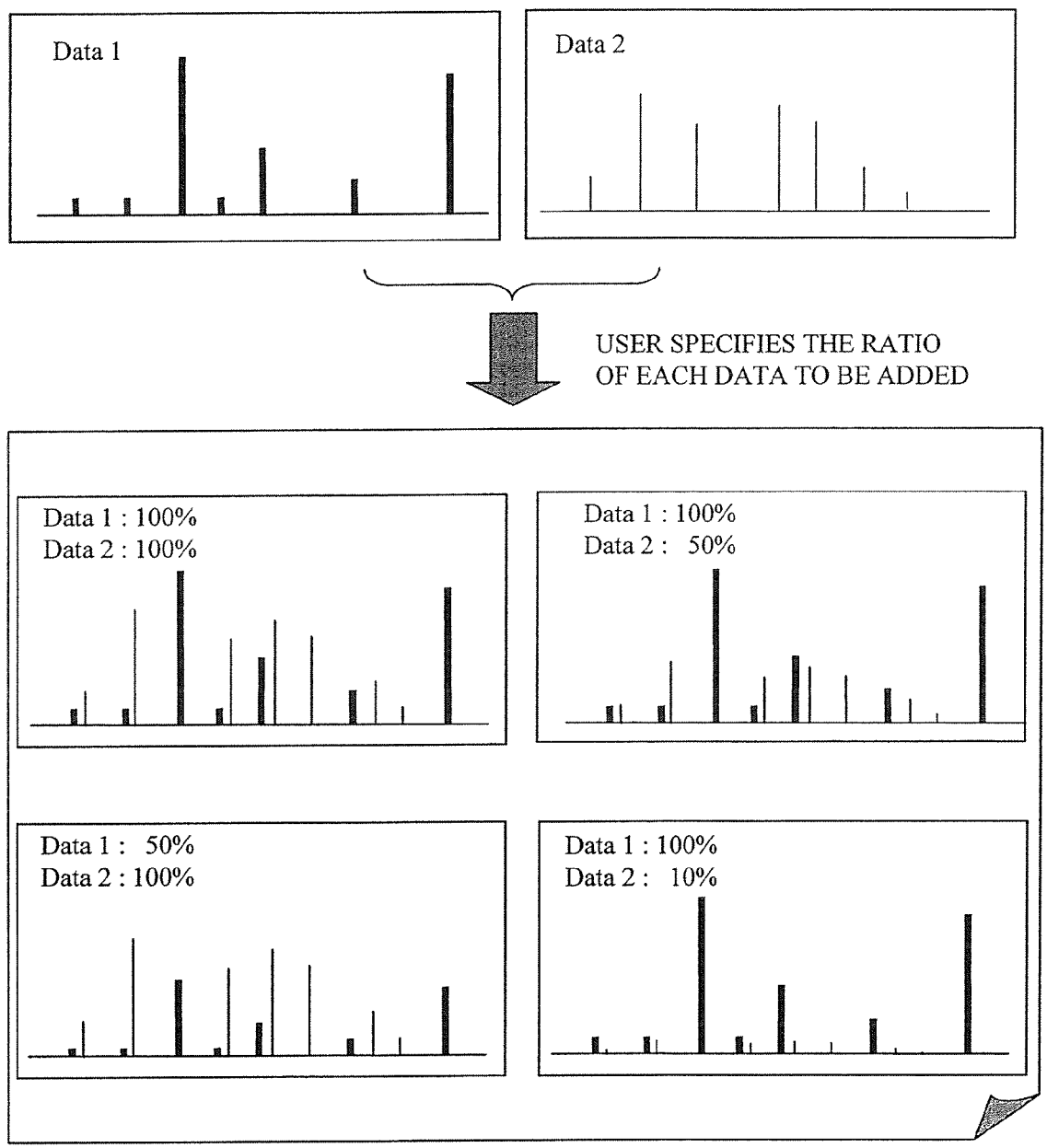
FIG. 33 shows the concept of changing addition process conditions for a plurality of items of mass spectrum data in a $19^{th}$ embodiment of the invention.

With reference to FIG. 33, a nineteenth embodiment of the invention is described. In this embodiment, when performing the addition of a plurality of mass spectrum data in the internal DB stored data processing 30 shown in FIG. 30 (such as that in embodiments 17 and 18), the user is allowed to designate the ratio of addition. For example, when there is only a minute amount of ions that are to be analyzed, by varying the ratio of addition, the analysis of mass spectrum data can be performed by taking into consideration the amount of the parent ion to be dissociated. Although in the present embodiment the processing involves two pieces of data, more than two pieces of data may be similarly designated. In accordance with the embodiment, more accurate analysis can be performed in which the fragment intensity is taken into consideration. The data processing in the present embodiment may be performed after all the measurements have been made. The present embodiment may be adapted such that the entire MS measurement data is converted into monovalent ion data.

Figure 34:
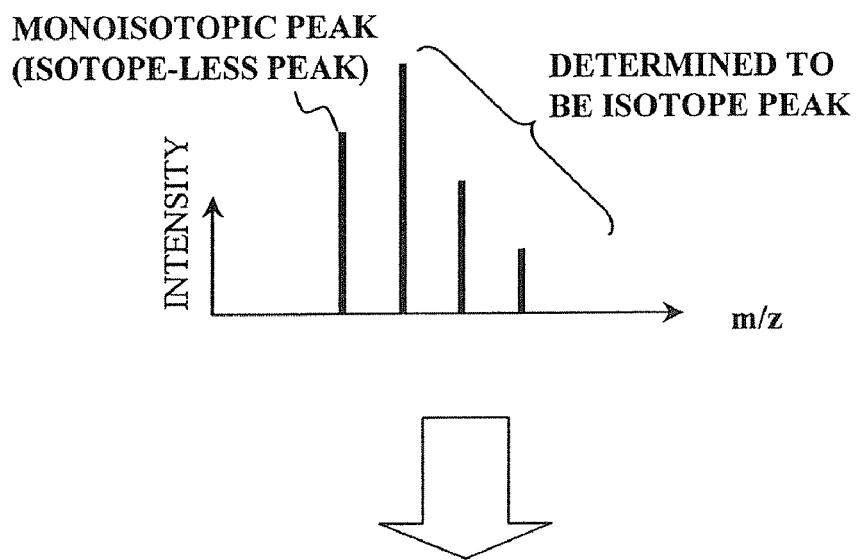
FIG. 34 shows the concept of addition of an isotope peak intensity and a monoisotopic peak intensity in a $20^{th}$ embodiment of the invention.
Figure 34:
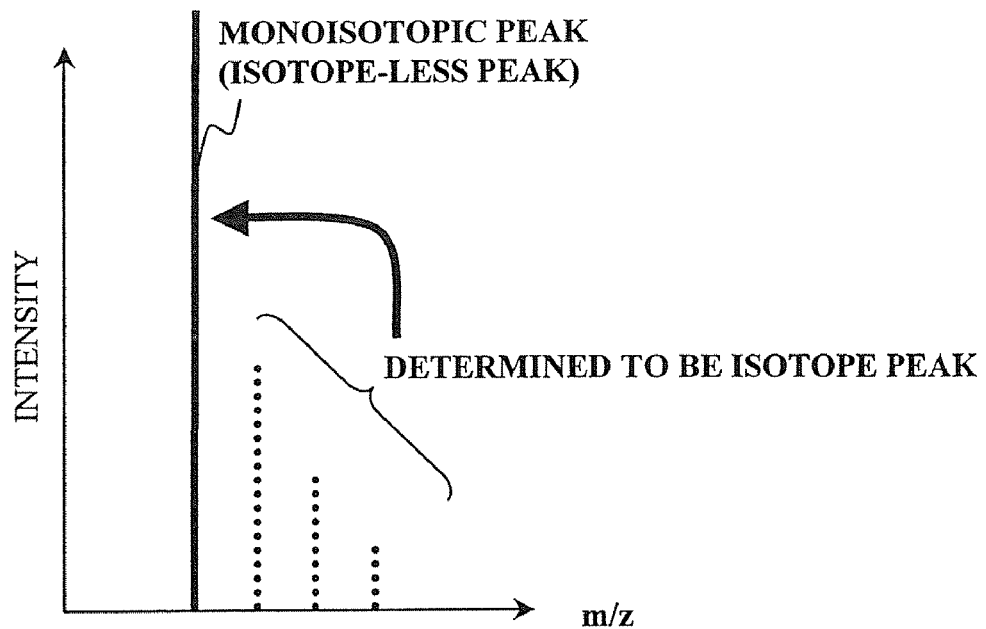

With reference now to FIG. 34, a twentieth embodiment of the invention is described. In this embodiment, the intensity of the ions that have been determined to be isotope peaks can be added to a monoisotopic peak. As described with reference to the first embodiment of the invention, the intensity of the isotope peaks determined from the ion intensity and peak interval is added to the intensity of the monoisotopic peak in the internal DB stored data processing 30 shown in FIG. 30. In accordance with the present embodiment, more accurate analysis can be performed in which the entire intensity of the ions as the object of measurement is taken into consideration. The data processing in the embodiment may be performed after all the measurements have been made.

In the following, a method of correcting the mass in analysis data is described as a $21^{st}$ embodiment of the invention. In the shotgun analysis of proteins, for example, external databases of genes or proteins are searched based on the result of mass spectroscopy in order to finally identify the chemical structure, for example, of biopolymers. In this case, the higher the accuracy of the mass of the ion that has been analyzed, the more accurately and efficiently the identification of biopolymers can be made. Thus, for such analysis, it is important to use a time-of-flight (TOF) mass spectrometer or Fourier transform ion cyclotron resonance (FTICR) mass spectrometer, which have a relatively high mass accuracy. However, the mass accuracy of the time-of-flight (TOF) mass spectrometer can be affected by the room temperature of the location where the equipment is installed. Should the mass accuracy fluctuate more than expected for one reason or another, the biopolymer might not be accurately identified even if the external-database search is conducted. For this reason, an internal reference substance of which the m/z of a detected ion is known is often analyzed in advance immediately prior to analysis, and the m/z of the mass spectrometer is calibrated based on the result of the prior analysis. However, there is the possibility that, in LC/MS where analysis is conducted continuously for hours on end, the mass accuracy might fluctuate more than expected. Thus, if a known ion of which the mass-to-charge ratio m/z is known in advance is detected in the ions detected by mass spectroscopy, the m/z of the other detected ions can be corrected based on the information about the known ion. By detecting a plurality of known ions, the accuracy of the m/z after correction can be improved greatly. One problem of this method is that it is bothersome, as the analysis data must be corrected by a kind of manual operation. If, however, there is information available in the internal database 10 concerning the m or m/z of the ions that could be detected or the retention time $\tau$ of LC, the known ions detected by $MS^1$ could be identified using that information. By identifying a plurality of known ions, the temporal fluctuation of m/z could also be predicted by information processing techniques, so that the m/z of the analyzed ions could be automatically corrected. This means that data of high mass accuracy can be easily acquired even if the mass accuracy of the mass spectrometer fluctuates more than expected. Moreover, when a mass spectrometer equipped with this type of information processing function is employed, the need for analyzing known substances prior to analysis can be eliminated, so that the burden on the user can be reduced. Thus, the information stored in the internal database 10 can be substantially and effectively utilized for the calibration or correction of the m/z of analysis data, as well as for the control of the real-time mass spectrometer.

(Real-Time Fast De Novo)

Figure 35:
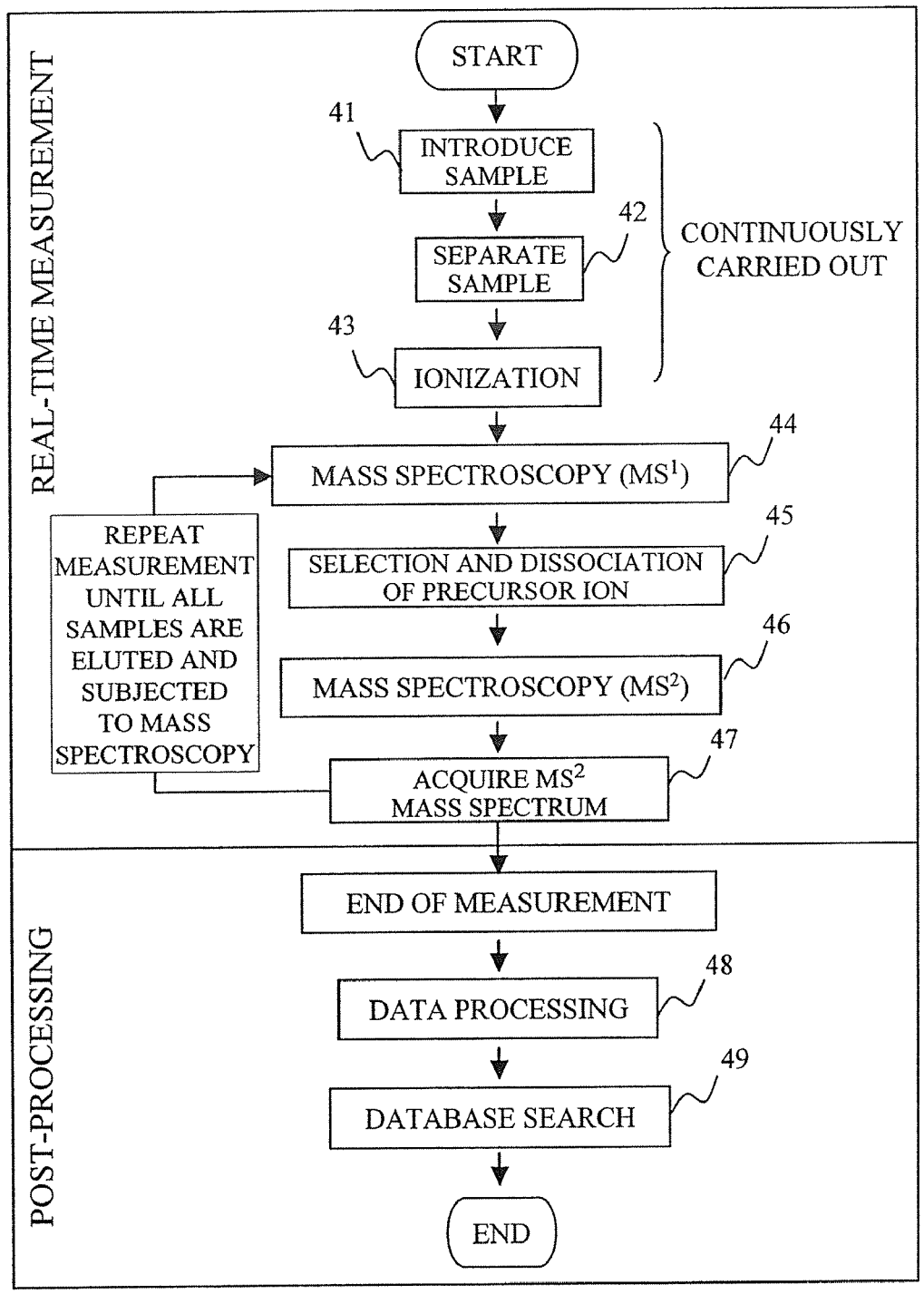
FIG. 35A schematically shows a typical flow of protein analysis and protein identification in the prior art.
FIG. 35B shows the concept of a flow of protein analysis and protein identification in a $22^{nd}$ embodiment of the invention.
Figure 35:
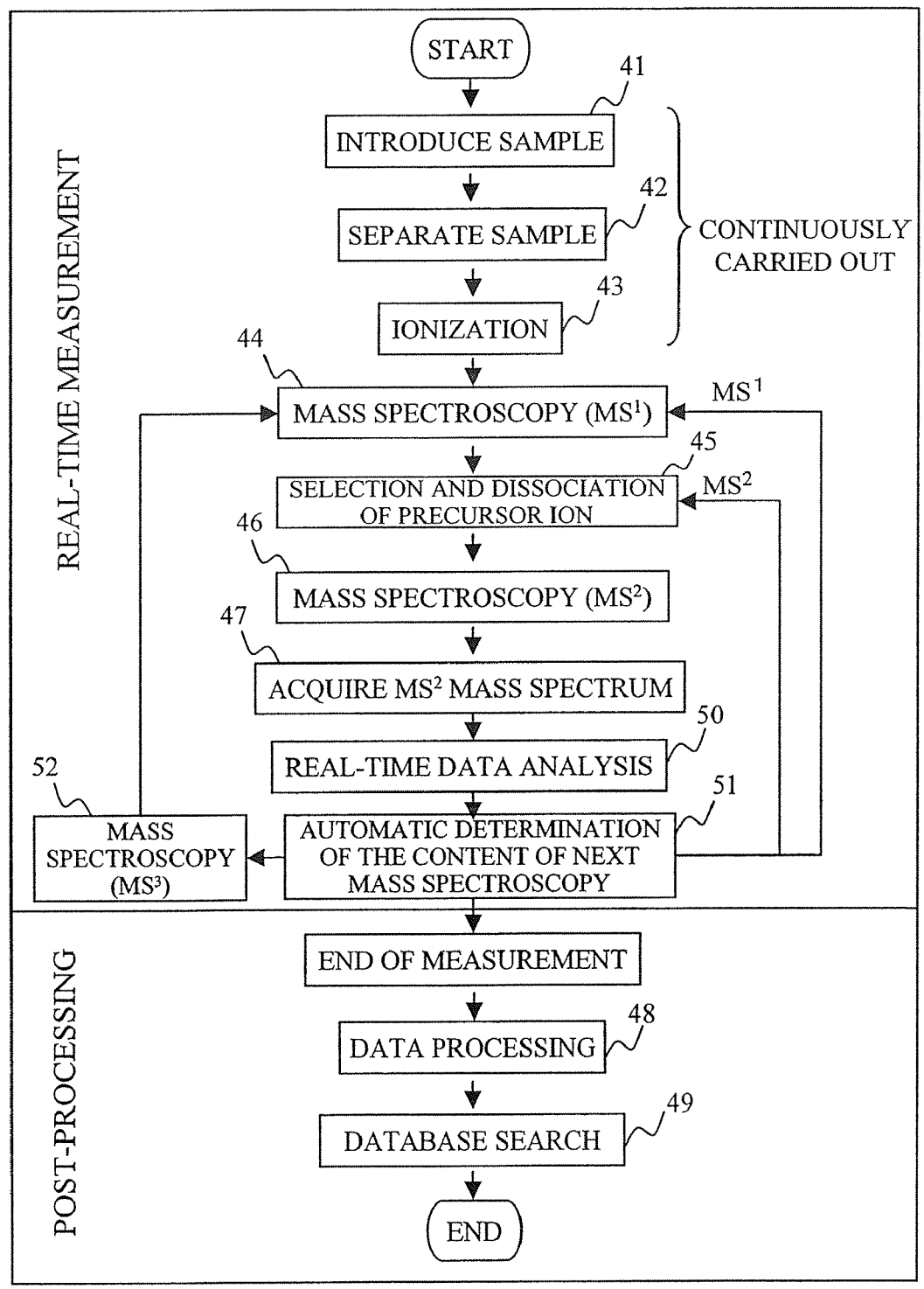

Hereafter, a $22^{nd}$ embodiment of the invention is described. FIG. 35*a* shows a flow chart of a comparative example involving the use of tandem mass spectrometer, starting with the analysis of a protein and ending with the identification of the protein. A protein sample is rendered into a peptide sample fragmented by enzyme digestion, for example. The peptide sample is then separated LC or GC and then ionized. Thereafter, a mass spectroscopy ($MS^1$) is carried out, and a precursor ion (parent ion) to be subjected to a $MS^2$ analysis is selected from the detected ions. After the selected precursor ion is dissociated, a mass spectroscopy ($MS^2$) is carried out, thereby obtaining mass spectrum data. The resultant mass spectrum data is subjected to a data processing (48) in a post-processing after the end of measurement, where noise peaks and isotope peaks are removed and the valence of ions is determined, for example. Then, a database search (49) is conducted using a protein database consisting of known proteins. In this identification flow, since the analysis of the obtained $MS^2$ mass spectrum data is performed in a post-processing after the end of measurement, the validity of the $MS^2$ mass spectrum data cannot be determined on a real-time basis during measurement. Meanwhile, it is important to obtain as much information as possible in a single measurement in cases where there is only an extremely minute amount of sample available, such as a diseased protein, for in such cases it is difficult to repeat mass spectroscopy.

Figure 36:
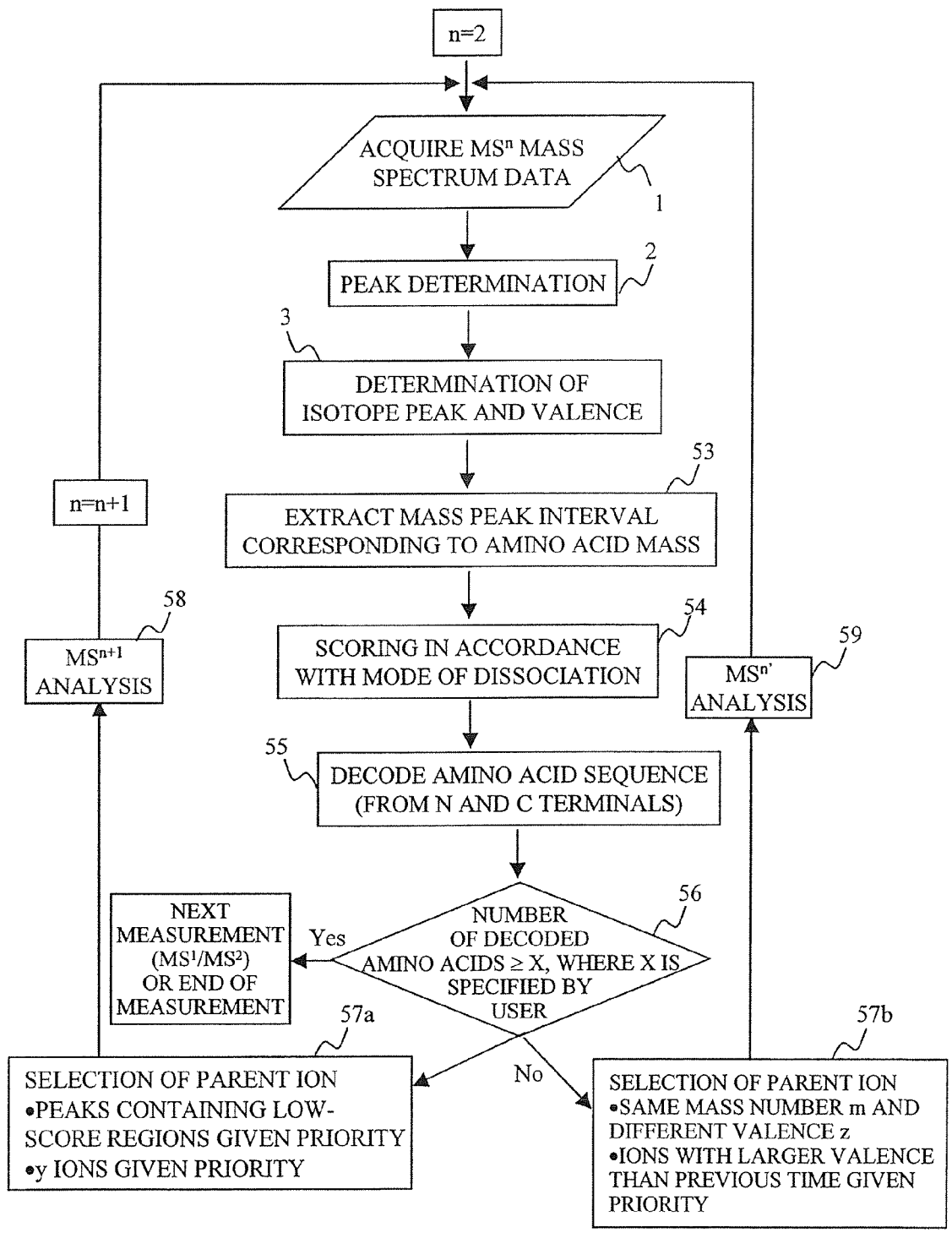
FIG. 36 shows the flow of a system process determination in a $22^{nd}$ embodiment of the invention.

Thus, in accordance with the present invention, the $MS^n$ ($n \geq 2$) data is analyzed on a real-time basis (i.e., during the operation of the mass spectroscopy apparatus), and then the content of next analysis is determined based on such analysis, so that the analysis flow can be optimized. By "on a real-time basis" herein is meant the analysis is performed within a preparation time or transition time $\Delta Tp$ between the time when the MS spectrum data is obtained and the time when the next analysis starts (such as, for example, 100 msec, 10 msec, 5 msec, or 1 msec). FIG. 35b shows a flowchart of the present embodiment where tandem mass spectroscopy is employed, starting with the analysis of a protein and ending with its identification. This flow differs from the conventional flow shown in FIG. 35a in that the acquired $MS^2$ mass spectrum data is analyzed during measurement, and the result of analysis is fed back for the determination of the content of the next analysis. The data analysis of the acquired $MS^2$ mass spectrum data during measurement and the determination of the next analysis content based on the result of analysis are implemented in the control unit 17 or data processing unit 15 in the mass spectroscopy system shown in FIG. 2. FIG. 36 shows a detailed flowchart of the processes performed in the data processing unit 15 during the data analysis of the acquired $MS_2$ mass spectrum data during measurement and the determination, which is automatically performed, of the next analysis content based on the result of analysis. As shown in FIGS. 2, 35b, and 36, after the protein sample that has been fragmented by enzyme digestion or the like is separated by LC or GC, the sample is ionized and then subjected to mass spectroscopy ($MS^1$) in the mass spectroscopy unit 13. Based on the result of the mass spectroscopy ($MS^1$), a specific ion (parent ion) is selected, and the parent ion is dissolved in a collision cell 13A (Selection and dissociation 45 of parent ion). The resultant dissociated fragment is subjected to mass spectroscopy ($MS^n$: $n \geq 2$) in the mass spectroscopy unit 13. Then, for the resultant $MS^n$ ($n \geq 2$) mass spectrum data, a peak determination 2 and an isotope peak determination 3 are conducted in the control unit 17 or data processing unit 15, as shown in FIG. 36. Further, a peak interval extraction 53 corresponding to the mass number of a particular amino acid is carried out, and then a scoring 54 is carried out in terms of the mode of dissociation (such as, for example, a ion, b ion, c ion, x ion, y ion, and z ion) or based on the degree of correspondence to the mass number derived from a particular amino acid sequence, followed by a decoding 55 of the amino acid sequence. Amino acids that have been decoded herein refer to those amino acids with scores in the scoring 54 that exceed a certain designated value. Thereafter, the content of the next analysis is determined in accordance with the number of the decoded amino acids (56). If the number of decoded amino acids exceeds a certain designated number, it is assumed that sufficient information necessary for analysis is contained in the $MS^n$ ($n \geq 2$) mass spectrum data, and the $MS^1$ of the next elation sample, or the $MS^2$ measurement of another parent ion is terminated. On the other hand, if the number of the amino acids that could be decoded does not reach the designated number, it is assumed that the information necessary for analysis is not sufficiently contained in the $MS^n$ ($n \geq 2$) mass spectrum data and a selection 57a, 57b of a specific dissociation ion (precursor ion) is automatically performed, and the ion is subjected to the $MS^{n+1}$ ($n \geq 2$) analysis or $MS^{n'}$ ($n \geq 2$) analysis is performed. The $MS^{n'}$ analysis herein refers to the repetition of the $MS^{n'}$ analysis in the event that the peak of an ion species with substantially the same mass number m and a different valence z from those of the parent ion that has been selected and dissociated during the acquisition of the $MS^{n'}$ data is observed in the $MS^{n-1}$ spectrum data, in which repetition that ion species is selected as the parent ion. In the $MS^{n+1}$ ($n \geq 2$) analysis or $MS^{n'}$ ($n \geq 2$) analysis, different standards are employed in the automatic selection of the parent ion (57a, 57b). In the case of the $MS^{n+1}$ ($n \geq 2$) analysis, the parent ion is selected by giving priority to those of the peaks containing amino acids and with lower scores allocated in the scoring 54 that have a greater m/z or mass number, or to y ions. In the case of the $MS^{n'}$ ($n \geq 2$) analysis, the parent ion should preferably be selected from those ion species with substantially the same mass number m and a different valence z from those of the parent ion that has been selected and dissociated during the acquisition of the $MS^n$ data. If possible, the parent ion should preferably be selected from ions with a greater valence than that of the parent ion that has been selected during the $MS^n$ analysis. This is because of the knowledge that the greater the valence, the more dissociation fragments can be obtained (V. H. Wysocki, G. Tsaprailis, L. L. Smith and L. A. Breci, J. Mass Spectrom. 35, 1399 (2000)).

Preferably, when performing the $MS^{n+1}$ analysis or $MS^{n'}$ analysis, in cases where the valence of the parent ion of the $MS^n$ mass spectrum data to be analyzed is 1 and its mass number is Mp, the $MS^{n'}$ analysis is preferentially performed if an ion peak is being detected in the $MS^{n-1}$ mass spectrum data that has a mass number Mp and a valence of 2 or more, by using the ion species of that ion peak as the parent ion. If the valence of the parent ion in the $MS^n$ mass spectrum data is already 2 or more, preferably the $MS^{n+1}$ analysis should preferentially be performed. This is in consideration of the following hypothesis. Namely, when the valence is 1, if a basic amino acid such as arginine (R) or lysine (K) is included in the sequence, protons are strongly strapped by such a basic amino acid, and many peptides do not have protons (mobile protons) that can freely move around within the main chain of the amino acid sequence. These mobile protons are said to have a large influence on the dissociation of the bond between amino acids (see the above-cited reference). Peptides that do not have a mobile proton are hard to be cut, resulting in the $MS^2$ spectrum data tending to have a smaller number of dissociation ion peaks. On the other hand, in the case of a multivalent ion, to which a plurality of protons are attached, even if one proton $H^+$ is strongly trapped by the basic amino acid, other protons $H^+$ are more likely mobile protons that can move around, so that the probability of the peptide being dissociated at each bond between the amino acids increases. The selection of the $MS^{n+1}$ analysis or the $MS^{n'}$ analysis may be made by the user via the user input unit. The result of determination in the control unit 17 or the data processing unit 15 is utilized through an overall control unit 17 as the next analysis information. Depending on the next analysis information, operation conditions, such as the voltage applied to the mass spectroscopy unit 13, are automatically optimized by the overall control unit 17.

Figure 37:
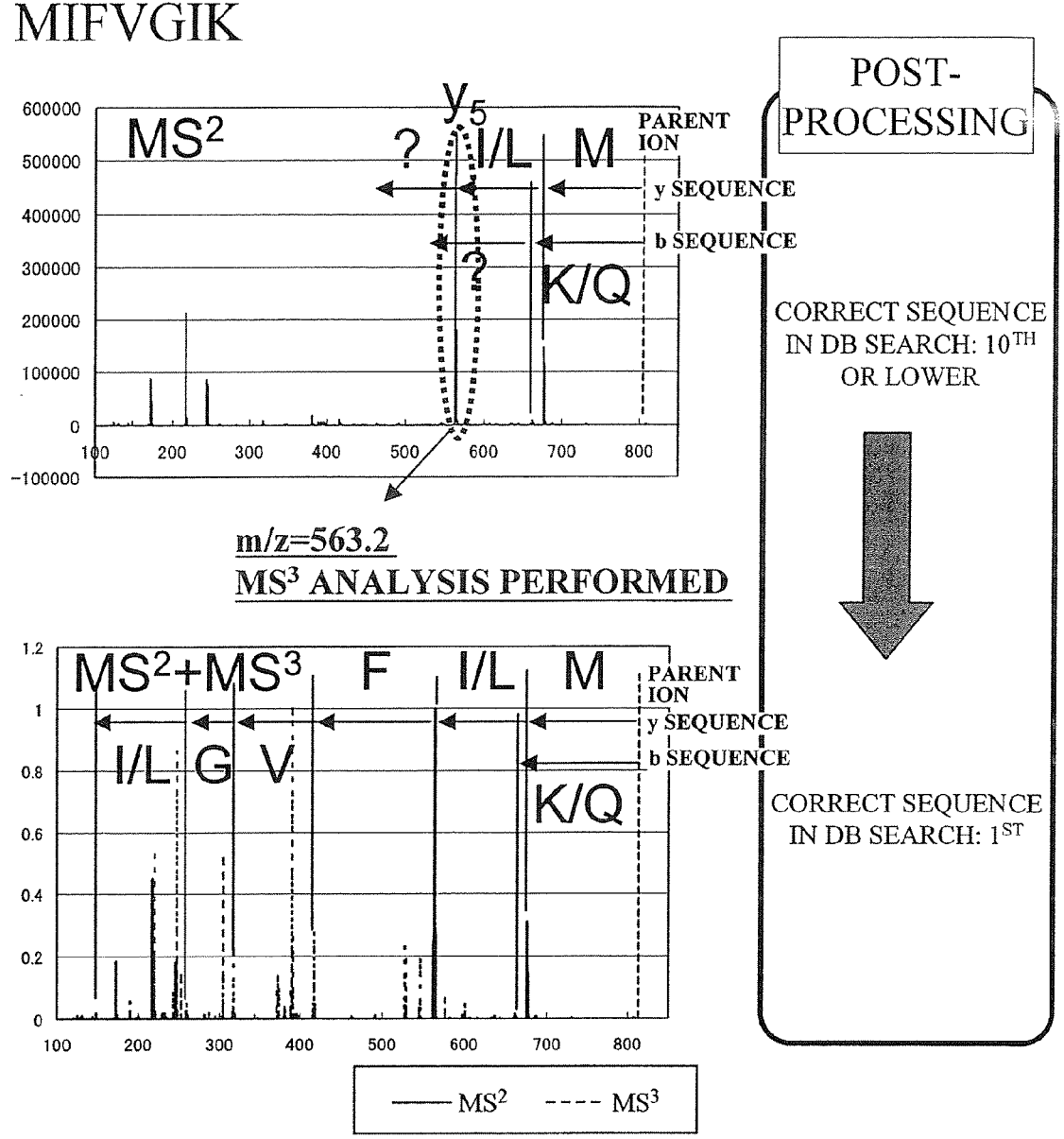
FIG. 37 shows an example of the result of analysis in the $22^{nd}$ embodiment of the invention.

With reference to FIG. 37, an example is described where the identification accuracy is improved by performing mass spectroscopy in accordance with the flow of the invention.

In this embodiment, of the processes performed in the data processing unit 15, the MS$^n$ (n≧2) mass spectrum analysis process (the determination of isotope peaks and valence, the decoding of the amino acid sequence, and the determination of the next analysis content in the case where the number of amino acids that has been decodes does not reach a certain value) is performed within 10 msec (or 100 msec). A sample 41 introduced from an introduction unit was separated (42) by LC and then ionized (43) in an ionization unit. As the ionization method, the ESI (electro-spray ionization) process was used. The ionized sample was then subjected to mass spectroscopy (MS$^1$) in the mass spectroscopy unit (44). Of the ions that were detected in an ion detection unit, specific ions (with m/z=808) were subjected to the selection and dissociation in the ion trap (45), and mass spectroscopy (MS$^2$) was performed (46). On the obtained MS$^2$ mass spectrum data (47), the peak determination 2, the determination of isotope peaks and valence, the elimination of isotope peaks 3, and the conversion of valence were performed, and thereafter the decoding 53 of the amino acid sequence was conducted. In the present embodiment, the number of amino acids that are decoded for the determination was set to be 5. If the number of the amino acids that have been decoded is less than 5, the MS$^3$ analysis (58) or the MS$^{2'}$ analysis (59) is performed. During the decoding of the amino acids, it is first determined (53) whether the mass peak interval corresponds to the mass number of the amino acid within a certain range of tolerance. If it does correspond, it is next determined what type of dissociation the corresponding peak of the ion has (54). In the present system, a score is given depending on the type (such as a ion, b ion, c ion, x ion, y ion, or z ion) of dissociation of the detected ion such that the types of ion that are more likely detected are allocated higher scores. For example, when the dissociation method is CID, b ion and y ion are given higher scores, and when the dissociation method is ECD, c ion and z ion are given higher scores. The tolerance for the mass and the scoring parameters can be changed by the user depending on various conditions, such as the type of the apparatus and the method of dissociation. Moreover, in cases where the likelihood of dissociation occurring between the amino acid sequences (the ease with which they are cut) is evaluated in advance in an experiment or simulation, that information may be used as a database for the decoding of the amino acid sequence. In that case, since the information about the intensity of the mass spectrum data can be incorporated during the determination, the decoding of the amino acid sequence can be more accurately performed. Thereafter, with regard to the mass peak interval that is within the tolerance and that has been determined to be possessing a score that exceeds a certain value, the decoding of the amino acid (55) is performed based on the m value of the parent ion, starting from both the N and C terminals of the peptide, and the number of amino acids that have actually been decoded is derived.

In the present system, after the elimination of isotope peaks, the determination of valence, and the conversion of the valence value are performed on the resultant MS$^2$ mass spectrum data in the data processing unit 15, the amino acid sequence is decoded. In this system, it is then determined if the number of the amino acids that have been decoded reaches a specified value (56). If not, the next analysis content is determined based on either the MS$^3$ analysis or the MS$^{2'}$ analysis. Whether the MS$^3$ analysis or the MS$^{2'}$ analysis should be performed may be designated by the user at the beginning. In the present example, the system is set such that the MS$^3$ analysis is selected as the next analysis. If the routine should proceed to the MS$^3$ analysis (58), a peak with a low-score region (estimated amino acid) is preferentially selected as the parent ion (57a). When the dissociation method is CID, peaks that can be thought to be y ions are preferentially selected. This is due to the fact that, in an enzymatic digestion by tryptin, arginine (R) or lysine (K), which readily trap protons, is located at the C terminal, making it easier for y ions to be detected with high intensity. On the other hand, in the case of the MS$^{2'}$ analysis (59), although the MS$^2$ analysis is performed once again on the ion with the same mass number m and a different valence z, if there is an ion with a larger valence z, that ion is preferentially selected as a precursor ion (57b). If bivalent ions are selected as precursor ions, most of the resultant dissociation fragments would be detected as monovalent, so that the data analysis in a post-processing step would be easier. If the valence of the ion analyzed in the MS$^2$ analysis is monovalent, bivalent ions are preferentially selected as precursor ions for the MS$^{2'}$ analysis. When the MS$^{n+1}$ (n≧3) is repeated, depending on the analysis result, the mass number of the precursor ion gradually decreases. Therefore, the user may be allowed to choose, via the user input unit, to change the number of the decoded amino acids to be determined depending on the mass number of the parent ion, or to proceed to the next measurement or end the measurement if the mass number of the parent ion drops below a predetermined value.

In the present embodiment, an ion with m/z=563.2 was selected as the parent ion for the MS$^3$ analysis. The thus selected ion was dissociated and then subjected to the MS$^3$ analysis. When the amino acid sequence decoding process was performed again on the resultant MS$^3$ mass spectrum data, seven amino acids were decoded. In the present embodiment, it took not more than 10 msec for any of the mass spectrum analysis processes, suggesting that the mass spectrum can be evaluated and determined on a real-time basis during the measurement of the mass spectrum data. As shown in FIG. 37, the MS$^2$ mass spectrum data per se, and mass spectrum data obtained by mixing the MS$^2$ mass spectrum data and the MS$^3$ mass spectrum data was subjected to analysis using a database search software (MASCOT) (due to the fact that the current database is only adapted for the MS$^2$ mass spectrum data). In the analysis using the MS$^2$ mass spectrum data, the correct sequence (MIFVGIK) was ranked below the 10$^{th}$ place. In the analysis using the MS$^2$/MS$^3$ mixed mass spectrum data, however, the correct sequence was ranked first. These results indicate that the identification accuracy of a measurement target can be improved by the present invention.

In accordance with the invention, for the MS$^n$ mass spectrum data in which the amino acid sequence can be decoded with more than a certain value, the routine proceeds to the measurement of the next sample (MS$^1$ or MS$^2$ using another ion as the parent ion) instead of performing the MS$^{n+1}$ or MS$^{n'}$ analysis. Thus, wasteful measurement can be avoided and analysis can be performed with a high throughput. Further, the invention can be applied to any compounds with equivalent effects as long as the compounds have a limited kinds of basic structures as structural units, such as proteins with sugar chains or modifying structures, or polymers.

(Real-Time Database Search)

Figure 38:
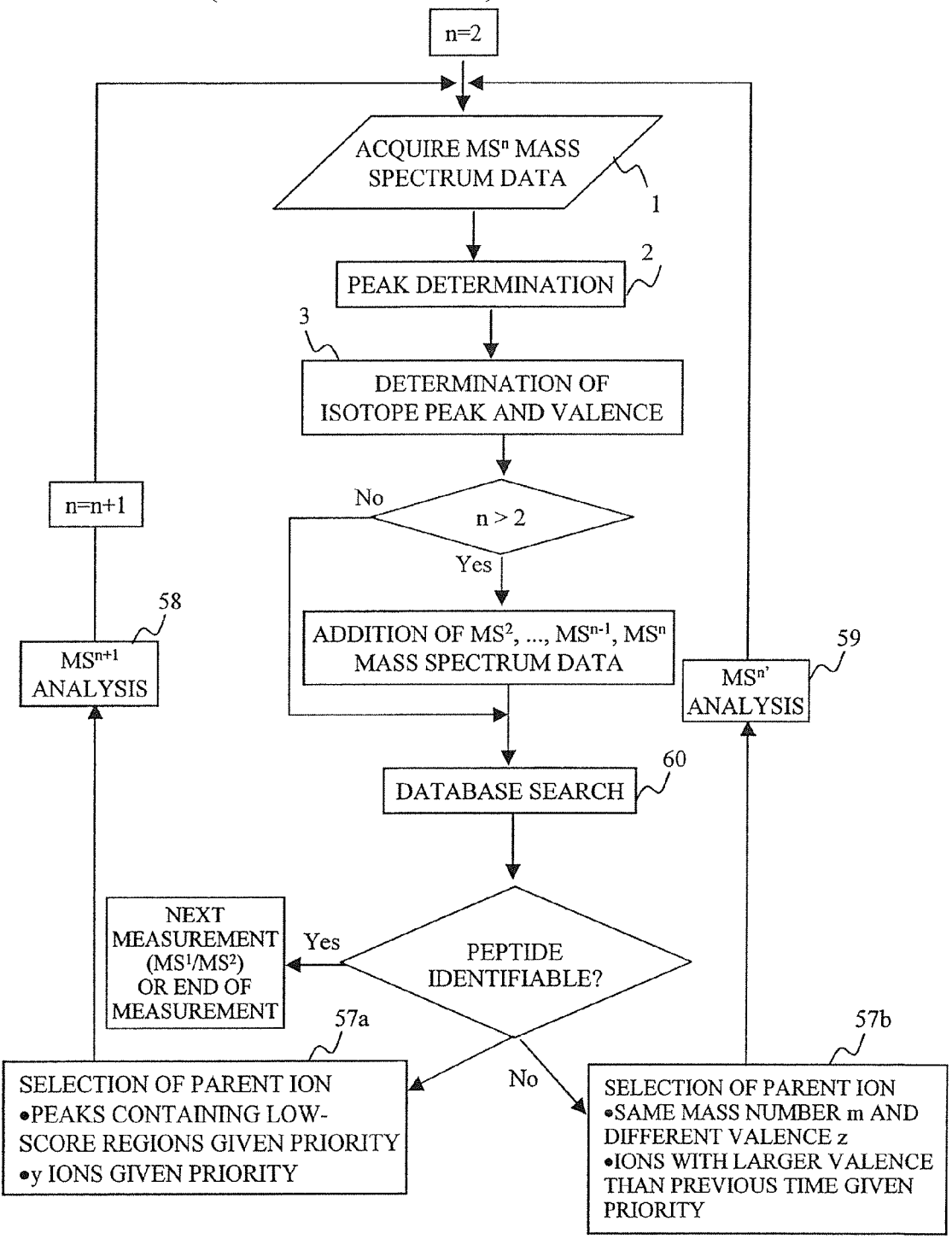
FIG. 38 shows the flow of a system process determination in a $23^{rd}$ embodiment of the invention.

A 23$^{rd}$ embodiment of the invention will be described in the following. For the identification of proteins, methods that utilize a de novo peptide sequence process and methods that utilize a database search are available, of which a database search method will be described below. In the present embodiment, a database search is conducted on the MS$^n$ mass spectrum data obtained on a real-time basis. FIG. 38 shows a flowchart of the processes performed in the present embodiment. On the $MS^n$ ($n \geq 2$) mass spectrum data that is obtained, a database search is conducted on a real-time basis during measurement, using a large database that stores the mass numbers of the peptide sequences obtained by enzymatically digesting the sequences of many of the known proteins that are registered in public databases, for example, and the mass numbers of all of the dissociation fragment peptides predicted from such peptide sequences. By "on a real-time basis" herein is meant that the $MS^n$ ($n \geq 2$) mass spectrum analysis process (the determination of isotope peaks and valence, the database search 60, and, in the case where n>2, the addition of the $MS^2$ mass spectrum data and $MS^n$ mass spectrum data) is performed within 10 msec (or 100 msec). If in the database used for the database search 60 there is only data available that corresponds to the $MS^2$ mass spectrum data, the $MS^n$ ($n \geq 2$) mass spectrum data must be added to the $MS^2$ mass spectrum data. In the database search that is performed in a conventional post-processing step, the search takes approximately one minute per spectrum. However, real-time analysis can be realized by adopting a parallel computer or a PC cluster in the data processing unit 15 in order to process data in a parallel manner, or by dividing the database so that the database search can be performed in a parallel manner and at higher speed.

(Specific Conditions→$MS^3/MS^{2'}$)

Figure 39:
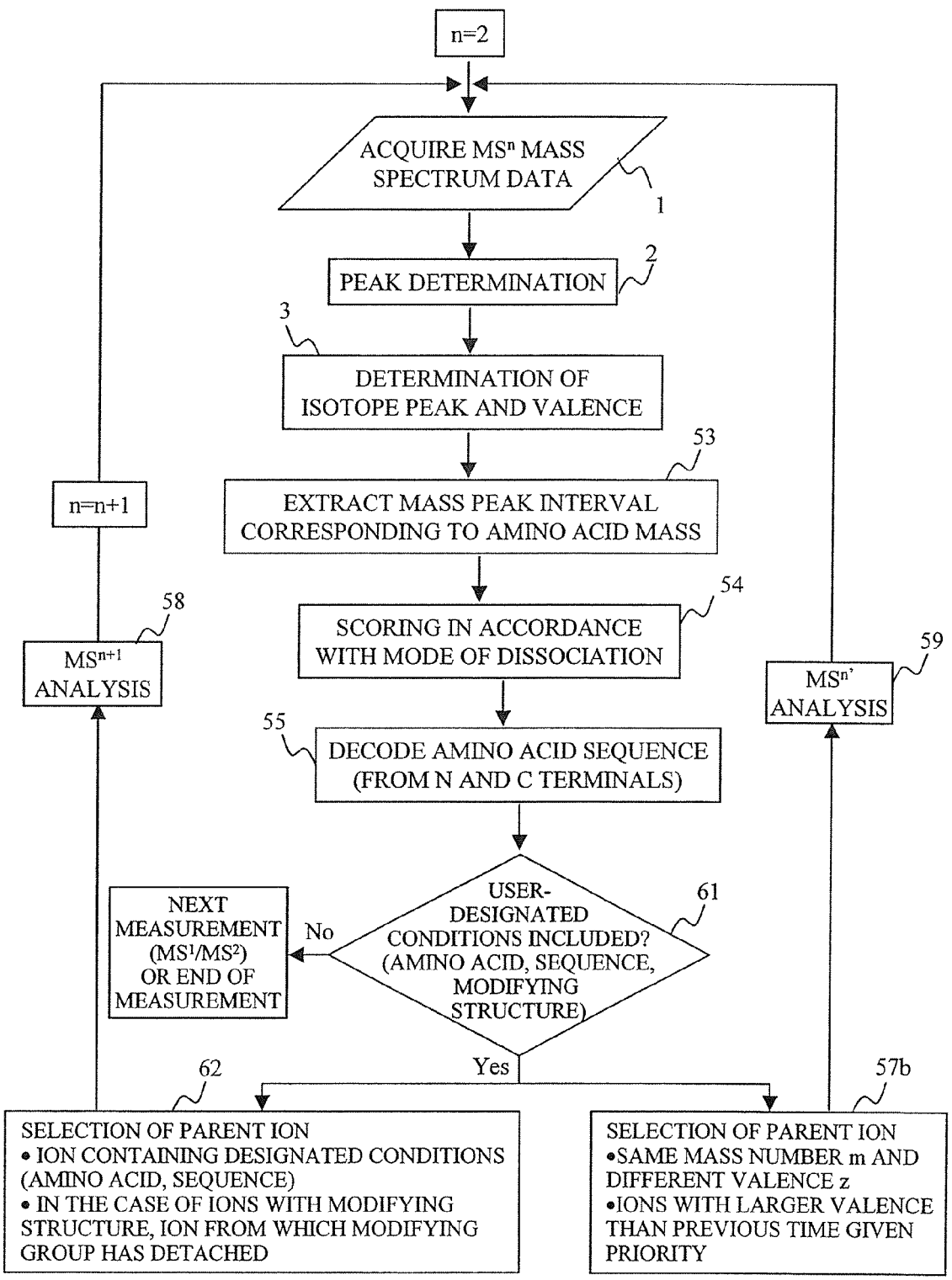
FIG. 39 shows the flow of a system process determination in a $24^{th}$ embodiment of the invention.

A 24$^{th}$ embodiment of the invention will be described in the following. FIG. 39 shows a flowchart of the processes performed in a system according to the present embodiment. In this embodiment, if the $MS^n$ data that has been real-time analyzed satisfies conditions specified by the user, for example, the $MS^{n+1}$ analysis or the $MS^{n'}$ analysis is performed. Table 1 shows the mass number of individual amino acid residues, and the mass number of dipeptides in which two amino acids similar to the individual amino acid residues are bonded.

TABLE 1

| Single amino acid residue | Mass number (Da) | Double amino acid residue | Mass number (Da) |
|---|---|---|---|
| Trp | 186.2 | Glu-Gly | 186.2 |
|  |  | Ala-Asp | 186.2 |
|  |  | Ser-Val | 186.2 |
|  |  | Lys-Gly | 185.2 |
|  |  | Gln-Gly | 185.2 |
|  |  | Asn-Ala | 185.2 |
| Asn | 114.1 | Gly-Gly | 114.1 |
| Lys | 128.2 | Gly-Ala | 128.1 |
| Gln | 128.1 | Gly-Ala | 128.1 |
| Glu | 129.1 | Gly-Ala | 128.1 |
| Arg | 156.2 | Val-Gly | 156.2 |

It will be seen from Table 1 that the mass number of lysine (Lys) and that of a dipeptide (Gly-Ala or Ala-Gly) consisting of glycine (Gly) and alanine (Ala), for example, are substantially identical and would be indistinguishable in equipment with low resolution. Thus, in the real-time analysis of the $MS^2$ ($n \geq 2$) mass spectrum data in Embodiment 22 (real-time de novo), if it is determined that there is the possibility that the data could include an amino acid, such as Lys, whose mass number is expected to be equal to the sum of the mass numbers of two amino acid residues, the $MS^{n+1}$ analysis or the $MS^{n'}$ analysis can be automatically performed. Table 2 shows examples of the chemical modifications of amino acids.

TABLE 2

| Type of chemical modification | Δm (Da) |
|---|---|
| Formylation | 28.01 |
| Phosphorylation | 79.98 |
| Acetylation | 42.04 |
| Myristylation | 210.36 |
| Hydroxylation | 15.99 |
| Glycosylation (when the sugar is hexose) | 162.14 |

As shown in Table 2, if there is the possibility that a modifying structure, such as a phosphoric acid, is attached to the amino acid, the $MS^{n+1}$ analysis or $MS^{n'}$ analysis can be performed by using a peak from which the modifying structure is detached as a parent ion. A sequence, such as glycine (Gly)-glycine (Gly), that is considered to tend to not produce dissociation (i.e., that is considered to be hard to be cleaved) is inputted in the sequences in advance, and it is then determined if there is the possibility the aforementioned sequence, or a sequence designated by the user, is contained (61). It is determined that there is the possibility that the particular amino acids or sequence is contained, ions that contain such amino acids or sequence are selected as a parent ion (62) and then the $MS^{n+1}$ analysis or $MS^{n'}$ analysis can be performed. These conditions may be entered by the user via the user input unit. By performing the $MS^{n+1}$ analysis or $MS^{n'}$ analysis only when specific conditions specified by the user are satisfied, tandem mass spectroscopy data can be obtained that contains more detailed structural information. Moreover, the amino acid sequence analysis method according to the present embodiment may be performed in a post-processing step, rather than on a real-time basis. Generally, when analysis is performed on the entire data including those mass spectrum data with smaller amounts of information and with lower reliability in a database search, not only does it take longer for the search but also there is the possibility of identifying pseudo-positive proteins. Thus, it is better in some cases to eliminate mass spectrum data with lower reliability. By so doing, it would become possible to evaluate, using the amino acid sequence analysis method of the present embodiment, if particular data in a huge amount of data contains a large amount of information and whether or not it is highly reliable. In this way, only mass spectrum data with high reliability could be used for the database search, so that analysis could be performed more reliably and at higher speed than possible by conventional techniques.

(Determination by the Number of Peaks and by Peak Groups)

Figure 40:
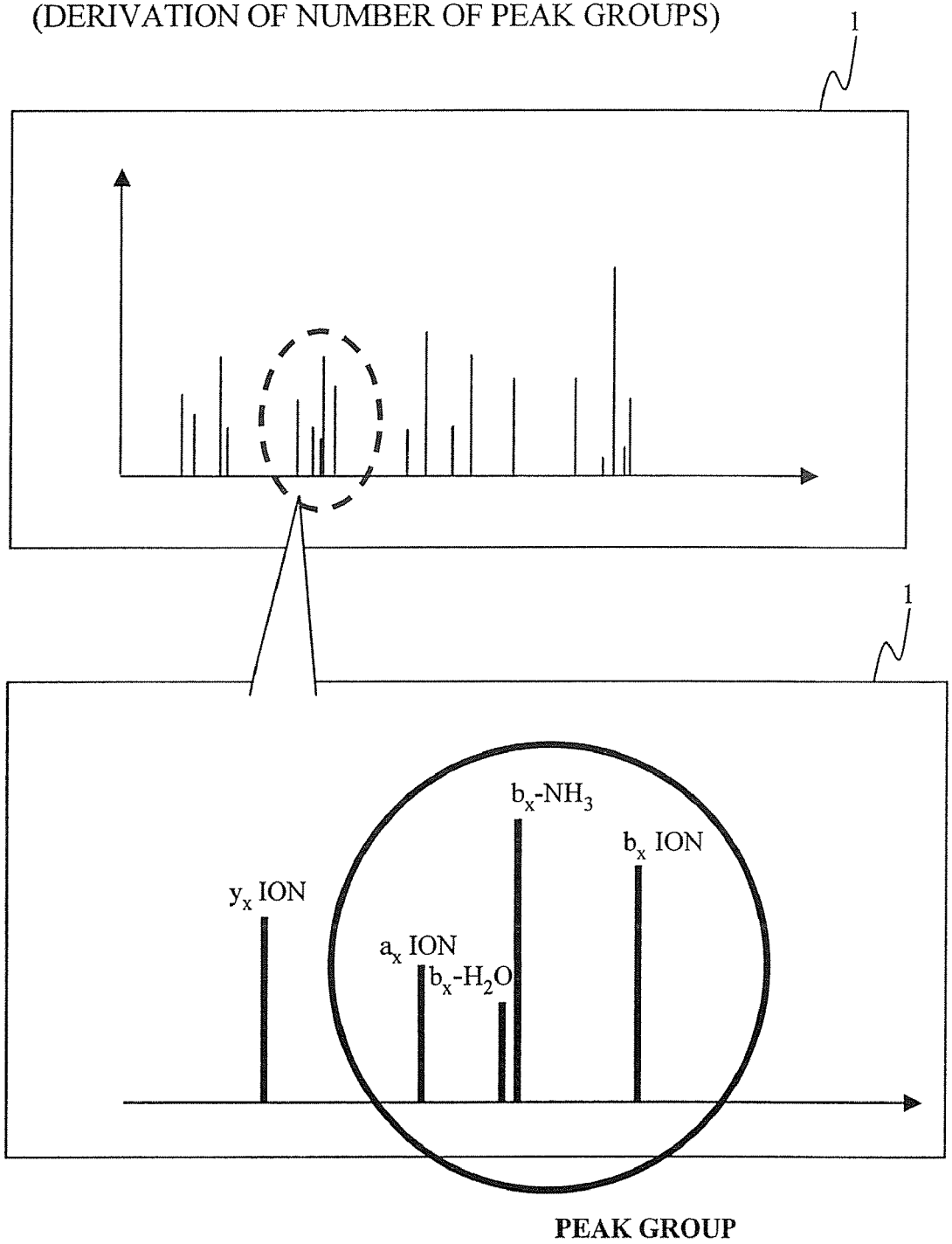
FIG. 40 shows the concept of a peak group in a $25^{th}$ embodiment of the invention.
Figure 41:
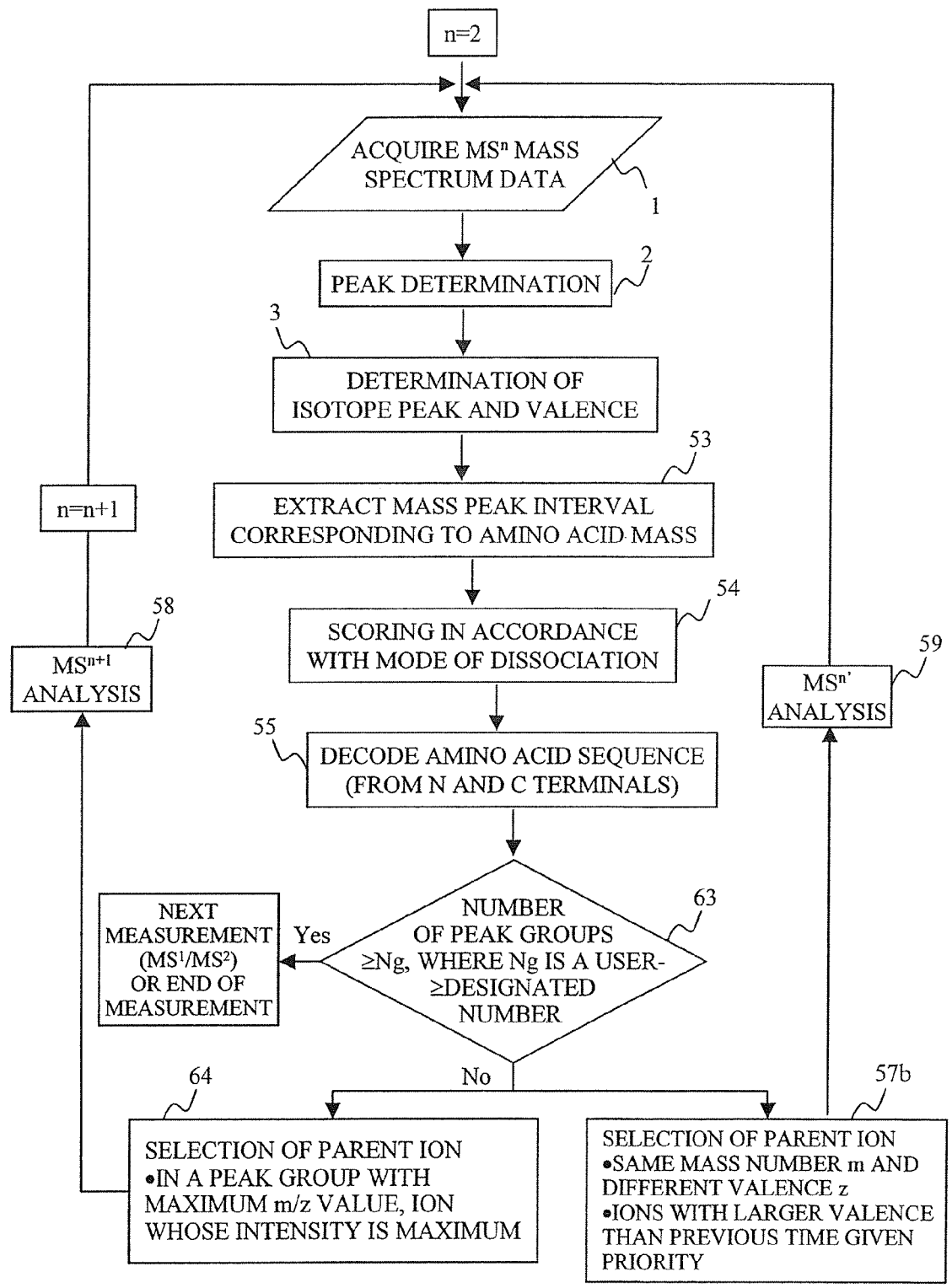
FIG. 41 shows the flow of a system process determination in a $25^{th}$ embodiment of the invention.
Figure 42:
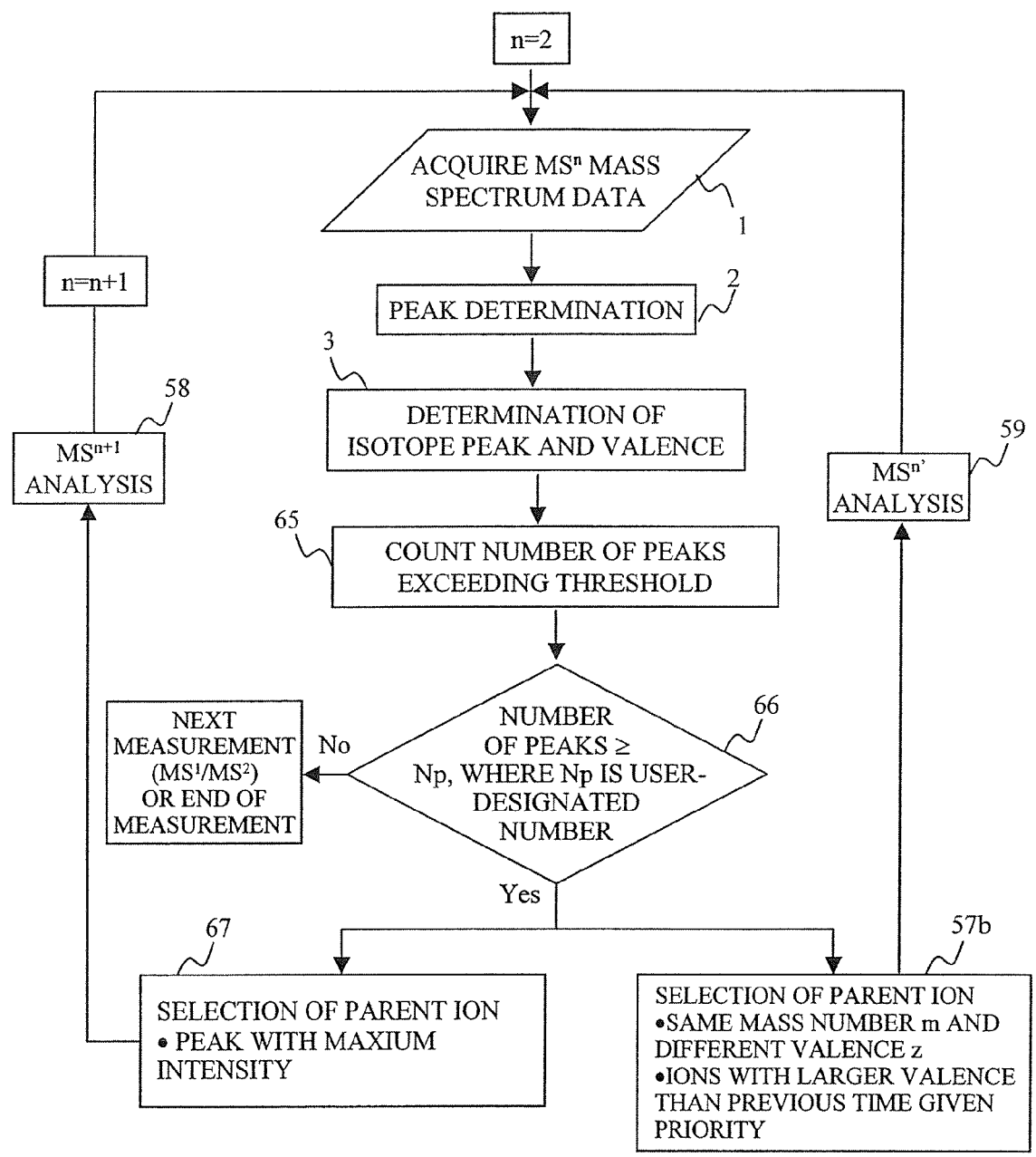
FIG. 42 shows the flow of a system process determination in a $25^{th}$ embodiment of the invention.

Hereafter a 25$^{th}$ embodiment of the invention is described with reference to FIGS. 40 to 42. FIGS. 41 and 42 show flowcharts of a system according to the present embodiment. When a peptide is analyzed using a database search, even if not all of the dissociation fragments predicted from the amino acid sequence of the peptide are obtained, the peptide can be identified as long as a certain number of peaks of fragment ions are obtained. Thus, the amount of information possessed by the mass spectrum data can be determined based on the number of peaks of the dissociation fragment ions. As shown in FIG. 40, when one or more mass peaks are detected that are inferred to be derived from an amino acid, such as a dehydration peak or deammoniation peak from the peaks inferred from the decoded amino acid sequence, these peaks are processed as consisting of one and the same kind, and then the number of such groups of peaks of the same kind is derived. Alternatively, a group of peaks that appear in a range of m/z (such as the range of m/z=+40 with respect to the m/z value of the peak of b ion or y ion, for example) in which the possibility of appearance of dehydration peaks or deammoniation peaks derived from a single amino acid is high may be processed together, and then the number of such peak groups may be obtained. It is then determined in a determination 63 whether or not the number of such peak groups exceeds a certain number or no. If it does, the mass spectrum data is considered to contain an amount of information necessary for identification, and then the measurement ($MS^1$, or $MS^2$ using another ion as a parent ion) of the next sample is performed, or the measurement comes to an end. The number of the peak groups may be entered via the user input unit. On the other hand, if the number of the peak groups does not reach the certain number, the $MS^{n+1}$ analysis or the $MS^{n'}$ analysis is performed. In this case, in a selection 64 of the parent ion for the $MS^{n+1}$ analysis, of those peak groups in which the interval between the individual peak groups is the largest, a peak with a strong intensity is selected from the group of peaks with large m/z values. In this way, the $MS^{n+1}$ analysis can be performed on ions containing some portions of which peaks are not detected and in which the amount of information is small, so that the accuracy of identification can be expected to improve. This determination is not performed on the peak groups; rather, the number of peaks with values exceeding a certain threshold is determined (65), and it is then determined if the number of such peaks is more than a certain number (66). If the number of the peaks is more than the certain number, it is assumed that the mass spectrum data contains sufficient amount of information necessary for identification, and the measurement of the next sample ($MS^1$, or $MS^2$ using another ion species as the parent ion), or the measurement comes to an end. On the other hand, if the number of the peaks does not reach the certain number, the $MS^{n+1}$ analysis or the $MS^{n'}$ analysis is performed. In this case, in a selection 67 of the parent ion for the $MS^{n+1}$ analysis, simply a peak with the strongest intensity is selected as the parent ion. In this way, the $MS^{n+1}$ analysis can be performed on the ions containing portions of which the peaks are not detected and with a small amount of information, so that the accuracy of identification can be expected to improve. The threshold value and the number of peaks may be designated by the user via the user input unit.

(Sugar Chain as the Object of Measurement)

A $26^{th}$ embodiment of the invention will now be described. When the sample is a sugar chain, its structural unit is a monosaccharide. Thus, in the analysis of the $MS^n$ mass spectrum data, the relevant monosaccharide is inferred from the mass peak intervals. In this embodiment, as in Embodiment 22 (real-time de novo), the $MS^n$ mass spectrum data on which the elimination of isotope peaks, the determination of valence and the conversion of valence have been performed is processed to extract the peak intervals within a certain tolerance range or with a score of more than a certain value, and then the number of monosaccharides that can be decoded from the terminal of the sugar chain is derived. When the number of the monosaccharides that have been decoded is more than a certain value specified by the user, for example, the measurement of the next sample is conducted, or the measurement is terminated. On the other hand, if the number of the monosaccharides that have been decoded does not reach the certain value, the $MS^{n+1}$ analysis or the $MS^{n'}$ analysis is performed. As the parent ion for the $MS^{n+1}$ analysis, peaks containing regions with lower scores are preferentially selected. The above-described processes are carried out within the real-time of measurement (such as within 10 msec or 100 msec), and an optimum analysis flow is automatically selected.

Figure 46:
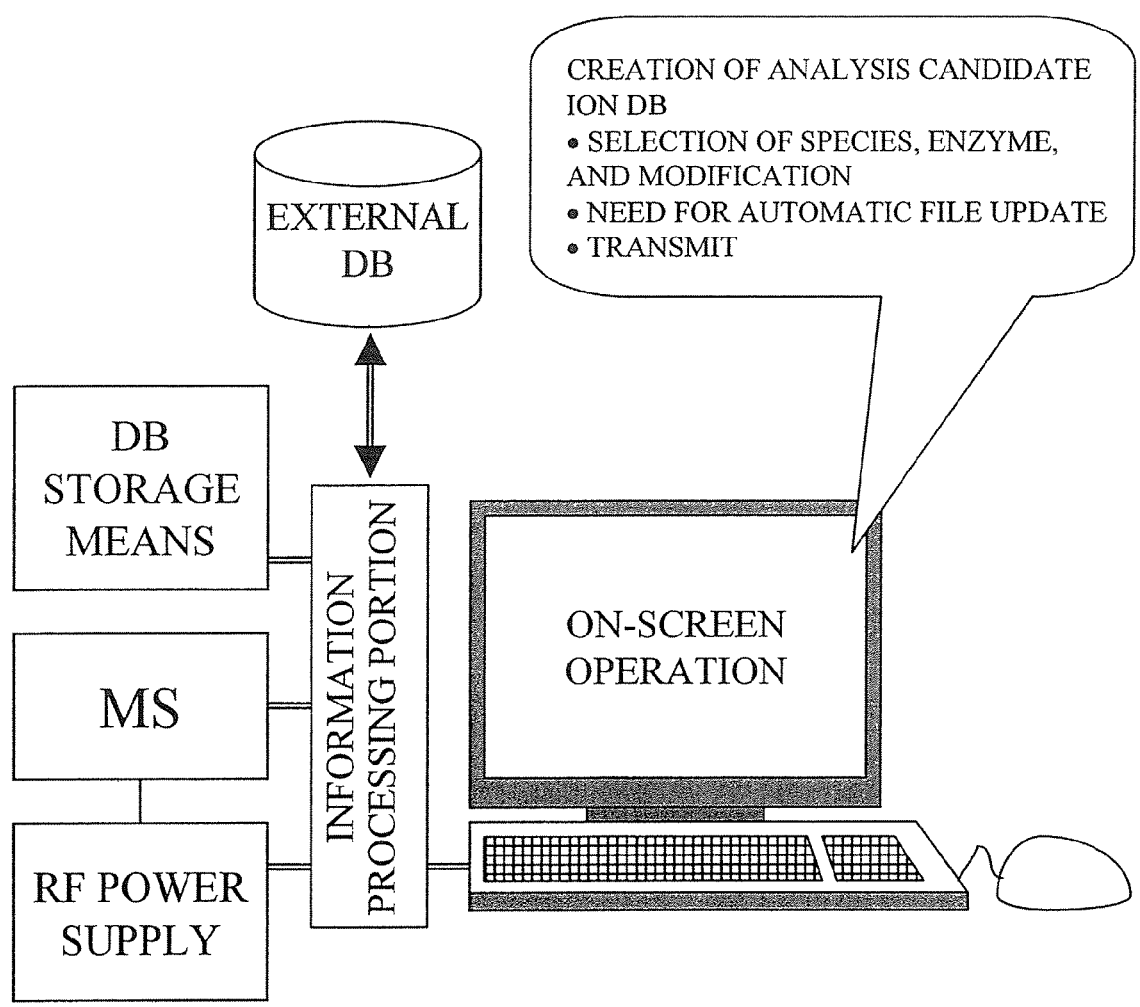
FIG. 46 shows the system configuration of a mass spectroscopy system according to an embodiment of the invention.

FIG. 46 shows a system based on an embodiment of the mass spectroscopy system of the invention. An input operation for a first database concerning the analysis object ion is conducted on a terminal device such as a personal computer. If it is necessary to create a file for a new database, while the mass of ion (or m/z, where m is the mass of ion and z is ion charge) may be directly entered on the computer screen, it is also possible to select and enter information (such as the category of the species (such as humans), the digestive enzyme, the presence or absence of modification, organs, etc.) for utilizing external databases. In the latter case, it is also possible to create or update the database using a server to which an external database of genes or proteins has been downloaded, or via the Internet. When existing databases are utilized, a first database is determined by, for example, selecting from a list of existing databases on the screen. After necessary input information about the first database has been entered, a transmit input is performed. By these operations, the first database in which the candidate substances as analysis targets are recorded is stored in a database storage unit. In an actual analysis, in order to make it difficult for the ions of substances that are not listed in the first database to be detected, an instruction for controlling the RF voltage to be applied to the mass spectrometer (MS) may be transmitted from the information processing unit to the RF voltage power supply before the primary mass spectroscopy is performed. In this manner, before any ion of a substance that is an analysis target candidate listed in the first database is detected in the primary mass spectroscopy, the unwanted ion can be discharged. The information about the detected ions is searched for as needed in the first database that is stored in the database storage means. As the number of types of ions that can be the targets for the secondary mass spectroscopy is limited, an instruction is sent from the information processing unit to the power supply involved with CID such that those ions that correspond to the data in the first database are preferentially subjected to the secondary mass spectroscopy (tandem mass spectroscopy). If the ions for which no analysis is necessary are known, a secondary database for recording the data about analysis target candidate substances may be created in the same manner as in the case of the first database, and the secondary database may be used for controlling the RF voltage applied during the primary mass spectroscopy. Further, the information about those ions listed in the first database for which analysis has been completed can be transferred to the second database. By so doing, redundant analysis of the same ion can be avoided, thereby allowing minute samples of more kinds of ions to be analyzed. Identification of a particular substance is performed based on the result of the secondary mass spectroscopy and the information about the parent ion therefor.

Figure 47:
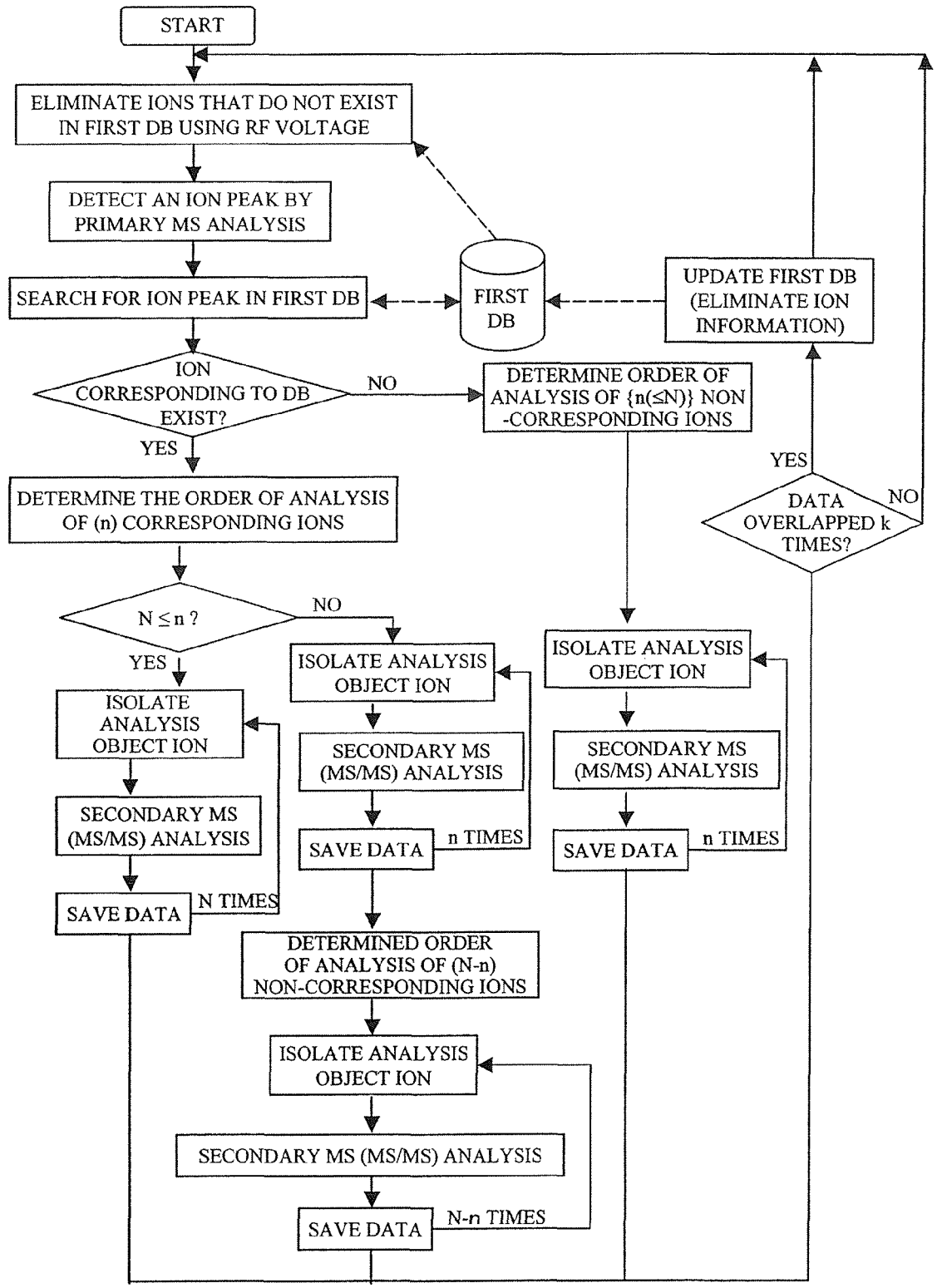
FIG. 47 shows an example of the analysis flow in a mass spectroscopy system based on another embodiment of the invention.
Figure 48:
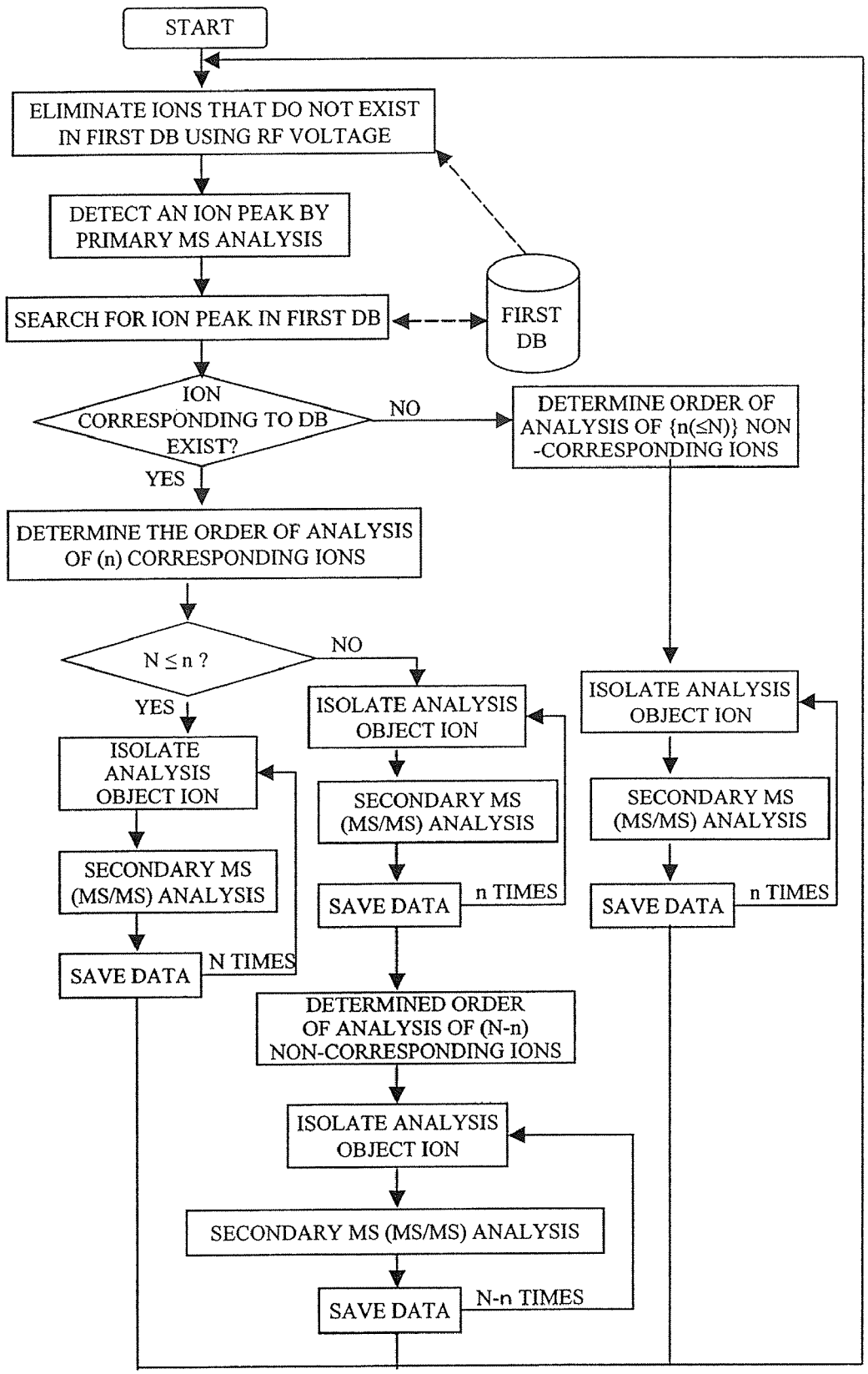
FIG. 48 shows an example of the analysis flow in a mass spectroscopy system based on another embodiment of the invention.

FIG. 47 shows an example of the flow of the aforementioned analysis. In this example, the number of times that tandem analysis can be performed in a single sequence is N, and the information about those ions listed in the first database that have been detected k times is deleted once by updating the first database. Such automatic updating of the database may be designated by an operation on the screen (i.e., an input screen on the display unit) shown in FIG. 46 prior to the start of analysis. When analyzing an extremely minute amount of a target sample, it would be more advantageous to turn off the automatic updating of the first database from the viewpoint of detection of the analysis target sample, as shown in FIG. 48.

Figure 49:
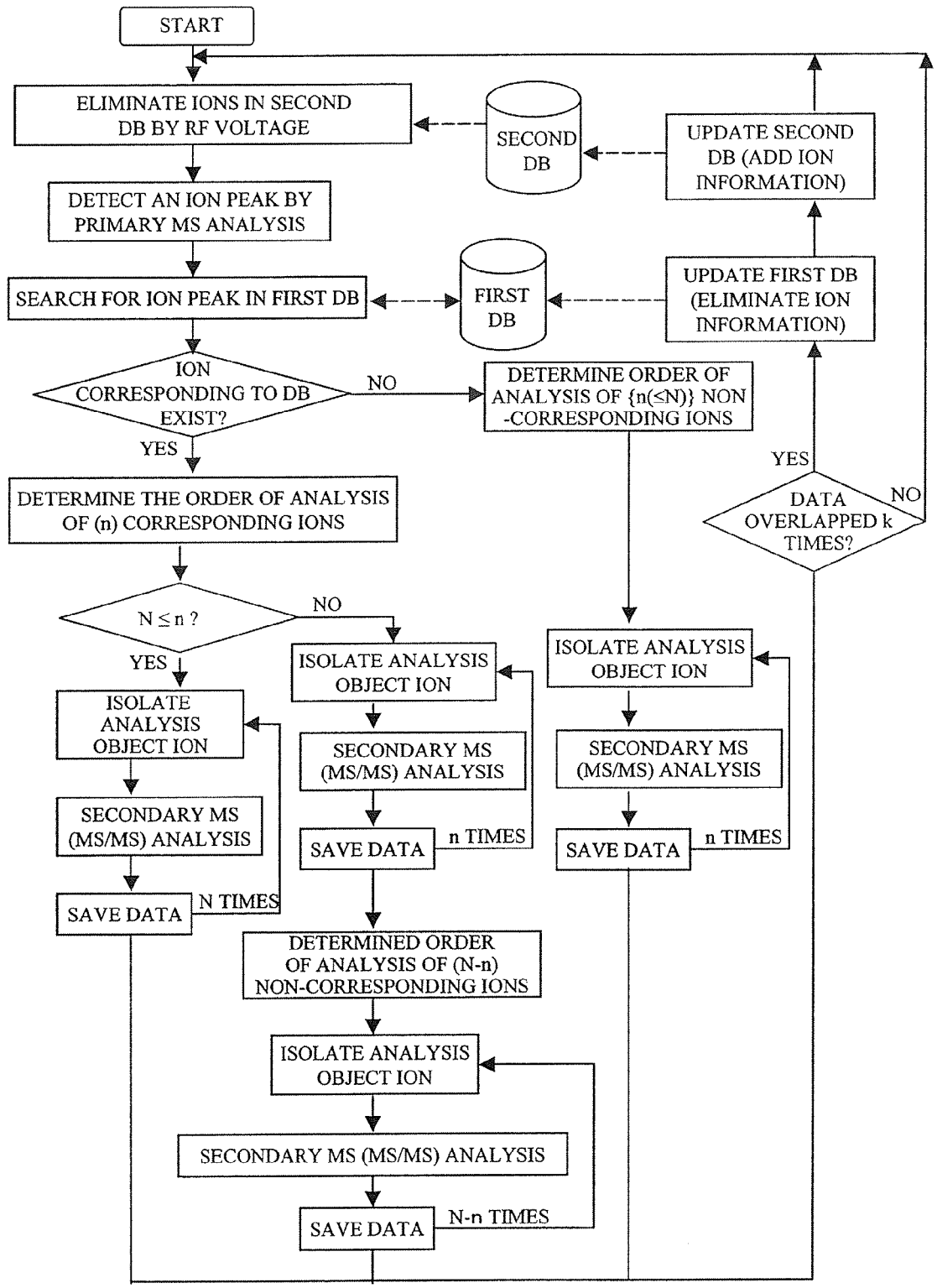
FIG. 49 shows an example of the analysis flow in a mass spectroscopy system based on yet another embodiment of the invention.

FIG. 49 shows the flow of an embodiment in which a second database is provided. When a non-analysis target ion of which the ion intensity is expected to be very strong is known, the information about the non-analysis target ion may be stored in a second database that can be created in the same manner as in the first database, and the information may be usefully used for the control of the RF voltage applied during the primary mass spectroscopy. These settings of the flow may be made by operations on the screen (i.e., input operations on the display unit) shown in FIG. 46.

Figure 50:
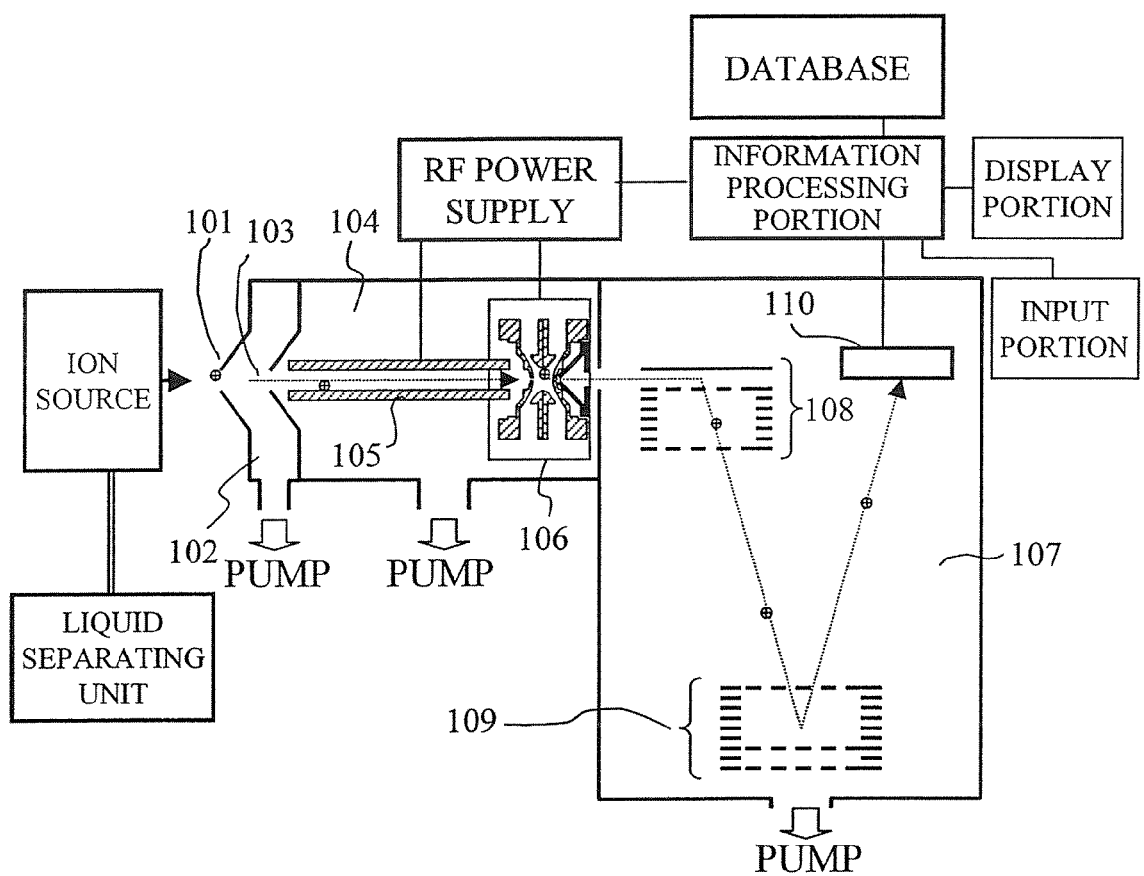
FIG. 50 shows a diagram of a mass spectroscopy system based on yet another embodiment of the invention.

FIG. 50 shows a diagram of an apparatus according to an embodiment of the mass spectroscopy system of the invention. The apparatus comprises a quadrupole ion trap time-of-flight mass spectrometer, which is a combination of a quadrupole ion trap and a time-of-flight mass spectrometer and is described in Analytical Chemistry, Vol. 67 (1995) pp. 234A-242A, for example. However, the present embodiment is unique in that the trajectory of ions discharged from the ion trap is bent at substantially right angle at an acceleration portion of the time-of-flight mass spectrometer. This configuration is adopted so that the spread of energy of ions at the acceleration portion of the time-of-flight mass spectrometer can be reduced and the mass resolution can be improved. A sample solution separated in a liquid separation portion of a liquid chromatograph, for example, is introduced into the ion source where it is turned into a gaseous ion by a spray ionization process, such as the electrospray ionization process or the sonic spray ionization process. The thus generated gaseous ion is then introduced into a differential pumping portion 102 through a pore 101. The gaseous ion is further introduced into a high vacuum portion 104 through a pore 103, where the ion passes through an ion transport portion 105 consisting of a multipole pole, for example, and is then introduced into an ion trap 106. An RF voltage is supplied to the ion trap 106 from an RF power supply such that the gaseous ion is trapped at the center of the ion trap 106 by a quadrupole electric field. With regard to non-analysis target ions, an RF voltage may be applied to the multipole pole in the ion transport portion so that the non-analysis target ions can be removed in the ion transport portion 105.

In the case where no multipole pole is used in the ion transport portion 105, the non-analysis target ions are removed in the ion trap 106, and an RF voltage for trapping the analysis target ions is applied to the ion trap 106. The gaseous ion that has been trapped for a certain duration of time is transported to the right by an electric force and introduced into an ion acceleration portion 108 of the time-of-flight mass spectrometer 107. In the ion acceleration portion 108, a pulsed RF voltage is applied to the introduced gaseous ion at a specific time to thereby accelerate the gaseous ion until it has a certain kinetic energy. The thus accelerated gaseous ion has its trajectory altered by a reflector 109 and thus its energy converged, before it is detected by a detector 110. The length of the ion trajectory between the ion acceleration portion 108 and the detector 110 is constant. Since the ion velocity decreases with increasing m/z (mass/charge number) of the ion, the detector 110 detects ions in the order of increasing m/z values. The output of the detector 110 is led to the information processing unit where the m/z of the ion is determined based on the ion detection time. Based on the thus obtained result of the primary mass spectroscopy, the priority order of the ions as the target of the secondary mass spectroscopy is determined in the information processing unit. Then, in order to apply an RF voltage to the ion trap 106 for isolating only the target ions for the secondary mass spectroscopy from the ions introduced into the ion trap 106, an instruction is sent from the information processing unit to the RF power supply. Further, an instruction for dissociating the isolated ions by CID, for example, is sent from the information processing unit to the RF power supply, so that dissociated fragment ions are produced in the ion trap 106. The fragment ions are transported to the right by an electric force and introduced into the ion acceleration portion 108 of the time-of-flight mass spectrometer 107. In the ion acceleration portion 108, a pulsed RF voltage is applied to the introduced gaseous ion at a specific time to thereby accelerate the gaseous ion until it has a specific kinetic energy. The thus accelerated gaseous ion has its trajectory altered by the reflector 109 and is then detected by the detector 110. The output of the detector 110 is delivered to the information processing unit where the m/z of the ion is determined based on the ion detection time. The secondary mass spectroscopy is thus realized. A certain number of the secondary mass spectroscopy target ions that have been prioritized are sequentially subjected to the secondary mass spectroscopy in accordance with the priority order.

Figure 51:
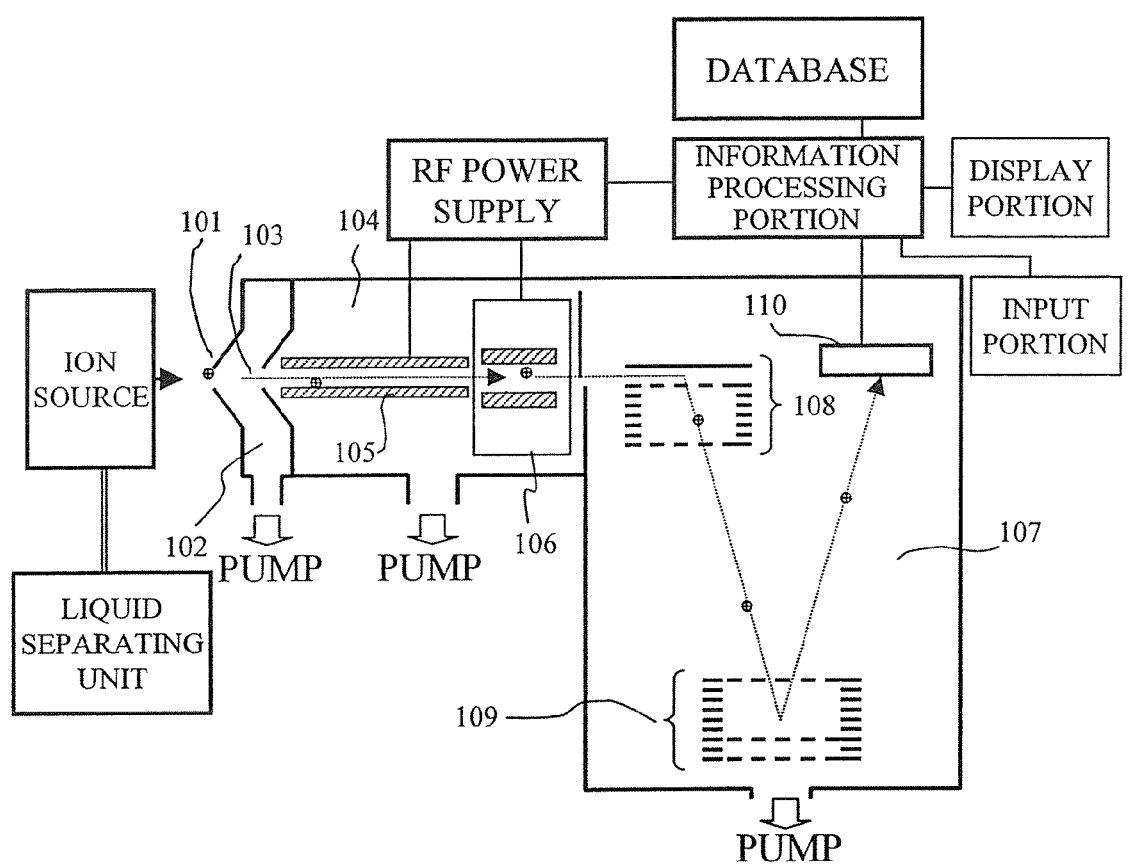
FIG. 51 shows a diagram of a mass spectroscopy system based on yet another embodiment of the invention employing a linear trap.

In the ion trap 106, a linear trap consisting of a quadrupole pole as shown in FIG. 51 may be used instead of the quadrupole ion trap. The linear trap (quadrupole) time-of-flight mass spectrometer per se is described in Rapid Communications in Mass Spectrometry, Vol. 12 (1998) pp. 1463-1474, for example. The present embodiment is substantially equivalent to the quadrupole ion trap shown in FIG. 2 in terms of functionality, but it is characterized in that the amount of ions that can be trapped at one time can be increased. To the linear trap, an RF voltage is applied such that non-analysis target ions are removed and analysis target ions can be trapped.

Figure 52:
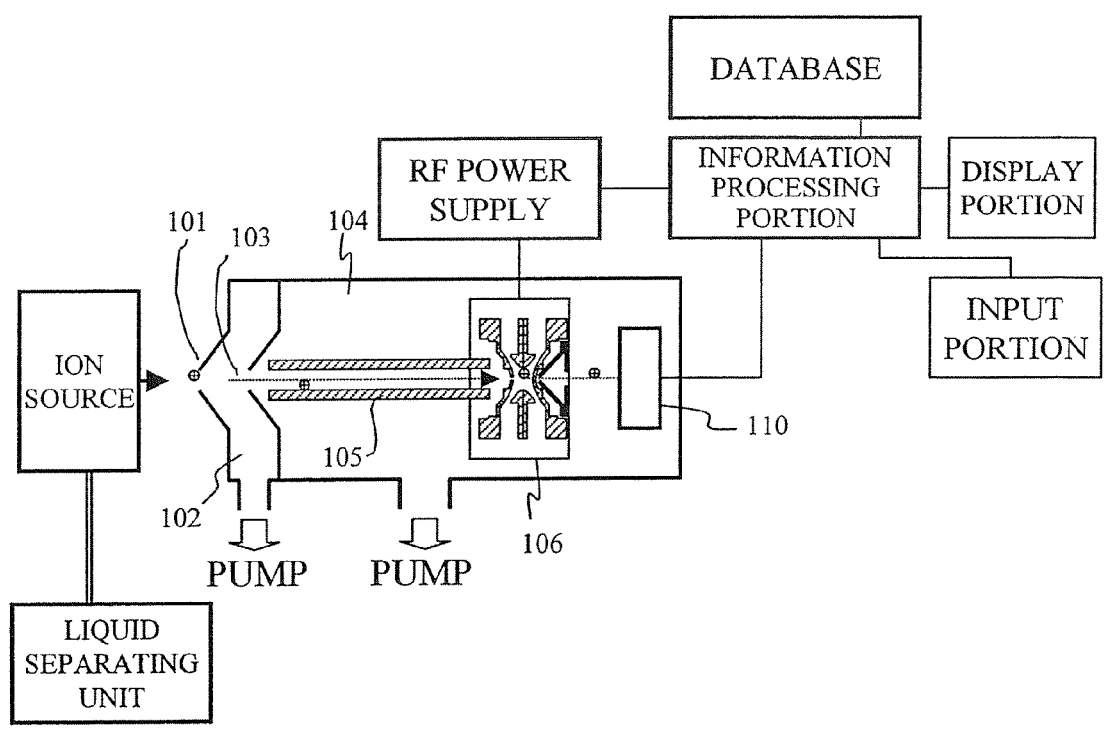
FIG. 52 shows a diagram of a mass spectroscopy system based on yet another embodiment of the invention employing a quadrupole ion trap mass spectrometer.

Alternatively, the mass spectrometer may only comprise the quadrupole ion trap spectrometer as shown in FIG. 52. A sample solution separated in a liquid separation portion such as a liquid chromatograph is introduced into an ion source where it is turned into a gaseous ion. The thus produced gaseous ion is introduced into a differential pumping portion 102 through a pore 101. The gaseous ion further passes through a pore 103 and an ion transport portion 105 disposed in a high vacuum portion 104 and is then introduced into an ion trap 106. An RF voltage is supplied form an RF power supply to the ion trap 106 such that the gaseous ion is trapped at the center of the ion trap 106. To the ion trap 106, an RF voltage is applied such that non-analysis target ions are removed and analysis target ions can be trapped.

The gaseous ion that has been trapped for a certain duration of time is discharged from the ion trap 6 in accordance with the m/z of the ion as the RF voltage applied thereto is continuously changed, and is then detected by a detector 110. The output of the detector 110 is led to the information processing unit where the m/z of the ion can be determined (i.e., subjected to the primary mass spectroscopy) based on the ion detection time. As in the example of FIG. 47, the secondary mass spectroscopy may also be performed. As compared with the time-of-flight mass spectrometer, although the quadrupole ion trap has a narrower range of mass spectroscopy and lower mass resolution and mass accuracy, it allows the apparatus to be reduced in size and also allows highly sensitive analysis to be performed.

In the embodiments shown in FIGS. 50, 51 and 52, by applying an RF voltage in response to an instruction from the information processing unit, non-analysis target ions are eliminated prior to the primary mass spectroscopy, so that the minute component that is desired to be analyzed can be reliably subjected to mass spectroscopy. In particular, when the linear trap shown in FIG. 51 is employed, since the linear trap has a volume that is larger than that of the quadrupole ion trap shown in FIG. 47, for example, by two orders of magnitude, the minute components can be more reliably subjected to mass spectroscopy.

The screen operations illustrated in FIG. 46 are carried out using the display unit and the input unit. On the input screen displayed on the display unit, the information about the analysis target ions (such as the mass and the m/z of the ion) can be entered via the input unit prior to analysis. The first database is created as described above and stored by the storage means. Based on the first database, the RF power supply is controlled in the information processing unit and an RF voltage is applied to the ion trap 106 or the multipole pole in the ion transport portion 105. As a result, the RF voltage, for the purpose of resonance discharge, is applied to those ions among the ions introduced to the ion trap 106 from the ion source that are other than the analysis target ions, and the analysis target ions are trapped by the ion trap 106. If the ions that could possibly disrupt the analysis are known, the information about such ions may be stored in the second database. By so doing, the non-analysis target ions can be removed by an RF electric field for resonance discharge, while trapping the analysis target ions in the ion trap 106. By these operations, in the event that any analysis target ions contained in the ions produced by the ion source can be trapped by the ion trap 106 and then subjected to mass spectroscopy (primary mass spectroscopy). The information about the ions detected by the primary mass spectroscopy is then collated with the first database, and the corresponding ions are preferentially subjected to tandem mass spectroscopy (secondary mass spectroscopy). The priority order for the tandem mass spectroscopy may be descending order of ion intensity, or it may start from the multivalent ions from which it is easier to detect fragment ions. Thereafter, the secondary mass spectroscopy target ions (of a single type) are isolated by the ion trap 6 in accordance with the priority order and are then fragmented (dissociated) by CID, for example. In the embodiments shown in FIGS. 50 and 51, the produced ions (fragment ions) are transported to the right by an electric force and then subjected to analysis in the time-of-flight mass spectrometer 107. In the embodiment shown in FIG. 52, the secondary mass spectroscopy is conducted in the ion trap 106. Such a tandem mass spectroscopy (MS/MS) sequence is carried out on the analysis target ion one after another, thereby obtaining an MS/MS spectrum for each. Further, it is also possible to perform a higher-order tandem mass spectroscopy (MS$^n$ (n=3, 4, . . . )) by similar operations.

Figure 53:
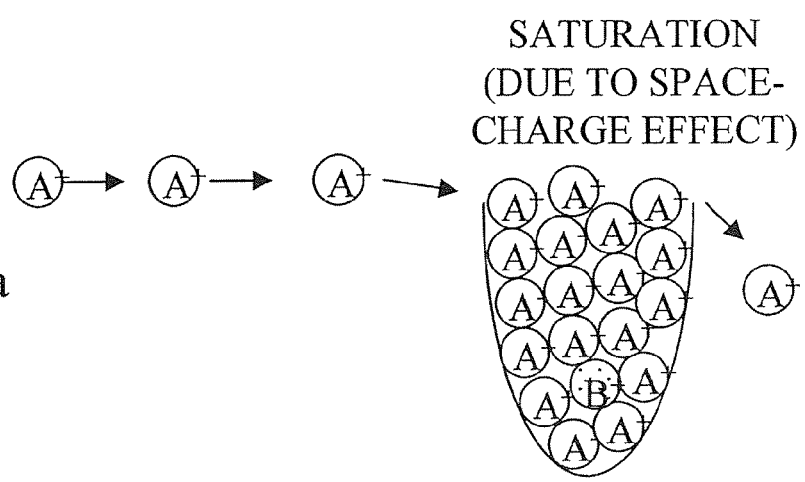
FIG. 53 schematically shows how an ion is trapped by the ion trap.
Figure 53:
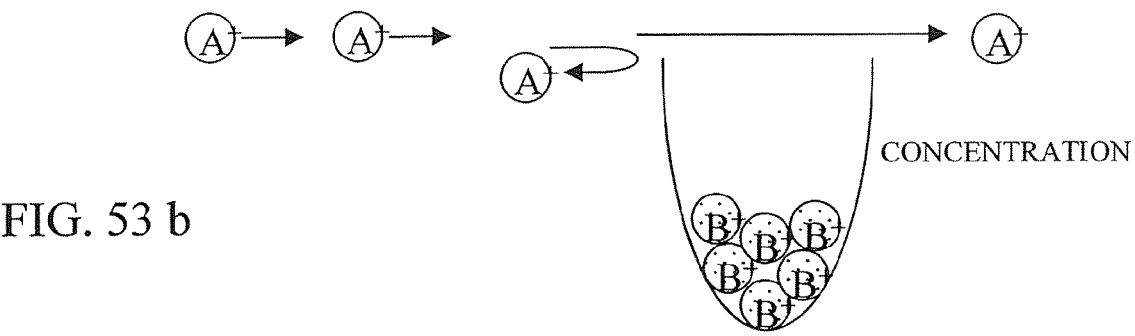

FIG. 53 schematically illustrates the trapping of ions in a ion trap. As shown in FIG. 53(*a*), normally an RF voltage for trapping the injected ions is applied to the ion trap, so that a mixture of the A$^+$ and B$^+$ ions introduced from the left is trapped by the ion trap in accordance with their abundance ratios. For example, when the abundance ratio of A$^+$ ions is far greater than that of B$^+$ ions, there would be far more A$^+$ ions that are trapped. Meanwhile, the total amount of ions that are trapped by the ion trap is limited by the space-charge effect. As a result, the number of B$^+$ ions that are trapped can sometimes be only several, making B$^+$ ions difficult to detect. If there are several kinds of ions with high abundance ratios, such as A$^+$ ions, at the same time, only those ions with high abundance ratios could be dissociated by the ion trap and subjected to CID, and the ions with lower abundance ratios, such as B$^+$ ions, might not be chosen as the target for tandem mass spectroscopy. In the case where another RF voltage for resonance-discharging A$^+$ ions is applied in a superposed manner in addition to the RF voltage for trapping the injected ions in the ion trap, although A$^+$ ions are once introduced into the ion trap, as shown in FIG. 53(*b*), they are heated and then discharged from the ion trap to the outside. As a result, B$^+$ ions are concentrated in the ion trap and so the number of B$^+$ ions that can be detected can be increased. This means that the B$^+$ ion detection sensitivity increases and B$^+$ ions can also be subjected to tandem mass spectroscopy. By applying an RF voltage to the ion transport portion 105 for resonance-discharging A$^+$ ions in a superposed manner in addition to the RF voltage for trapping the injected ions, as shown in FIGS. 50, 51 and 52, the direct introduction of A$^+$ ions to the ion trap can be prevented. As a result, the detection sensitivity for B$^+$ ions can be further improved. In the embodiments of the invention, an improvement of 2 to 3 folds was observed in the detection sensitivity for ions with lower ion abundance ratios due to the application of the RF voltage.

Figure 54:
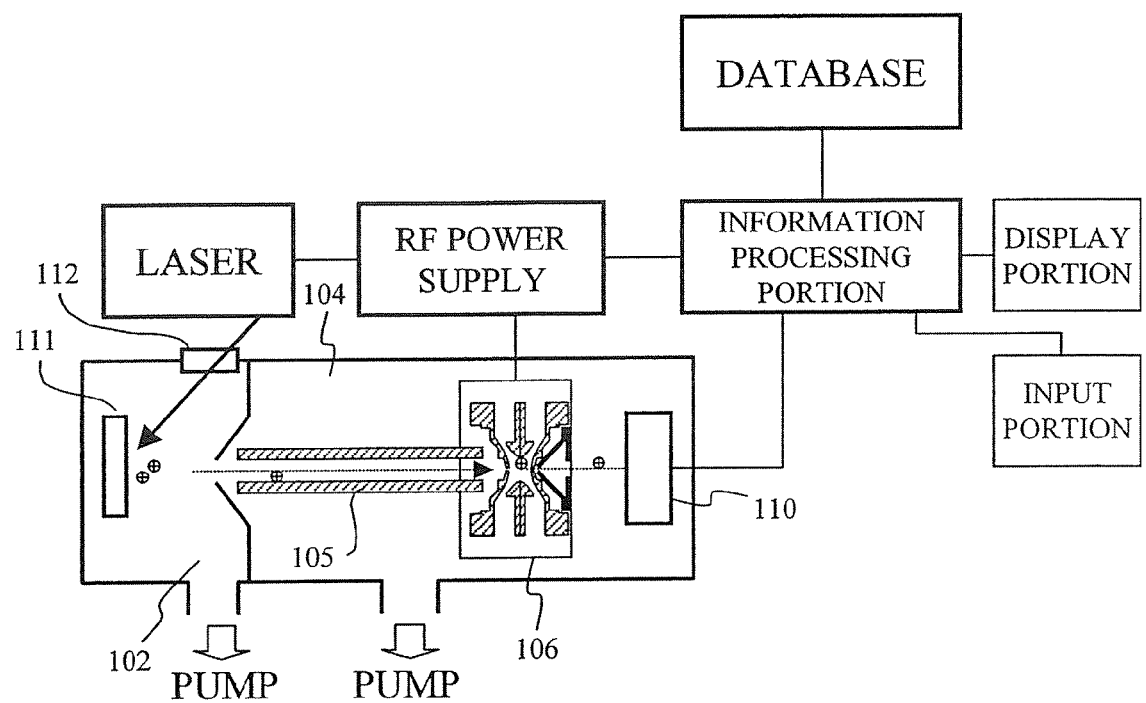
FIG. 54 shows a diagram of a mass spectroscopy system based on another embodiment of the invention employing MALDI in an ion source.
Figure 55:
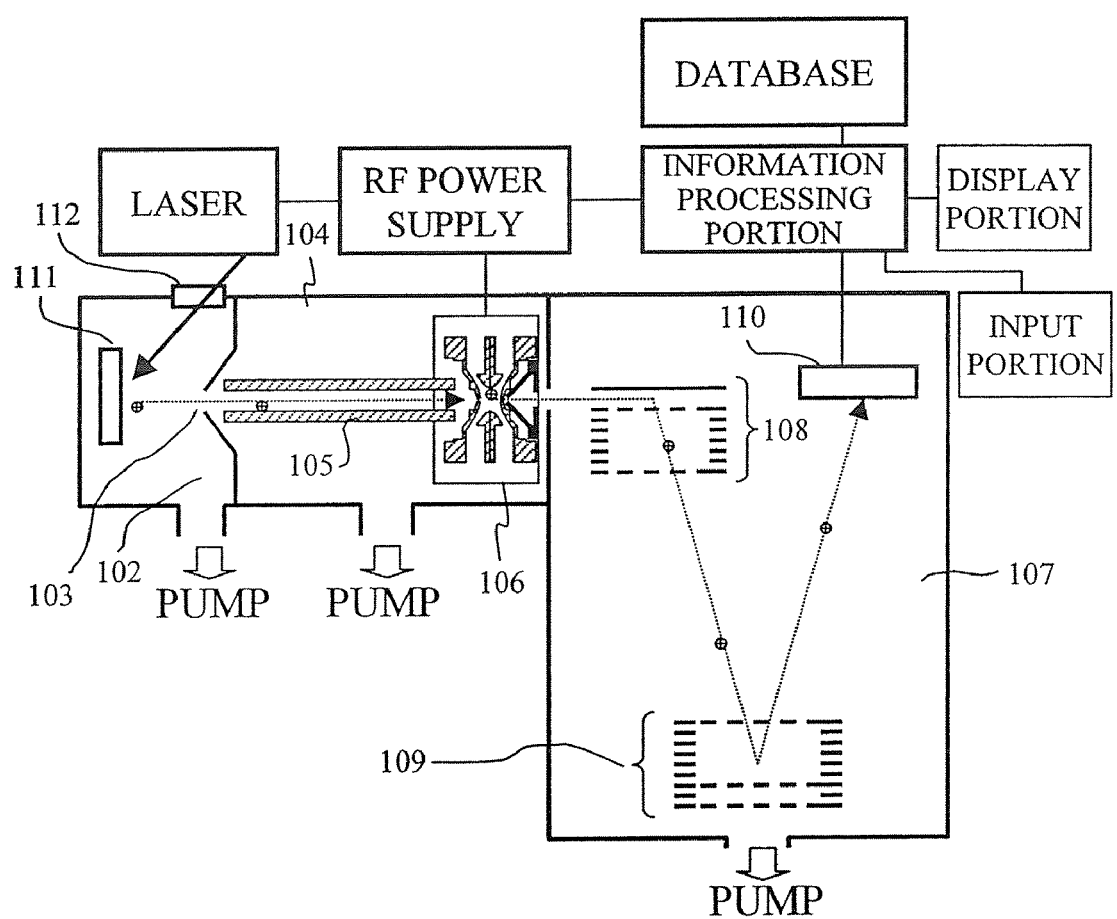
FIG. 55 shows a diagram of a mass spectroscopy system based on another embodiment of the invention employing MALDI in an ion source.
Figure 56:
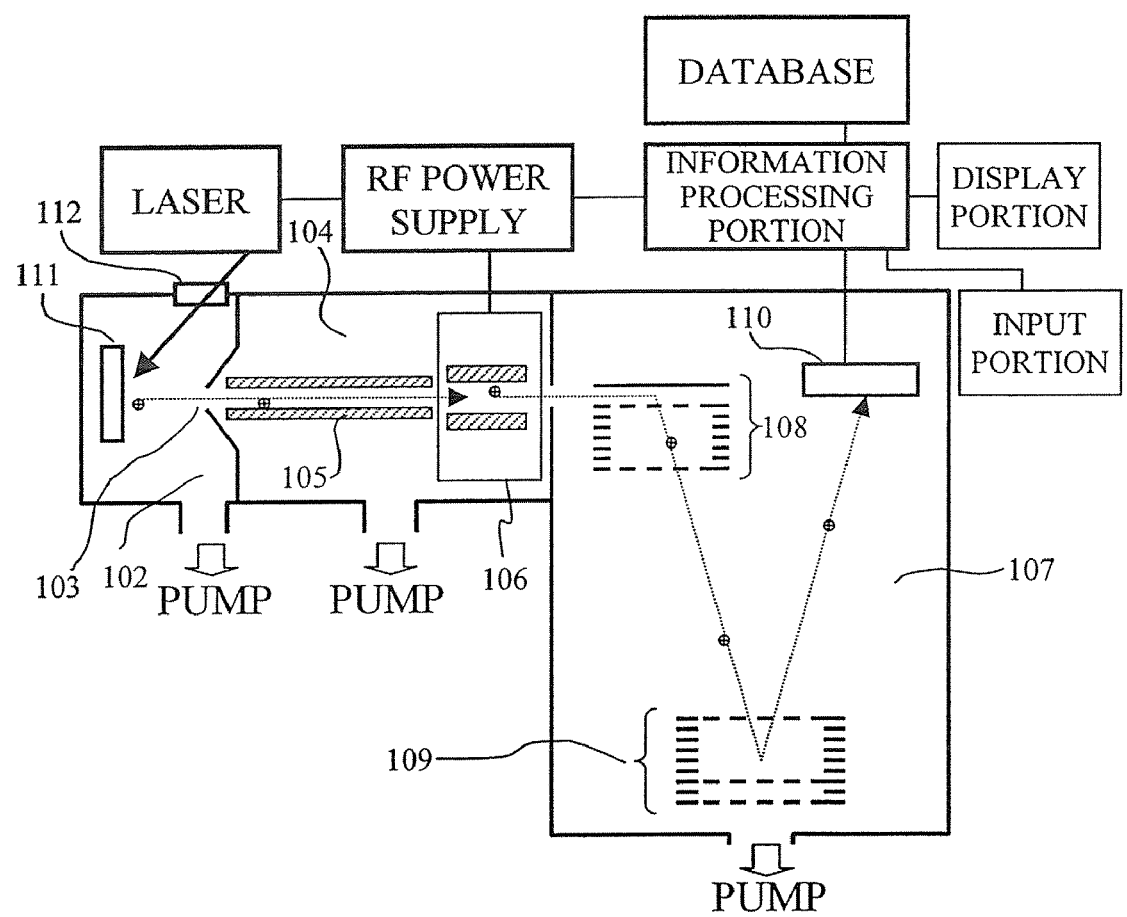
FIG. 56 shows a diagram of a mass spectroscopy system based on yet another embodiment of the invention employing MALDI in an ion source.

FIGS. 54, 55 and 56 show diagrams of apparatuses in which MALDI (matrix-assisted laser desorption ionization) is employed in the ion source according to an embodiment. The example shown in FIG. 54 employs a quadrupole ion trap mass spectrometer, and the example shown in FIG. 55 employs a quadrupole ion trap time-of-flight mass spectrometer. The ion trap 106 may adopt a quadrupole linear trap as shown in FIG. 56, instead of the quadrupole ion trap. A sample is fixed on a plate 111, together with a matrix substance, and dried. The thus prepared plate 111 is placed inside the vacuum apparatus and is irradiated with a pulsed laser. The vacuum apparatus has a window 112 through which a laser beam emitted by a laser that is oscillated under atmospheric pressure can be irradiated into the vacuum apparatus. As the plate 111 is irradiated with the laser beam (with a beam diameter of approximately 0.1 mm), ions are produced within a time interval of the order of microseconds. By moving the location on the plate 111 that is irradiated with the laser, gaseous ions are produced in a consecutive manner. The thus produced ions pass through the ion transport portion 105 consisting of a multipole pole, for example, and are introduced into the ion trap 106. An RF voltage is applied to the ion trap 106 such that the gaseous ions are trapped at the center of the ion trap 106. Although in the present embodiments the plate 111 is disposed within the vacuum apparatus, it may alternatively be disposed under atmospheric pressure. In the embodiments shown in FIGS. 54, 55 and 56 too, non-analysis target ions can be eliminated prior to the primary mass spectroscopy by applying an RF voltage in response to an instruction from the information processing unit, so that a minute component that is desired to be analyzed can be reliably subjected to mass spectroscopy.

Figure 57:
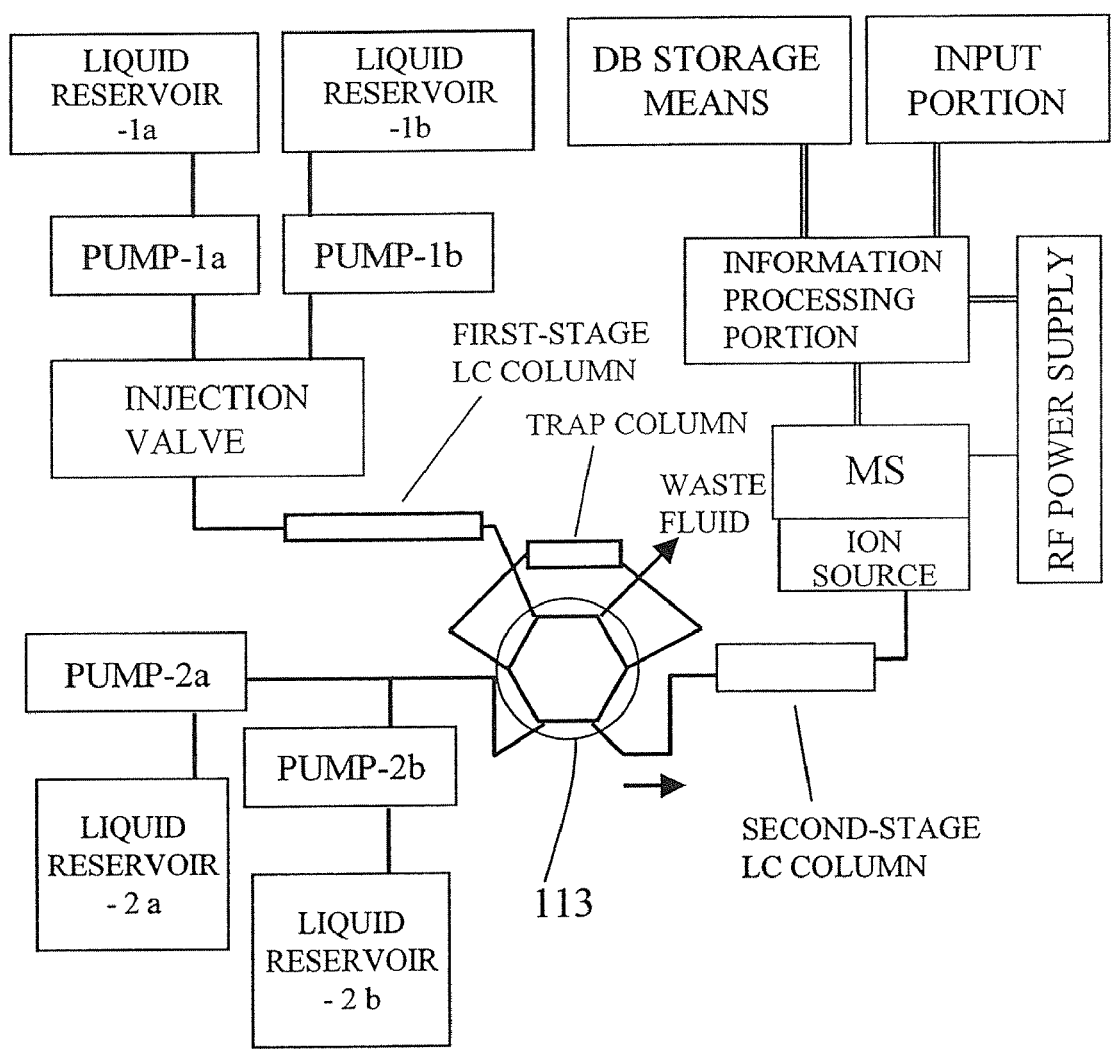
FIG. 57 shows a diagram of a mass spectroscopy system based on yet another embodiment of the invention.

FIG. 57 shows a diagram of an apparatus according to another embodiment of the mass spectroscopy system of the invention. The present embodiment involves a two-dimensional liquid chromatography/mass spectroscopy system. A liquid sample is introduced into a liquid chromatograph column (LC column) in a first dimension via an injection valve. In order to create a gradient in a mobile-phase solution, two kinds of mobile-phase solutions prepared in two liquid reservoirs 101 are introduced into the injection valve while their flow volumes are adjusted by two pumps 101. The liquid sample separated in the LC column is sequentially introduced into a switching valve 113 and adsorbed by a trap column. After adsorption is performed in the top column for a certain duration of time, the pumps 101 are deactivated.

Then, the two kinds of mobile-phase solutions prepared in another two liquid reservoirs 102 are introduced into the trap column with their flow volume being adjusted by two pumps 102. A separated sample adsorbed on the trap column is eluted and introduced into a second liquid chomatography (LC) column where it is further separated. The separated samples are consecutively introduced into the mass spectrometer and subjected to mass spectroscopy therein. After separation, the pumps 102 are deactivated, and the pump 1 is activated. The liquid samples that are separated in the first-dimension LC column are adsorbed by the trap column for a certain duration of time, separated in the second-dimension LC column, and then subjected to mass spectroscopy. Thus, the liquid samples that have been two dimensionally LCseparated are consecutively subjected to mass spectroscopy. If the number of types of samples that are mixed is small, the separation can be sufficiently carried out by the LC/MC analysis alone that utilizes only one-dimensional LC. However, when there are great many kinds of samples, even the two-dimensional LC may not be capable of achieving complete separation, often resulting in a mixture of samples being introduced for MS. As mentioned above, there is a limit to the number of kinds of ions that can be subjected to tandem mass spectroscopy in an identical sample. Thus, it is very effective to preferentially subject the analysis target substances to tandem mass spectroscopy in the case of a minute sample.

Figure 58:
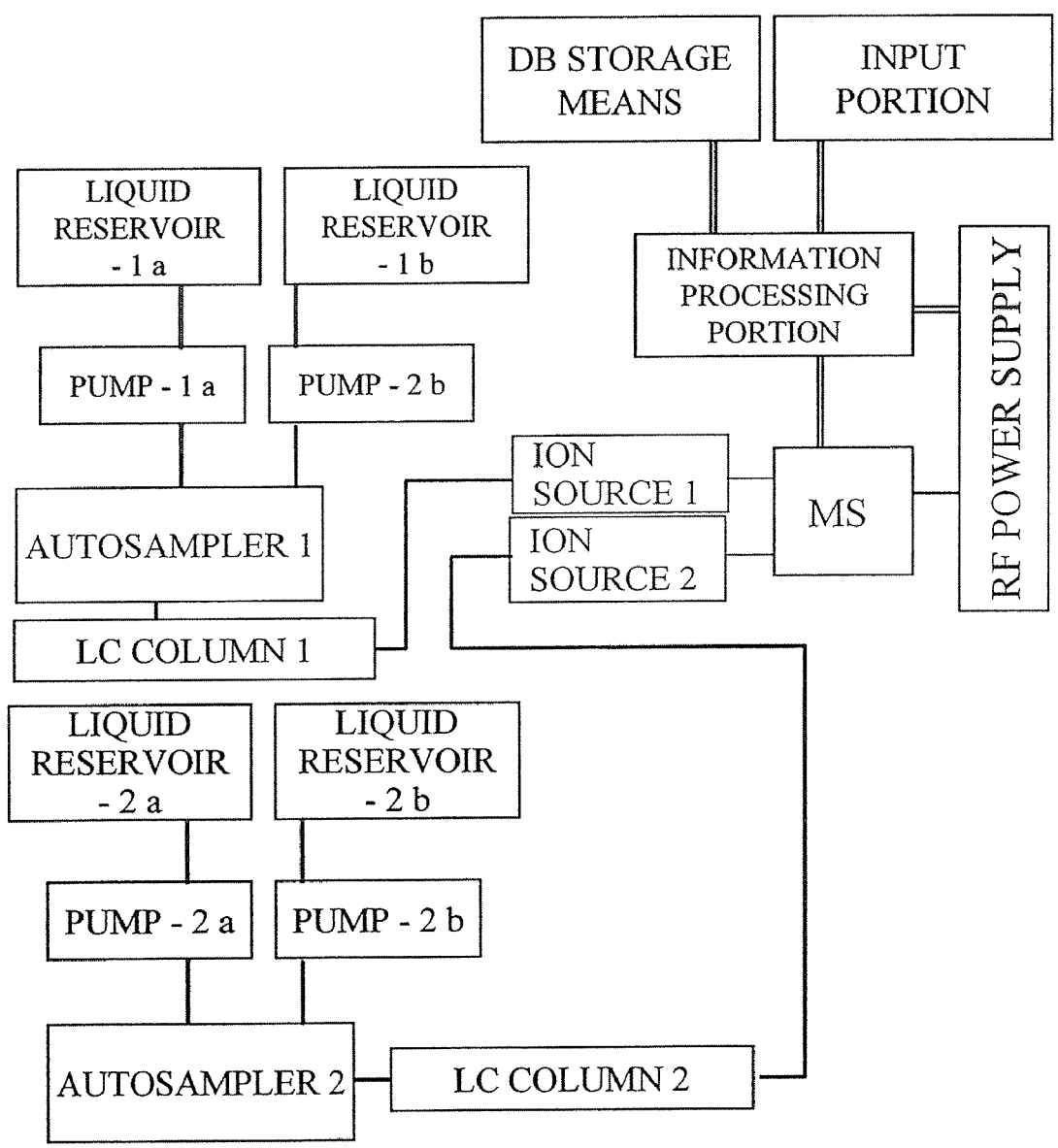
FIG. 58 shows a diagram of a mass spectroscopy system based on yet another embodiment of the invention.

In cases where the analysis target substances are clearly identified and the number of analysis samples is large, a high-throughput analysis can be performed by using the LC columns in parallel. In the embodiment shown in FIG. 58, where the LC/MS analysis is performed, LC and the ion sources are used in parallel. If the LC elation time of the analysis target substance can be predicted, the time when a gaseous ion derived from the analysis target substance is generated can be shifted by shifting the start time of the LC analysis. Namely, after the analysis of the gaseous ion derived from the analysis target substance that is produced from the ion source 101, the gaseous ion derived from the analysis target substance that is produced from the ion source 102 is analyzed. At the coupling portion between the ion source and the mass spectrometer, a plurality of ion sources are temporally switched. The ion sources and the LC columns may be integrated. In another method, a single ion source may be employed, and the separated liquid samples that are introduced into the ion source may be switched by a valve, for example. In this case, however, the distance between the end of LC and the ion source would be too long, and the degree of separation might be reduced upon generation of ions. In this type of parallel LC process, the wait period (approximately 1 hour) in which the gaseous ion derived from the analysis target substance is not analyzed can be effectively utilized, thereby enabling a high-throughput analysis. Although in the present embodiment the number of parallel processes is two, the number may be increased. In order to allow a plurality of types of substances to be analyzed, the correspondence between the movement time of the ion source and the analysis target ions listed in the first database and the start time of the LC analysis, for example, can be usefully specified in advance via the input unit.

Figure 59:
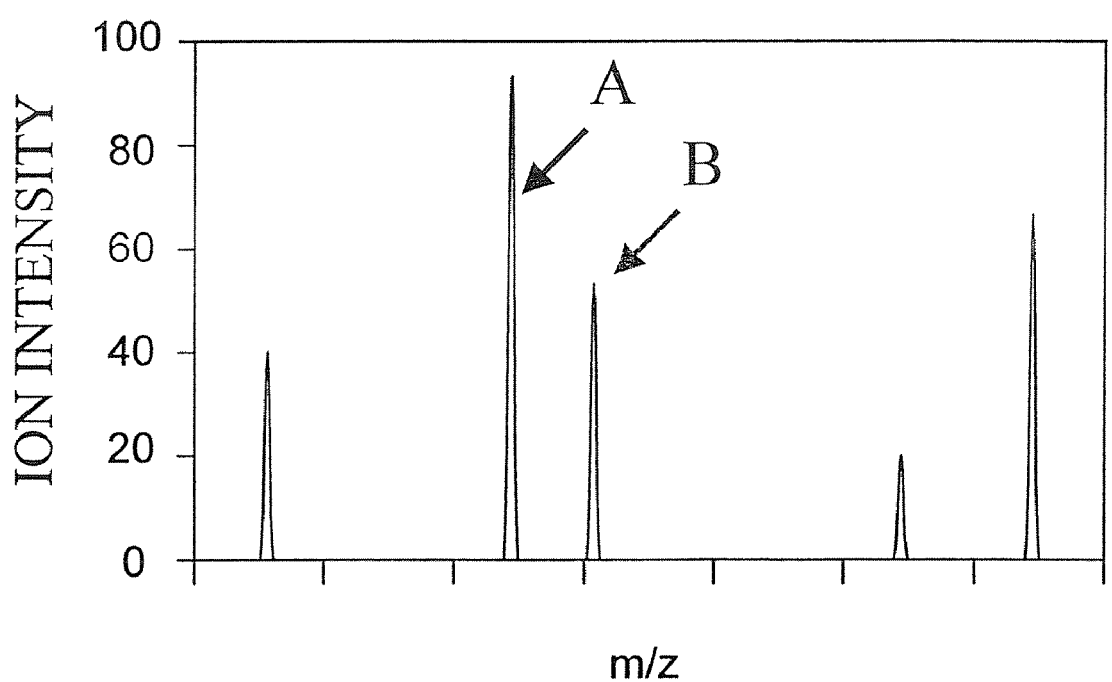
FIG. 59 shows an example of mass spectrum obtained by a mass spectroscopy system based on yet another embodiment of the invention.
Figure 60:
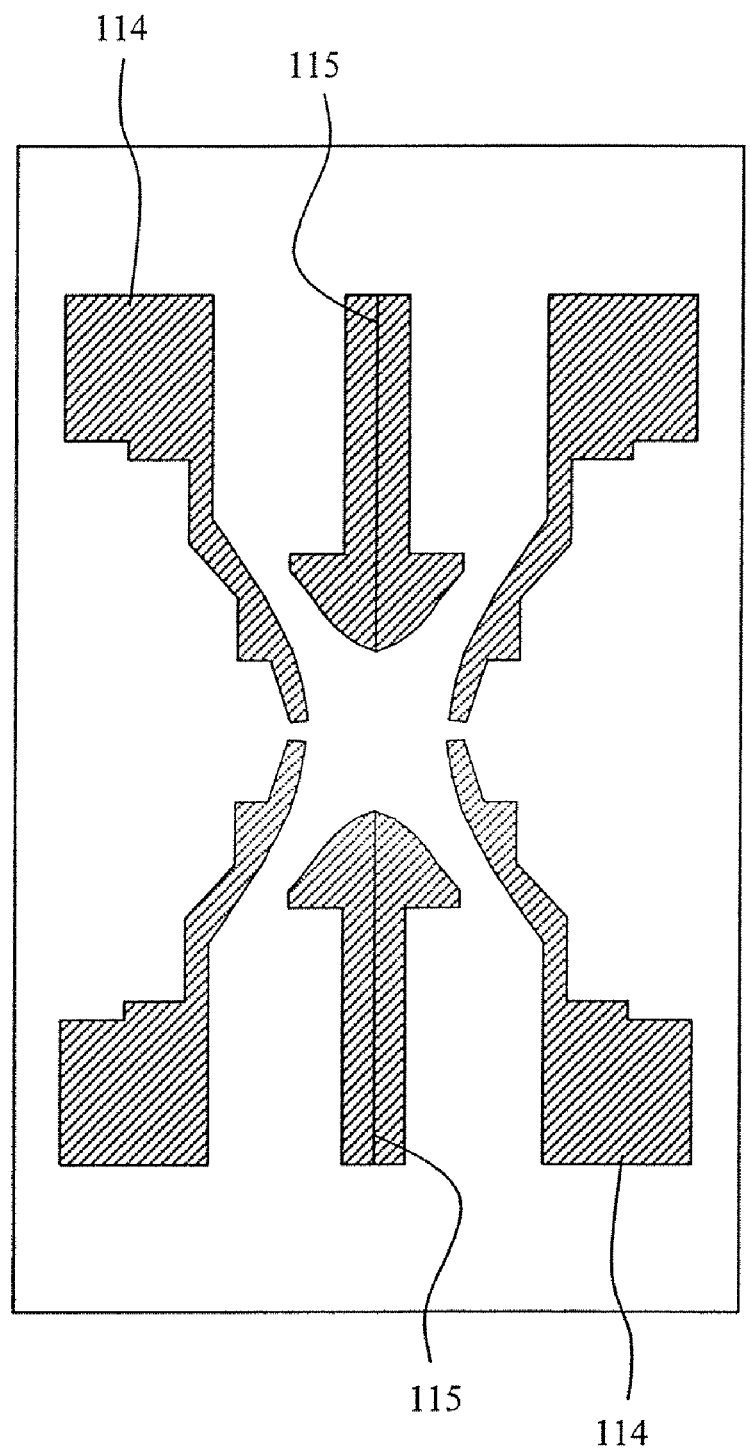
FIG. 60 shows a cross section of a quadrupole ion trap according to the prior art.

In the evaluation of metabolites and diagnosis, the analysis target substance is clearly identified in advance, and the substance must be quantified. In such a case, by adding a certain amount of an internal standard substance that has substantially identical chemical properties to those of the analysis target substance and that differs only in molecular amount to the sample, the quantitative analysis can be accurately performed. In a typical internal standard substance, stable isotopes such as deuterium, $^{13}C$, $^{18}O$, and $^{15}N$ are substituted. In the internal standard substance, the elation time in the separation means such as LC is the same, the chemical properties such as the loss due to adsorption on the wall surface and the ionization efficiency in the ion source are the same, but the mass number is different. In the result of the primary mass spectroscopy (mass spectrum) obtained from such a sample, a pair of peaks are detected, as shown in FIG. 59. A peak indicated by reference A is the peak of the analysis target substance, and a peak referenced by B is the peak of the substance in which isotopes are substituted. As there is the possibility that ions derived from different substances with the same mass are superposed by chance, the two peaks are separately subjected to tandem mass spectroscopy. Then, based on the result of the secondary mass spectroscopy (MS/MS spectrum), the analysis target substance is identified. Quantitative determination may be further conducted based on a ratio of the ion intensities (peak areas). When such a quantitative determination is conducted, the pair of the analysis target ions must be registered in a list in the first database in advance. The figure also shows several peaks in addition to those referenced by arrows. Even if all of such peaks correspond to the peaks registered in the list in the first database, the pair of peaks indicated by the arrows must be preferentially selected as the targets for tandem mass spectroscopy. Further, if the peak of only one of the pair is detected, the ions should be regarded as having not detected and do not need to be selected as the targets for tandem mass spectroscopy even when the ions are registered in the list in the first database. These analysis results are displayed in terms of concentration or relative ratios (%, for example) together with the sample number. In the case of diagnosis, for example, the range of normal or abnormal values is predetermined. Thus, when the analysis result exceeds an expected range, the excess is represented by an indication (by way of color, underlining, asterisk, or font, for example) in the output result displayed on the screen, in a printout, or in an electronic mail, for ease of recognition.

In the following, various examples of the invention are listed:

(1) In a mass spectroscopy system using a tandem mass spectrometer in which a substance to be the target of measurement of the mass spectrometer is ionized, an ion species with a specific mass-to-charge-ratio m/z is selected from a variety of ion species that are produced, the specific ion species is dissociated, wherein the selection, dissociation, and measurement of the ion species as the measurement target are repeated in multiple stages. The selection and dissociation of ion species are repeated n−1 times (where n is an integer$\geq 1$) and are then subjected to mass spectroscopy. Based on the result of an n-stage mass spectroscopy ($MS^n$), which is a measured mass spectrum represented in terms of a peak of a measured intensity against the mass-to-charge-ratio m/z of an ion, it is determined whether or not there is the possibility of correspondence to characteristics data (such as the mass number m of an ion species and/or the retention time τ in a liquid chromatography unit and/or a gas chromatography unit if one or both of these are provided in a stage prior to the mass spectrometer) for an ion species that is designated in advance. Based on this determination, the content of the next $MS^n$ analysis is automatically determined within a specific duration of time.

(2) The characteristics data about the ion species designated in advance is stored in a database the mass spectroscopy system possesses internally.

(3) The database the mass spectroscopy system possesses internally automatically stores the characteristics data about the ion species that has been once measured, or the characteristics data about a variety of peptides of which the breakdown or production by a designated enzyme is predicted for a protein that has been once identified.

(4) The database the mass spectroscopy system possesses internally stores the characteristics data about a variety of peptides of which the breakdown or production by a designated enzyme is predicted for a protein entered or designated in advance by a user.

(5) The database the mass spectroscopy system possesses internally stores the characteristics data about a specific ion species derived from noise or impurity that is entered or designated by the user in advance.

(6) The database the mass spectroscopy system possesses internally stores, even during measurement, the data that has already been measured as needed.

(7) In a method of automatically determining the content of the next $MS^n$ analysis within a certain period of time based on the result of a determination as to the possibility of correspondence to the characteristics data about an ion species that is designated in advance, a mass spectrum that is the result of an n-stage mass spectroscopy ($MS^n$) is represented in terms of a peak (ion peak) of a measured intensity against the mass-to-charge-ratio m/z of an ion. An ion peak with a certain m/z value that is determined to correspond to the characteristics data is selected as the target ion species for the selection and dissociation in the next $MS^n$ analysis if the next $MS^n$ analysis is $MS^n$ ($n \geq 2$), or avoided from becoming the target.

(8) In a method where, when the next $MS^n$ analysis is $MS^n$ ($n \geq 2$), the ion peak with the certain m/z value that has been determined to correspond to the characteristics data is avoided from becoming the target ion species for the selection and dissociation in the next $MS^n$ analysis, the peaks that have been determined to not correspond to the characteristics data are selected as the target ion species for the next $MS^n$ analysis in the order of decreasing intensity.

(9) In a method of automatically determining the content of the next $MS^n$ analysis within a specific period of time, the specific period of time refers to the time between an n-stage mass spectrum measurement ($MS^n$) and the time that does not interrupt the next analysis measurement, a preparation time when transitioning from an n-stage mass spectrum measurement ($MS^n$) to the next analysis, or any of the times of 100 msec, 10 msec, 5 msec, and 1 msec.

(10) In a method of automatically determining the content of the next $MS^n$ analysis within a specific time period, the next $MS^n$ analysis refers to the selection of an ion peak with a certain m/z value from an n-stage mass spectrum ($MS^n$), an n-th stage dissociation, and an n+1th stage mass spectroscopy ($MS^{n+1}$).

(11) In a method of automatically determining the next $MS^n$ analysis content within a specific period of time, the next $MS^n$ analysis content comprises selecting an ion peak, upon obtaining the result of an n-th stage mass spectroscopy ($MS^n$), from the result of an n–1-th mass spectroscopy ($MS^{n-1}$) that has an m/z value that is different from the certain m/z value of the ion peak selected in the n–1-th mass spectrum ($MS^{n-1}$), dissociating the ion peak, and then performing the n-th mass spectroscopy ($MS^n$) again.

(12) In a method in which the ion peak with a different m/z value from the certain m/z value of the ion peak that has been selected in the n–1-th stage mass spectrum ($MS^{n-1}$) is selected, upon obtaining the result of the n-th stage mass spectroscopy ($MS^n$), from the result of the n–1-th mass spectroscopy ($MS^{n-1}$) and then dissociated, and the n-th stage mass spectroscopy ($MS^n$) is performed again, upon obtaining the result of the n-th stage mass spectroscopy ($MS^n$), an ion peak with the same mass number m and a different valence z from the ion peak with the certain m/z value that has been selected in the n–1-th mass spectrum ($MS^{n-1}$) is selected from the result of the n–1-th mass spectroscopy ($MS^{n-1}$) and then dissociated, and the n-th stage mass spectroscopy ($MS^n$) is performed again.

(13) In a method of automatically determining the next $MS^n$ analysis content within a specific period of time, the next $MS^n$ analysis content comprises performing the $1^{st}$-stage mass spectroscopy ($MS^1$) on a next sample, or terminating the measurement, instead of proceeding to tandem mass spectroscopy where a higher-stage dissociation and analysis is performed.

(14) In a method of automatically determining the content of the next $MS^n$ analysis within a specific period of time, operating conditions, such as the voltage in a tandem mass spectroscopy apparatus, are automatically adjusted or changed depending on the content of the next $MS^n$ analysis.

(15) In a method of changing the operating conditions, such as the voltage in the tandem mass spectroscopy apparatus, depending on the content of the next $MS^n$ analysis, a mass spectroscopy system in which, if the next $MS^n$ analysis is $MS^n$ ($n \geq 2$), the operating conditions such as the voltage in the tandem mass spectroscopy apparatus are automatically adjusted or changed depending on the value of the mass-to-charge-ratio m/z of a parent ion that is the target for selection and dissociation.

(16) The characteristics data include the mass number, valence, mass-to-charge-ratio or m/z value, and detection intensity of the ion species, the retention time of liquid chromatography (LC) or gas chromatography (GC), solvents for LC or GC or their mobile-phase ratio, the flow volume or gradient of LC or GC, and, in cases where a two-dimensional LC is used, a sample number of the sample that was divided during the ion exchange in the one-dimensional LC. The characteristics data also include, in cases where a MADLI ion source is employed, the spot position, number or coordinates on a sample plate, and the content of measures to be taken, in accordance with a user specification, for example, for each of the ion species that corresponded to the stored characteristics data (such as whether or not a particular ion species should be excluded from the target ion species for the next $MS^n$ ($n \geq 1$) analysis, whether or not a particular ion species should be selected as the target ion species for the next $MS^n$ ($n \geq 1$) analysis, or whether or not the particular ion species should be removed upon or prior to the injection of an ion sample into the mass spectroscopy system), analysis conditions including the date of measurement, a column number of the LC or GC used, an order n of the tandem mass spectroscopy $MS^n$, and the operating condition of the mass spectrometer, and, in cases involving a protein or peptide sample, information about the inferred structure of an ion species, such as the amino acid sequence.

(17) A mass spectroscopy system comprising a function for automatically correcting or calibrating the retention time of actually measured data concerning liquid chromatography (LC) or gas chromatography (GC) based on a comparison of an actually measured retention time of a designated reference substance and a retention time of a reference substance stored in a database provided in the system.

(18) With regard to the mass number and the mass-to-charge ratio m/z value of an ion species, if the ion species is accompanied by an isotope peak upon deriving of the mass number, the mass number without isotopes is obtained, and, with regard to the mass-to-charge ratio m/z value, if the value fluctuates as time elapses from the start of measurement, at least one reference substance with a known m/z value is contained in the sample, and, in the case of a plurality of reference substances, reference substances with different retention times of LC or GC are selected, and by comparing the m/z value of an actually measured reference substance and the known m/z value, the m/z value that fluctuates with the lapse of time from the start of measurement is automatically corrected or calibrated.

(19) The characteristics data of the ion species that is designated in advance is the characteristics data of a peptide.

(20) The characteristics data of the ion species that is designated in advance is the characteristics data of a peptide derived from a specific protein.

(21) The characteristics data of the ion species that is designated in advance is the characteristics data of a modifying structure such as a specific sugar chain.

(22) The characteristics data of the ion species that is designated in advance is the characteristics data of a specific chemical substance.

(23) In a mass spectroscopy system in which the next MS″ analysis content is automatically determined within a specific time period, wherein the items that are entered by the user include the presence or absence of the need for the determination of a digestive enzyme or isotope peaks, the presence or absence of the need for collation with an internal database or a search thereof, and the ion selection resolution.

(24) The characteristics data of the ion species that is designated in advance is the characteristics data of a protein or peptide with a modifying structure such as phosphorylation.

(25) In a method of determining the presence or absence of the possibility of correspondence to the characteristics data of an ion species designated in advance, wherein the determination is made within a tolerance or a certain range designated by the user, for example.

(26) In a method of automatically determining the content of the next MS″ analysis within a certain time period by determining the presence or absence of the possibility of correspondence to the characteristics data of an ion species that is designated in advance, and, based on the result of the determination, the content of the next MS″ analysis determined by the present system, or, in the case of MS″ ($n \geq 2$), the target ion species for selection or dissociation, is displayed on a display or in a file.

(27) In a method of displaying the next MS″ analysis content, there is provided a user-dialog interface that allows the user to acknowledge the next MS″ analysis content, for example, so that the next MS″ analysis can be performed once such an acknowledgement is obtained.

(28) A mass spectroscopy system comprising a plurality of information processing units that perform a process in a parallel manner.

(29) In a method of performing a parallel processing in a plurality of information processing units, a single database is divided into a plurality of databases that are allocated to a plurality of information processing units, wherein a divided database search process is carried out by each of the information processing units in order to perform a database search in a parallel manner.

(30) In a method of performing a parallel processing in a plurality of information processing units, in the case where there are a plurality of databases, each database is allocated to each of a plurality of information processing units and a database search process is carried out by each of the information processing units, thereby performing a plurality of database searches in a parallel manner.

(31) In a mass spectroscopy system in which, with regard to the result of mass spectrum measurement in the n-th stage mass spectroscopy (MS″), the presence or absence of the possibility of correspondence to the characteristics data of an ion species specified in advance is determined and, based on the result of the determination, the next MS″ analysis content is automatically determined within a specific period of time, in the case where a liquid or gas chromatography unit is provided in a stage before a mass spectrometer, a sample is passed through the liquid or gas chromatography unit so that temporally separated samples due to the difference in the retention time during the passage are subjected to mass spectroscopy in a mass spectroscopy unit in a later stage, wherein a measurement in which all of the samples are passed through the liquid or gas chromatography unit and subjected to mass spectroscopy is performed at least twice on the same sample, and wherein the characteristics data of a parent ion with a high intensity that has been subjected to an $MS^2$ analysis in a previous measurement, the characteristics data being stored in an internal database, is utilized in a second measurement and in any of the subsequence measurements where low-intensity ions that are yet to be measured are preferentially subjected to a $MS^2$ analysis.

(32) In a mass spectroscopy system employing a tandem mass spectroscopy apparatus in which a substance as a measurement target for a mass spectrometer is ionized and, from a variety of resultant ion species, an ion species with a specific mass-to-charge ratio m/z is selected and dissociated, wherein the selection, dissociation, and measurement of the ion species as the measurement target are repeated in multiple stages, wherein the selection and dissociation of an ion species are performed n−1 times and mass spectroscopy is performed thereon to obtain an n-th stage mass spectroscopy (MS″) result that is a measured mass spectrum represented in terms of a peak of measurement intensity versus the mass-to-charge ratio m/z of the ion, wherein, based on the measurement result, an isotope peak is determined, on the basis of the result of which the next MS″ analysis content is automatically determined within a certain period of time.

(33) In a method whereby an ion species is selected and dissociated n−1 times and is then subjected to mass spectroscopy to obtain an n-th stage mass spectrum measurement result (MS″), based on which the presence or absence of the possibility of correspondence to the characteristics data of an ion species that is designated in advance is determined, each of ion peaks with different m/z values in the n-th stage mass spectrum measurement (MS″) result is subjected to an isotope peak determination, and an ion valence is derived from the interval between the ion peak and a peak inferred to be an isotope peak, the mass number m of each ion peak is calculated, and, based on the result of the calculation, the next MS″ analysis content is automatically determined within a certain period of time.

(34) In a method of automatically determining the next MS″ analysis content within a specific period of time based on the result of determination of an isotope peak, of peaks with an ion peak interval of not more than 1.1 Da, one with a larger mass-to-charge ratio m/z is inferred to be an isotope peak, an ion valence is derived from the interval between the peaks, the mass number m of each ion peak is calculated, and, based on the value of the mass number m, the next MS″ analysis content is automatically determined within a certain period of time.

(35) The ion valence and the mass numbers m of the ion peaks calculated on the basis of the isotope peak determination are displayed on a display or in a file.

(36) In a method of automatically determining the next MS″ analysis content within a certain time period based on the result of determination of an isotope peak, it is determined whether or not a particular peak estimated to be an isotope peak is an isotope peak by calculating the intensity distribution of isotope peaks based on the mass number m of each ion peak that is estimated by calculation, and then by determining whether or not the particular peak corresponds to the thus calculated intensity distribution precisely or with an error of less than 50%.

(37) In a method of automatically determining the next MS″ analysis content within a specific time period based on the result of determination of an isotope peak, the intensity distribution of isotope peaks is calculated in advance in accordance with the mass number m of an ion, wherein the result of the calculation, namely a distribution pattern of isotope peaks, is stored in a memory medium such as a memory or a database, and then it is automatically determined, within a specific time period, whether or not a particular peak is an isotope peak based on whether or not the distribution pattern of isotope peaks corresponding to the mass number m of each ion peak that is estimated by calculation corresponds to the distribution pattern of estimated isotope pattern completely or with an error of less than 50%.

(38) In a system for automatically determining the next MS″ analysis content within a specific time period based on the result of determination of an isotope peak, data such as the valence z and the mass number m of each ion peak, or the element compositional distribution inferred from the mass number, is displayed on a display, outputted in a data file, or stored in the internal database.

(39) In a method of automatically determining the next MS″ analysis content within a specific time period based on the result of determination of an isotope peak, a mass spectroscopy system in which, when selecting an ion peak as the target for the next MS″ analysis, an isotope peak is selected or avoided, or a peak containing no isotopes is selected.

(40) In a method of automatically determining the next MS″ analysis content within a specific time period based on the result of determination of an isotope peak, when selecting an ion peak as a selection and dissociation target for the next MS″ analysis, an isotope peak is also selected.

(41) In a method of automatically determining the next MS″ analysis content within a specific time period based on the result of determination of an isotope peak, when selecting an ion peak as a selection and dissociation target for the next MS″ analysis, an ion species with a valence of two or more is preferentially selected.

(42) In a method of automatically determining, within a specific time period, whether or not a particular ion peak is an isotope peak, whereby an intensity distribution of isotope peaks is calculated in accordance with the mass number m of an ion in advance, and the result of the calculation, i.e., a distribution pattern of the isotope peaks, is stored in a memory medium such as a memory or a database, wherein it is determined whether or not the distribution pattern of the isotope peaks for the mass number m of each ion that is estimated by calculation corresponds to the distribution pattern of an estimated isotope peak completely or with an error of less than 50%, a mass spectroscopy system in which, for a plurality of ion species with very close mass-to-charge ratio m/z values and different mass numbers m or valence z, the intensity distribution of an isotope peak is calculated in advance in accordance with the mass number m of each ion species, and the result of the calculation, i.e., the distribution pattern of the isotope peak is stored in a memory medium such as a memory or a database, wherein it is determined whether or not the distribution pattern corresponds to the distribution pattern of peaks in the result of the n-th stage mass spectrum measurement (MS″) completely or with an error of less than 50% in order to automatically determine, within a specific time period, whether or not the peak contains a plurality of ion species.

(43) In a mass spectroscopy system in which, for a plurality of ion species with very close mass-to-charge ratio m/z values and different mass numbers m or valence z, the intensity distribution of an isotope peak is calculated in advance in accordance with the mass number m of each ion species, and the result of the calculation, i.e., the distribution pattern of the isotope peak is stored in a memory medium such as a memory or a database, wherein it is determined whether or not the distribution pattern corresponds to the distribution pattern of peaks in the result of the n-th stage mass spectrum measurement (MS″) completely or with an error of less than 50% in order to automatically determine, within a specific time period, whether or not the peak contains a plurality of ion species, a peak that is determined to contain a plurality of ion species is avoided or selected as the target for the next MS″ analysis.

(44) In a system in which a peak that is determined to contain a plurality of ion species is selected as the target for the next MS″ analysis, the possibility of the presence of a plurality of ions is displayed, and the information that is obtained upon determination of the presence of a plurality of ion species, such as the mass number m and valence z of the multiple ion species, is used in the analysis of the data obtained as a result of the next MS″ analysis.

(45) The characteristics data of an ion species that is designated in advance is the characteristics data of an ion derived from a sample that is labeled by an isotope in the case where, in a pre-processing stage prior to mass spectroscopy, there are samples that are labeled by an isotope and samples that are not labeled by an isotope.

(46) In a method of determining the presence or absence of the possibility of correspondence between the characteristics data of an ion species that is designated in advance and the result of an n-th stage mass spectrum measurement (MS″) that is obtained by performing the selection and dissociation of ion species n−1 times and then subjecting the ion species to mass spectroscopy, it is determined whether or not the mass-to-charge ratio m/z value of each ion peak in the result of the n-th stage mass spectrum measurement (MS″) corresponds to the m/z value calculated from the mass number m of the ion species designated in advance and from a valence within an assumed range ($1 \leq z \leq Nz$).

(47) In a method of automatically determining the next MS″ analysis content within a certain period of time, the MS″ spectrum data is analyzed and it is then determined whether or not each mass peak obtained during the certain time period is noise, wherein a peak that is determined to be noise is automatically eliminated.

(48) In a method of automatically determining the next MS″ analysis content within a certain time period, of the ion peaks in the result of the n-th stage mass spectroscopy (MS″), an ion peak of which the intensity varies by more than 50% at each measurement time is avoided or selected as the target ion species for the selection or dissociation in the next MS″ analysis.

(49) In a mass spectroscopy system employing a tandem mass spectroscopy apparatus in which the selection, dissociation, and measurement of an ion species as a measurement object are repeated in multiple stages, the mass spectrometer comprises an ion trap mass spectrometer.

(50) In a mass spectroscopy system employing a tandem mass spectroscopy apparatus in which the selection, dissociation, and measurement of an ion species as a measurement object are repeated in multiple stages, the mass spectrometer comprises an ion trap time-of-flight mass spectrometer.

(51) In a mass spectroscopy system employing a tandem mass spectroscopy apparatus in which the selection, dissociation, and measurement of an ion species as a measurement object are repeated in multiple stages, the mass spectrometer comprises a linear trap time-of-flight mass spectrometer.

(52) In an ion trap, or in the linear trap according to claim 33, when the next MS″ analysis content is MS″ ($n \geq 2$), an RF voltage (frequency or voltage) applied to the ion trap or linear trap during the trap isolation of a target ion species is automatically adjusted or changed in accordance with the mass-to-charge ratio m/z or the selection and dissociation target ion species.

(53) In an ion trap or the linear trap according to claim 33, when the next MS" analysis content is MS" (n≧2), if the dissociation target ion species is to be dissociated by the collision induced dissociation (CID) described in claim 37, an auxiliary AC (frequency or voltage) for collision induced dissociation that is applied in a superposed manner in addition to the RF voltage applied to the ion trap or linear trap during the trap isolation of the target ion species is automatically adjusted or changed in accordance with the mass-to-charge ratio m/z of the dissociated target ion species.

(54) In a mass spectroscopy system employing a tandem mass spectroscopy apparatus in which the selection, dissociation, and measurement of an ion species as a measurement object are repeated in multiple stages, the mass spectrometer comprises a Fourier-transform ion cyclotron resonance (FTICR) mass spectrometer.

(55) A parallel computer is employed for the calculation process in a mass spectroscopy system for automatically determining the next MS" analysis content within a specific period of time.

(56) A cache memory or a hard disc is employed for the storage of necessary data for the calculation process in a mass spectroscopy system for automatically determining the next MS" analysis content within a specific period of time.

(57) In a method of employing a memory or a hard disc for the storage of necessary data, such as the stored data in an internal database, for the calculation process in a mass spectroscopy system for automatically determining the next MS" analysis content within a specific period of time, the necessary data in the hard disc is written in the memory at certain time intervals determined by a user, for example, wherein the memory is accessible at all times during mass spectroscopy measurement so that the data on the memory can be utilized and then stored.

(58) In a method of employing a memory or a hard disc for the storage of necessary data, such as the stored data in an internal database, for the calculation process in a mass spectroscopy system for automatically determining the next MS" analysis content within a specific period of time, the necessary data in the hard disc is written in the memory at the start of mass spectroscopy measurement, wherein the memory is accessible at all times during mass spectroscopy measurement so that the data on the memory can be utilized for analysis and then stored, wherein the necessary data on the memory is written on the hard disc at the end of mass spectroscopy measurement.

(59) In a mass spectroscopy system employing a tandem mass spectroscopy apparatus in which the selection, dissociation, and measurement of an ion species as a measurement object are repeated in multiple stages, collision induced dissociation (CID) or electron capture detection (ECD) as a method of dissociating an ion species.

(60) In a mass spectroscopy system employing a tandem mass spectroscopy apparatus in which the selection, dissociation, and measurement of an ion species as a measurement object are repeated in multiple stages, of the ion peaks in the result of the n-th stage mass spectroscopy (MS"), an ion peak with an intensity ratio of less than 70% relative to a peak with a maximum intensity is selected or avoided as the target ion species for selection and dissociation in the next MS" analysis.

(61) In a mass spectroscopy system employing a tandem mass spectroscopy apparatus in which the selection, dissociation, and measurement of an ion species as a measurement object are repeated in multiple stages, of the ion peaks in the result of the n-th stage mass spectroscopy (MS"), an ion species that is repeatedly detected for more than a certain period specified by a user, for example, is selected as the target ion species for the selection and dissociation in the next MS" analysis, or is determined to be a noise peak due to impurity and avoided from being selected as the target ion species for the selection and dissociation in the next MS" analysis.

(62) In a mass spectroscopy system employing a tandem mass spectroscopy apparatus in which the selection, dissociation, and measurement of an ion species as a measurement object are repeated in multiple stages, of the ion peaks in the result of the n-th stage mass spectroscopy (MS"), an ion species that is repeatedly detected within a certain period specified by a user, for example, is selected as the target ion species for the selection and dissociation in the next MS" analysis, or is determined to be a noise peak due to impurity and avoided from being selected as the target ion species for the selection and dissociation in the next MS" analysis.

(63) An ion species that is repeatedly detected within a certain time period specified by a user, for example, is subjected to the MS analysis, which is the next MS" analysis, as the target ion species for selection and dissociation an indefinite number of times as long as the analysis is performed within the certain time period specified by the user, for example, even if the ion species corresponds to data stored in an internal database in terms of retention time and other data within a certain tolerance, wherein the MS"$^{+1}$ analysis data obtained within the certain time period in which the same ion species has been used as the target ion species for selection and dissociation is accumulated during or after measurement.

(64) The information about the ion species that has been subjected to the MS" (n≧2) analysis and the measurement information and conditions are automatically stored in an internal database of a mass spectroscopy system as a data set with a registration number allocated thereto.

(65) The information about the ion species that has been subjected to the MS" (n≧2) analysis and the measurement information and conditions include the mass number m of the ion, valence z, ion intensity, the retention time in liquid or gas chromatography, and, in the case where there is provided a means for storing ions, the accumulation time of the ion species.

(66) In a method of storing the information about the ion species that has been subjected to the MS" (n≧2) analysis and the measurement information and conditions in an internal database of a mass spectroscopy system with a registration number allocated thereto, by specifying the registration number or a condition of data in a data set, actual-measurement mass spectrum data corresponding to a data set that contains data that satisfies the registration number or the data condition is referenced, displayed, or outputted in a file.

(67) In a method of storing the information about the ion species that has been subjected to the MS" (n≧2) analysis and the measurement information and conditions in an internal database of a mass spectroscopy system with a registration number allocated thereto, the measured mass spectrum data is automatically evaluated or analyzed, and an evaluation indicator obtained as a result is automatically stored in the database.

(68) In a method of automatically evaluating or analyzing the measured mass spectrum data and automatically storing the result, i.e., an evaluation indicator, in a database, the reliability and quality of the measured spectrum data are evaluated.

(69) The evaluation indicator of the measured mass spectrum data indicates the temporal displacement between the time of measurement of a measurement object and the time at which the detection intensity of an ion eluted from the measurement object during liquid or gas chromatography exhibits a peak, or the S/N ratio.

(70) In a method of automatically evaluating or analyzing the measured mass spectrum data and automatically storing the result, i.e., an evaluation indicator, in a database, in the case where the measurement object is a peptide, the number of amino acids that have been read as a result of the analysis of the $MS^2$ spectrum data, the reasons for the determination, and the result of decoding of the amino acids are stored in the database.

(71) In a method of storing the information about the ion species that has been subjected to the $MS^n$ ($n \geq 2$) analysis and the measurement information and conditions in an internal database of a mass spectroscopy system with a registration number allocated thereto, if there are a plurality of data sets (ion species, measurement information and measurement conditions) registered in the database, in which the data obtained in the $MS^1$ analysis stored, that are determined to be identical within a certain tolerance, the redundant data sets are automatically deleted from the database or added together.

(72) The tolerance within which particular data sets are evaluated to be identical, and the information such as valence, mass number and retention time are specified by the user.

(73) In a method of storing the information about the ion species that has been subjected to the $MS^n$ ($n \geq 2$) analysis and the measurement information and conditions in an internal database of a mass spectroscopy system with a registration number allocated thereto, a system in which, if there are a plurality of data sets that contain ion species information that is determined to belong to an identical ion, the data sets that contain redundant ion species information are automatically deleted from the database.

(74) In a method whereby, if there are a plurality of data sets that contain ion species information that is determined to belong to an identical ion, the data sets that contain redundant ion species information are automatically deleted from an internal database of a mass spectroscopy system, the mass spectrum data corresponding to the data sets that contain redundant ion species information is automatically deleted or added.

(75) In a method of determining identical ions based on the information about ion species stored in a database, identical ions refer to those ions of which the mass numbers, valence, and the retention time in liquid or gas chromatography correspond within a certain tolerance.

(76) When performing the next $MS^n$ analysis ($n \geq 2$) in which an ion species with the same mass number and a different valence from the target ion species (parent ion) for selection and dissociation in the $MS^n$ analysis that has already been measured is used as the target ion species for selection and dissociation, the $MS^n$ ($n \geq 2$) spectrum data obtained by using the ion species with the same mass number and a different valence as the selection and dissociation target ion species is fused with or added to the $MS^n$ spectrum data that has already been measured.

(77) In a method of storing the information about the ion species that has been subjected to the $MS^n$ ($n \geq 2$) analysis and the measurement information in the internal database of a mass spectroscopy system with a registration number allocated thereto, in the case where an $MS^n$ ($n \geq 3$) analysis has been conducted, the mass spectrum data obtained by conducting an $MS^2$ analysis of an ion species that contains the precursor ion in the structure thereof that has been used as the object of analysis in the $MS_n$ ($n \geq 3$) analysis is added with the mass spectrum data obtained by conducting the $MS^n$ ($n \geq 3$) analysis, and the thus combined data is stored in the database with a registration number allocated thereto.

(78) In a method of storing the information about the ion species that has been subjected to the $MS^n$ ($n \geq 2$) analysis and the measurement information in the internal database of a mass spectroscopy system with a registration number allocated thereto, in the case where there is mass spectrum data obtained by conducting an $MS^2$ analysis on the same substance using different dissociation methods, the multiple items of mass spectrum data are added and then stored in the database with a registration number allocated thereto.

(79) The different dissociation methods include collision induced dissociation (CID) and electron capture dissociation (ECD).

(80) In a method of adding a plurality of items of mass spectrum data, the ratio of each item of mass spectrum data can be designated by the user.

(81) If it is estimated that, as a result of an analysis of the $MS^n$ spectrum data obtained by using a protein or peptide as the analysis object, a modifying structure such as phosphorylation is added, information about the type of the estimated modifying structure and the location where the modifying structure is added (to which amino acid of the amino acid sequence the structure is added) is also stored in the internal database of the mass spectroscopy system.

(82) The internal database of a mass spectroscopy system stores a peptide sequence or the mass number of the peptide sequence that is produced upon enzymatic digestion of all or some of the proteins stored in databases, such as those that are made public, of the amino acid sequences of general proteins, using a variety of enzymes, wherein it is determined whether or not a particular ion peak in the mass spectrum data of $MS^1$ has any possibility of corresponding to the data stored in the internal database, and the next $MS^n$ analysis content is automatically determined within a specific time period based on the result of the determination.

(83) The presence or absence of the possibility of a particular ion peak in the $MS^1$ mass spectrum data corresponding to any data stored in the database about the enzymatically digested peptide sequence or the mass number thereof, wherein an ion species that corresponds or does not correspond within a certain tolerance is selected as the selection and dissociation target ion species (parent ion) for the $MS^2$ analysis, and the content of the next $MS^n$ analysis is automatically determined within a certain time period.

(84) In a method of referring to, displaying, or outputting in a file actually measured mass spectrum data for a data set containing data in the internal database of a mass spectroscopy system that satisfies a specified registration number or data condition, isotope peaks are removed from the actually measured mass spectrum data, and ion peaks with various valence values are converted such that they are monovalent.

(85) In a method of referring to, displaying, or outputting in a file actually measured mass spectrum data for a data set containing data in the internal database of a mass spectroscopy system that satisfies a specified registration number or data condition, the ion intensity of a peak that is determined to be an isotope peak is added to the intensity of a monoisotopic peak.

(86) In a mass spectroscopy system employing a tandem mass spectroscopy apparatus in which a measurement object substance for a mass spectrometer is ionized, an ion species with a specific mass-to-charge ratio m/z is selected and dissociated from a variety of ion species that are produced, and the selection, dissociation, and measurement of the ion species as a measurement object are repeated in multiple stages, the selection and dissociation of an ion species is performed n−1 times ($n \geq 2$), and the result of an n-th stage mass spectroscopy ($MS^n$) in which the selected and dissociated ion species is subjected to mass spectroscopy, namely mass spectrum data represented in terms of a peak of measurement intensity against the mass-to-charge ratio m/z of the ion, is analyzed within the real time of measurement, wherein the next $MS^n$ analysis content is automatically determined within a specific time period based on the result of the analysis.

(87) The substance as the measurement object for the mass spectrometer is a protein, peptide, or a peptide with a modifying structure.

(88) The substance as the measurement object of the mass spectrometer is a modifying structure such as a sugar chain, or a compound with a modifying structure.

(89) The substance as the measurement object of the mass spectrometer is a substance consisting of a limited number of types of basic structural units that are linked.

(90) In the analysis performed on the result of an n-th stage mass spectroscopy ($MS^n$), namely the mass spectrum data represented in terms of a peak of measurement intensity against the mass-to-charge ratio m/z of the ion, the structural unit making up the parent ion, such as an amino acid, amino acid with a modifying structure, or a sugar chain, or a structure consisting of several linked structural units, is estimated from a mass peak interval, mass-to-charge ratio m/z, and an intensity distribution in the mass spectrum data within a specific time period.

(91) When estimating the structural unit of the parent ion within a specific time period, when the substance as the measurement object for the mass spectrometer is a peptide or a peptide with a modifying structure, an amino acid or a structure consisting of several amino acids is estimated from the mass peak interval of the mass spectrum data.

(92) When estimating a relevant amino acid from the mass peak interval in the mass spectrum data, a dissociated amino acid is estimated from both the N and C terminals of a peptide consisting of amino acids.

(93) When estimating a relevant amino acid from the mass peak interval in the mass spectrum data, the number of amino acids that are estimated with an accuracy or a score of more than a certain value is derived.

(94) If the number of the amino acids that are estimated with an accuracy or score exceeding a certain value as a result of the analysis of the n-th stage mass spectroscopy ($MS^n$) mass spectrum data ($n \geq 2$) exceeds a certain number designated by the user, for example, the next $MS^n$ analysis measurement is conducted or terminated, and if the number is less than the certain designated number, the $MS^{n+1}$ analysis in which one of the ion species that have been detected in the $MS^n$ data ($n \geq 2$) is selected and dissociated and then subjected to mass spectroscopy is automatically conducted, or, if an ion species with a substantially identical mass number to that of the parent ion in the $MS^n$ analysis and with a different valence has been detected in the $MS^{n-1}$ data, the ion species is selected and dissociated and the $MS^n$ analysis is automatically conducted again.

(95) When conducting the $MS^{n+1}$ analysis in which one of the ion species detected in the $MS^n$ data ($n \geq 2$) is selected, dissociated and subjected to mass spectroscopy in the event that the number of the amino acids that have been estimated with an accuracy or score that exceeds a certain value is less than the certain specified number, a peak with the largest m/z value is automatically selected as a parent ion from those peaks containing amino acids whose accuracy or score does not satisfy the certain value.

(96) If the mass number of a single amino acid estimated from the mass peak interval in the mass spectrum data is substantially identical to the sum of the mass numbers of two or more, other kinds of amino acids when they are linked, the $MS^{1+1}$ analysis is automatically conducted or the $MS^n$ analysis is automatically conducted again using a peak that contains that single amino acid.

(97) If, as a result of the analysis of the mass peak interval of the mass spectrum data, there is the possibility that an estimated amino acid has a modifying structure such as phosphorylation, the $MS^{n+1}$ analysis is automatically conducted or the $MS^n$ analysis is automatically conducted again using a peak that contains that amino acid.

(98) In the analysis that is conducted on result of the n-th stage mass spectroscopy ($MS^n$), namely the mass spectrum data represented in terms of a peak of measurement intensity against the mass-to-charge ratio of an ion, one or more mass peaks that are estimated to be derived from a single structural unit, such as a dehydration peak derived from a peak in which a structural unit such as an amino acid is detached, or a de-$NH^3$ peak, are processed as a group of peaks of the same kind, and then the number of the groups of peaks of the same kind is calculated.

(99) If the number of the groups of peaks of the same kind exceeds a certain number designated by the user, for example, the next ion measurement is performed or the measurement is terminated, and if the number is less than the certain number, the $MS^{n+1}$ is conducted or the $MS^n$ analysis is conducted again.

(100) When conducting the $MS^{n+1}$ or repeating the $MS^n$ analysis in the event that the number of the groups of peaks of the same kind is less than the certain number specified by the user, for example, a parent ion is automatically selected from groups of peaks with large m/z values where the interval between one peak group and another is maximum.

(101) In the analysis of the result of the n-th stage mass spectroscopy ($MS^n$), namely the mass spectrum measurement result represented in terms of a peak of measurement intensity against the mass-to-charge ratio m/z of an ion, within the real time of measurement, if the substance as a measurement object is a sugar chain, a relevant monosaccharide or the structure of several monosaccharides linked together is estimated from the mass peak interval in the mass spectrum data.

(102) When estimating the relevant monosaccharide or the structure of several monosaccharides linked together from the mass peak interval in the mass spectrum data, the number of monosaccharides or structures consisting of several monosaccharides linked together that have been estimated with an accuracy or score exceeding a certain value is derived.

(103) If the number of the monosaccharides that have been estimated with an accuracy or score of more than a certain value is not less than a certain number designated by the user, for example, the next $MS^1$ analysis measurement is conducted or terminated, and if the number is less than the certain designated number, the $MS^{n+1}$ analysis in which one of the ion species detected in the $MS^n$ data ($n \geq 2$) is selected, dissociated and subjected to mass spectroscopy is conducted, or if an ion species with a substantially identical mass number and a different valence from the mass number of the parent ion in the $MS^n$ analysis, that ion species is selected and dissociated as the parent ion and the $MS^n$ analysis is automatically conducted again.

(104) When conducting the $MS^{n+1}$ analysis or repeating the $MS^n$ analysis in the event that the number of the saccharides that have been estimated with an accuracy or score exceeding a certain value is less than a certain number designated by the user, for example, a peak with the largest m/z value is automatically selected as a parent ion from the peaks containing monosaccharides whose accuracy or score does not satisfy the certain value.

(105) In the analysis of the result of the n-th stage mass spectroscopy ($MS^n$), namely the mass spectrum measurement result represented in terms of a peak of measurement intensity against the mass-to-charge ratio m/z of an ion, within the real time of measurement, an isotope peak is determined within a specific time period and eliminated from the $MS^n$ ($n \geq 2$) spectrum data on which the analysis is performed.
(106) In the analysis of the result of the n-th stage mass spectroscopy ($MS^n$), namely the mass spectrum measurement result represented in terms of a peak of measurement intensity against the mass-to-charge ratio m/z of an ion, within the real time of measurement, an isotope peak and the valence of each ion are determined within a specific time period, wherein the analysis is conducted on the spectrum data or a peak list from which the isotope peak is eliminated and in which the ions are converted into monovalent ions.
(107) In the analysis of the result of the n-th stage mass spectroscopy ($MS^n$), namely the mass spectrum measurement result represented in terms of a peak of measurement intensity against the mass-to-charge ratio m/z of an ion, within the real time of measurement, an isotope peak and the valence of ions are determined.
(108) The next $MS^n$ analysis refers to the $MS^{n+1}$ ($n \geq 2$) analysis in which one of the ion species detected in the $MS^n$ data ($n \geq 2$) is selected, dissociated and subjected to mass spectroscopy.
(109) In the case where, as the next $MS^n$ analysis content, an ion species with substantially identical mass number and a different valence from the parent ion in the $MS^n$ analysis has been detected, the $MS^n$ analysis ($n \geq 2$) is conducted using the ion species as the parent ion.
(110) An intensity distribution in mass spectrum data is analyzed on the basis of the ease with which individual amino acids can be dissociated from one another, or a database of the intensity distribution.
(111) When conducting the $MS^{n+1}$ analysis or repeating the $MS^n$ analysis in the event that the number of the amino acids that have been estimated with an accuracy or score exceeding a certain value is less than a designated certain number, a y ion is preferentially selected as the parent ion.
(112) When conducting the $MS^{n+1}$ analysis or repeating the $MS^n$ analysis in the event that the number of the amino acids that have been estimated with an accuracy or score exceeding a certain value is less than a designated certain number, a bivalent ion is preferentially selected as the parent ion.
(113) In the even that a sequence is contained in the amino acid sequences estimated from the mass peak interval in the mass spectrum data in which dissociation is not easily caused, the $MS^{n+1}$ analysis is conducted or the $MS^n$ analysis is repeated.
(114) In the even that a designated sequence is contained in the amino acid sequences estimated from the mass peak interval in the mass spectrum data, the $MS^{n+1}$ analysis is conducted or the $MS^n$ analysis is repeated.
(115) A de novo peptide sequence method is used as the method of estimating the structural unit forming the parent ion within a specific time period.
(116) In the analysis of the result of the n-th stage mass spectroscopy ($MS^n$), namely the mass spectrum measurement result represented in terms of a peak of measurement intensity against the mass-to-charge ratio m/z of an ion, within the real time of measurement, peaks with an intensity less than a threshold value that is designated by the user or automatically set are eliminated, and then the number of remaining peaks is derived, wherein the next analysis content is determined based on the number of the mass peaks.
(117) In the next analysis content, the next $MS^1$ analysis measurement is conducted or the measurement is terminated if the number of the mass peaks is not less than a certain number designated by the user, for example, and if the number of the mass peaks is less than the designated number, the $MS^{n+1}$ analysis is conducted in which one of the ion species detected in the $MS^n$ data ($n \geq 2$) is selected, dissociated and subjected to mass spectroscopy, or, if an ion species with substantially identical mass number and a different valence from the parent ion in the $MS^n$ analysis has been detected in the $MS^{n-1}$ data, the ion species is selected and dissociated as the parent ion and the $MS^n$ analysis is automatically repeated.
(118) In the analysis of the result of the n-th stage mass spectroscopy ($MS^n$), namely the mass spectrum measurement result represented in terms of a peak of measurement intensity against the mass-to-charge ratio m/z of an ion, within the real time of measurement, a database search is conducted, in which database peptide sequences or the mass numbers thereof are stored upon enzymatic digestion of protein sequences.
(119) Based on mass spectrum measurement data, the peptide sequences in the database are further divided into partial sequences, the database in which the mass numbers of the peptide sequences are stored is searched, and the $MS^{n+1}$ analysis is conducted or the $MS^n$ analysis is repeated only for an ion for which no peptide has been identified.
(120) When automatically conducting the $MS^{n+1}$ analysis or repeating the $MS^n$ analysis in the event that the number of the amino acids that have been decoded is less than a certain designated number, if the valence of the parent ion in the $MS^n$ mass spectrum data that have been decoded is one, and if an ion species has been detected in the $MS^{n-1}$ data that has substantially identical mass number and a different valence (two or more) from the parent ion in the $MS^n$ analysis, the ion species is selected and dissociated as the parent ion and the $MS^n$ analysis is repeated.
(121) When automatically conducting the $MS^{n+1}$ analysis or repeating the $MS^n$ analysis in the event that the number of the amino acids that have been decoded is less than a certain designated number, if the valence of the parent ion in the $MS^n$ mass spectrum data that have been decoded is two or more, the $MS^{n+1}$ analysis is conducted.

Thus, in accordance with the present invention, automatic determination systems are provided in which, when conducting mass spectroscopy ($MS^n$) involving dissociation in multiple stages, the information contained in the $MS^n$ spectrum is effectively utilized in each stage of $MS^n$, and in which analysis flows for the determination of the next analysis content and for the selection of a parent ion for the $MS^{n+1}$ analysis, for example, can be optimized within the real time of measurement and with high efficiency and high accuracy. Thus, the systems make it possible to conduct tandem mass spectroscopy on a target of concern to the user.

Further, in accordance with the present invention, ions that are not the objects of analysis can be eliminated prior to a primary mass spectroscopy, so that the detection of an ion as the analysis object can be facilitated during the primary mass spectroscopy. Accordingly, the tandem mass spectroscopy of a target substance (analysis object ion) can be conducted on even a sample with much impurity components.

Further, in accordance with the present invention, particularly in the case of a mass spectrometer using an ion trap, the trapping of ions that are not the objects of analysis is made more difficult, so that the influence of space-charge effect in the ion trap can be reduced. Thus, a target substance (analysis object ion) can be subjected to tandem mass spectroscopy with high sensitivity.

What is claimed is:

1. A mass spectroscopy system comprising:

ionization means for ionizing a substance as an object of measurement for a mass spectrometer; and means for selecting an ion species with a specific mass-to-charge ratio m/z from ions produced by said ionization means and dissociating the same, wherein the selection, dissociation and measurement of the ion species as the measurement object are repeated in a plurality of stages, said mass spectroscopy system further comprising:

mass spectroscopy data acquisition means for performing the selection and dissociation of an ion species n−1 times (n≧1, where n is an integer) and acquiring a peak of measurement intensity against the mass-to-charge ratio of the ion that has been selected and dissociated;

correspondence determination means for comparing the peak of measurement intensity against the mass-to-charge ratio of the ion that is obtained by the mass spectroscopy data acquisition means with the characteristics data of a certain ion species in order to determine the possibility of correspondence of the ion that has been selected and dissociated to the certain ion species;

next-analysis content determination means for determining the analysis content in an n-th stage mass spectroscopy based on the result of determination by said correspondence determination means; and a data processing unit configured such that the combined time required by the correspondence determination means and the next-analysis content determination means is 10 milliseconds or less.

2. The mass spectroscopy system according to claim 1, wherein the next-analysis content determination means determines the implementation of an $MS^3$ analysis based on the number of contiguous amino acid residues that can be decoded from an acquired $MS^2$ spectrum.

3. The mass spectroscopy system according to claim 1, wherein the substance as the object of measurement is a protein, a peptide, a sugar chain, a polymer, a metabolite, or a lipid.

4. The mass spectroscopy system according to claim 1, wherein the next-analysis content determination means performs an $MS^2$ analysis when the amount of the ion that has been determined to be in correspondence by the correspondence determination means fluctuates by more than a certain value.

5. The mass spectroscopy system according to claim 1, wherein said data processing unit is one CPU.

6. The mass spectroscopy system according to claim 1, wherein said data processing unit includes a parallel computer or a CPU cluster.

* * * * *